(12) United States Patent
Lang

(10) Patent No.: US 7,328,132 B2
(45) Date of Patent: Feb. 5, 2008

(54) INPUT/LOSS METHOD USING THE GENETICS OF FOSSIL FUELS FOR DETERMINING FUEL CHEMISTRY, CALORIFIC VALUE AND PERFORMANCE OF A FOSSIL-FIRED POWER PLANT

(75) Inventor: Fred D. Lang, San Rafael, CA (US)

(73) Assignee: Exergetic Systems, LLC, San Rafael, CA (US)

( * ) Notice: Subject to any disclaimer, the term of this patent is extended or adjusted under 35 U.S.C. 154(b) by 0 days.

(21) Appl. No.: 11/378,999

(22) Filed: Mar. 17, 2006

(65) Prior Publication Data

US 2007/0219730 A1    Sep. 20, 2007

(51) Int. Cl.
G06F 11/30    (2006.01)
F22B 35/00    (2006.01)

(52) U.S. Cl. .................. 702/183; 702/22; 700/274
(58) Field of Classification Search .................. None
See application file for complete search history.

(56) References Cited

U.S. PATENT DOCUMENTS

| | | | |
|---|---|---|---|
| 5,367,470 | A | 11/1994 | Lang |
| 5,790,420 | A | 8/1998 | Lang |
| 6,522,994 | B1 * | 2/2003 | Lang ................... 702/183 |
| 6,560,563 | B1 | 5/2003 | Lang |
| 6,584,429 | B1 | 6/2003 | Lang |
| 6,651,035 | B1 | 11/2003 | Lang |
| 6,691,054 | B1 | 2/2004 | Lang |
| 6,714,877 | B1 | 3/2004 | Lang |
| 6,745,152 | B1 | 6/2004 | Lang |
| 6,799,146 | B1 | 9/2004 | Lang |
| 6,810,358 | B1 | 10/2004 | Lang et al. |
| 6,868,368 | B1 | 3/2005 | Lang |
| 6,873,933 | B1 | 3/2005 | Lang |

FOREIGN PATENT DOCUMENTS

| | | |
|---|---|---|
| AU | 762836 | 10/2003 |
| CA | 2325929 | 6/2004 |
| EP | 1171834 | 1/2005 |

OTHER PUBLICATIONS

Wolfram MathWorld, http://mathworld.wolfram.com/Closed-FormSolution.html.*
U.S. Appl. No. 10/715,319, filed Nov. 17, 2003, Lang.
FD Lang, "Monitoring and Improving Coal-Fired Power Plants Using the Input/Loss Method", American Society of Mechanical Engineers, International Joint Power Generation Conference, 1998-Pwr-33, pp. 789-797.

(Continued)

Primary Examiner—Manuel L. Barbee

(57) ABSTRACT

This invention relates to any fossil fueled thermal system, and especially relates to large commercial steam generators used in power plants, and, more particularly, to a method and apparatus for determining fuel chemistry in essentially real time based on effluents resulting from combustion, associated stoichiometrics, and the genetics of the fossil fuel. Knowing the system's fuel chemistry, the fuel calorific value, the fuel flow and the thermal performance associated with the thermal system may then be determined in essentially real time.

40 Claims, 24 Drawing Sheets

OTHER PUBLICATIONS

FD Lang and AF Lang, "Monitoring and Improving Coal-Fired Power Plants Using the Input/Loss Method—Part II", American Society of Mechanical Engineers, International Joint Power Generation Conference, 1999-Pwr-34, pp. 373-382.

FD Lang, "Monitoring and Improving Coal-Fired Power Plants Using the Input/Loss Method—Part III", American Society of Mechanical Engineers, International Joint Power Generation Conference, 2000-15079/CD; revised Jan. 6, 2003.

FD Lang, "Monitoring and Improving Coal-Fired Power Plants Using the Input/Loss Method—Part IV", American Society of Mechanical Engineers, International Joint Power Generation Conference, Pwr2004-52026 (CD).

S Vijiapurapu, "Real-Time Performance Monitoring of Coal-Fired Power Plants", Master's Thesis, Tennessee Technological University, Cookeville, TN, Dec. 2001.

S Vijiapurapu, R Craven and S Munukutla, "Parametric Studies of Power Plant Performance Monitoring", American Society of Mechanical Engineers, International Joint Power Generation Conference, 2002-26083 (CD).

R Craven, S. Munukutla, M Coffee and D Howard, "Real-Time Coal Analysis in a Coal-Fired Unit", Coal-Gen Conference, Jul. 31-Aug. 2, 2002, St. Louis, Mo.

G Kashmer, R Craven and S Munukutla, "Real-Time Performance Monitoring at Clover Station", Electric Power 2004 Conference, Mar. 30-Apr. 1, 2004, Baltimore, Maryland; only presentation material available.

S Munukutla and R Craven, "Field Experience with On-Line Heatrate Monitoring of Coal-Fired Units", Electric Power Research Institute, Heat Rate Conference, Jan. 2004; only presentation material available.

RM Davidson, "Studying the Structural Chemistry of Coal", IEA Clean Coal Centre, London, U.K., CCC/82, ISBN 92-9029-397-7, Apr. 2004.

DW van Krevelen and J Schuyer, "Coal Science, Aspects of Coal Constitution", Elsevier Science Publishers, Amsterdam, 1957; title, publisher, Table of Contents, pp. 9-31, 97-104.

DW van Krevelen, "Coal: Typology, Physics, Chemistry, Constitution", Third Edition, Elsevier Science Publishers, Amsterdam, 1993; title, publisher, Table of Contents, pp. 181-192.

J.G. Speight, "The Chemistry and Technology of Coal", Marcel Dekker Inc., New Yorl & Basel; pp. 3-19, 83-84 and 165-199, 1994.

"Standard Classification of Coals by Rank", ASTM D388, ASTM International, West Conshohocken, Penn., U.S., Jul. 2004.

"Standard Practice for Ultimate Analysis of Coal and Coke", ASTM D3176, ASTM International, West Conshohocken, Penn., U.S., Feb. 1990.

"Brown Coals and Lignites—Classification by Types on the Basis of Total Moisture Content and Tar Yield", ISO 2950-1974(E).

* cited by examiner

INPUT/LOSS METHOD USING THE GENETICS OF FOSSIL FUELS FOR DETERMINING FUEL CHEMISTRY, CALORIFIC VALUE AND PERFORMANCE OF A FOSSIL-FIRED POWER PLANT

FIELD OF THE INVENTION

This invention relates to any fossil fueled thermal system, and especially relates to large commercial steam generators used in power plants, and, more particularly, to a method and apparatus for determining fuel chemistry in essentially real time based on effluents resulting from combustion, associated stoichiometrics, and the genetics of the fossil fuel. Knowing the system's fuel chemistry, the fuel calorific value, the fuel flow and the thermal performance associated with the thermal system may then be determined in essentially real time.

BACKGROUND OF THE INVENTION

Although especially applicable to "The Input/Loss Method" as installed at fossil-fired power plants, this invention may also be applied to any one of the "Input/Loss methods" installed at any thermal system burning a fossil fuel. Definitions for quoted terms are provided in the section entitled MEANING OF TERMS. The following paragraphs discuss prior art associated with The Input/Loss Method and with generic Input/Loss methods.

The principle background teachings of The Input/Loss Method are described in three patents: U.S. Pat. No. 6,584,429 which issued Jun. 24, 2003 and teaches a high accuracy method of determining boiler efficiency, hereinafter referred to as '429; U.S. Pat. No. 6,714,877 which issued Mar. 30, 2004 and teaches how effluent concentrations resultant from combustion may be corrected for errors, hereinafter referred to as '877; and, most importantly, U.S. Pat. No. 6,522,994 which issued Feb. 18, 2003 and teaches general methods of The Input/Loss Method. U.S. Pat. No. 6,522,994 originated as a PCT application resulting in the following patents: Canadian Patent 2325929; Australian Patent 762836; and European Patent (DE, GB, GR & IT) 1171834. These patents, U.S. Pat. No. 6,522,994, Canadian 2325929, Australian 762836 and European 1171834, are hereinafter collectively referred to as '994.

'994 is incorporated herein by reference in its entirety. '429 is incorporated herein by reference in its entirety. '877 is incorporated herein by reference in its entirety. In addition to '994, '429 and '877, a considerable technological foundation for The Input/Loss Method may be found in the following U.S. Pat. Nos. 6,560,563, 6,651,035, 6,691,054, 6,745,152, 6,799,146, 6,810,358, 6,868,368 and 6,873,933. In addition. U.S. Pat. No. 7,039,555 which issued May 2, 2006 pertains to tube failure in Recovery Boilers; it was issued with Terminal Disclaimers against '994 and U.S. Pat. No. 6,651,035.

Further still, related pending applications which again add to the technology of The Input/Loss Method include the following: Canadian Patent Application No. 2479238, European Patent Office Application No. 02784559, and U.S. patent application Ser. No. 10/715,319. Canadian Patent Application No. 2479238 and European Patent Office Application No. 02784559 are the same, stemming from PCT/US02/37612 (WO2003/091881). The originating U.S. application represented by PCT/US02/37612 resulted in U.S. Pat. No. 6,651,035 which teaches how tube failures in large steam generators may be detected using The Input/Loss Method. U.S. Pat. No. 6,651,035 was originally filed as a U.S. Continuation-In-Part to an application which became U.S. Pat. No. 6,745,152. U.S. patent application Ser. No. 10/715,319 has resulted in an allowed U.S. application which principally teaches how tube failures in Recovery Boilers may be detected using The Input/Loss Method modified for sodium/hydrocarbon stoichiometrics, that application was published as US2004/128111.

One of the Input/Loss methods, a rudimentary method, is described in U.S. Pat. No. 5,367,470 which issued Nov. 22, 1994 (with Dec. 14, 1989 priority), and in U.S. Pat. No. 5,790,420 which issued Aug. 4, 1998. U.S. Pat. No. 5,790,420 was originally filed as a U.S. Continuation-In-Part to an application which became U.S. Pat. No. 5,367,470.

Other known Input/Loss methods are thoroughly discussed in the BACKGROUND OF THE INVENTION section of '994; this discussion is referenced herein as being important.

For many years the energy industry has attempted to categorize coals. Although there are four major ranks of coal in the U.S. classification scheme (anthracite, bituminous, sub-bituminous and lignite), these have been sub-divided by ASTM D388, "Standard Classification of Coals by Rank". Refer to TABLE B1 for ASTM D388 categories (an incorrect energy conversion was used in this standard, 2.3255 kJ/kg/Btu/lb, versus 2.3260 kJ/kg/Btu/lb). One problem immediately seen in TABLE B1 is its lack of specificity, ASTM D388 basically employs either As-Received calorific values, and/or proximate analyses on a dry basis to judge coals. "Ultimate Analysis" data is not employed. Higher Rank coals are classified according to fixed carbon on a dry basis while the lower Rank coals are classified by As-Received calorific value (wet basis). FIG. X1.1 of ASTM D388 presents a typical single-variant correction between weight fraction of volatile matter and Reflectance in oil. A general discussion of coal classifications may be found in the text *The Chemistry and Technology of Coal* by J. G. Speight, Marcel Dekker, Inc, New York & Basel, which discusses coal classifications in Chapter 1 (pages 3-19), elemental analysis on pages 83-84 and evaluation techniques in Chapter 8 (pages 165-199). Note that examples of single-variant analyses are presented in this text's FIGS. 1.2, 8.10, 8.11 and 8.12; several of these displaying weight fraction of fuel hydrogen versus weight fraction of fuel carbon. As seen, these plots represent only broad-brush correlations, hardly capable of supporting any of the Input/Loss methods.

TABLE B1

ASTM Classification by Rank

| Rank (abbreviation) | Characteristics |
|---|---|
| meta-anthracite (ma) | Fixed carbon ≧98%. |
| anthracite (an) | Fixed carbon ≧92% and <98%. |
| semi-anthracite (sa) | Fixed carbon ≧86% and <92%. |
| low volatile bituminous (lvb) | Fixed carbon ≧78% and <86%. |
| medium volatile bituminous (mvb) | Fixed carbon ≧69% and <78%. |
| high volatile A bituminous (hvAb) | CV ≧14000 Btu/lb (CV ≧32557 kJ/kg), with Fixed carbon <69% |
| high volatile B bituminous (hvBb) | 14000 Btu/lb > CV ≧ 13000 Btu/lb (32557 kJ/kg > CV ≧ 30232 kJ/kg) |
| high volatile C bituminous (hvCb) | 13000 Btu/lb > CV ≧ 10500 Btu/lb (30232 kJ/kg > CV ≧ 24418 kJ/kg) |
| sub-bituminous A (sub A) | 11500 Btu/lb > CV ≧ 10500 Btu/lb (26743 kJ/kg > CV ≧ 24418 kJ/kg) |
| sub-bituminous B (sub B) | 10500 Btu/lb > CV ≧ 9500 Btu/lb (24418 kJ/kg > CV ≧ 22090 kJ/kg) |
| sub-bituminous C (sub C) | 9500 Btu/lb > CV ≧ 8300 Btu/lb (22090 kJ/kg > CV ≧ 19300 kJ/kg) |

TABLE B1-continued

ASTM Classification by Rank

| Rank (abbreviation) | Characteristics |
|---|---|
| lignite A (lig A) | 8300 Btu/lb > CV ≧ 6300 Btu/lb (19300 kJ/kg > CV ≧ 14650 kJ/kg) |
| lignite B (lig B) | 6300 Btu/lb > CV (14650 kJ/kg > CV) |

There are seemingly as many coal categories used in Europe as countries. In general, Europeans categorize coal as either hard or soft depending on ash-free calorific value. Sub-groups are then classed by volatile matter, coking properties, etc. resulting in a complex three-digit numbering system. No European system employs Ultimate Analysis data to classify coals, at best proximate analyses are employed. Refer to "Brown Coals and Lignites—Classification by Types on the Basis of Total Moisture Content and Tar Yield", International Organization for Standards, ISO 2950-1974(E). The broad categorizations favored in Europe (i.e., hard or soft coals) is also reflected in the so-called van Krevelen diagrams whose use dates from 1950. Van Krevelen diagrams are plots of atomic hydrogen/carbon versus atomic oxygen/carbon ratios. This and related research is summarized in the books: D W van Krevelen and J Schuyer, "*Coal Science, Aspects of Coal Constitution*", Elsevier Science Publishers, Amsterdam, 1957; and D W van Krevelen, "*Coal: Typology, Physics, Chemistry, Constitution*", Third Edition, Elsevier Science Publishers, Amsterdam, 1993. If oxygen may be held constant, then van Krevelen diagrams reduce fundamentally to hydrogen versus carbon relationships found useful when applying '994 techniques.

It is also useful to recognize that the analysis of fossil fuels may be accomplished using the Excel® computer program. Excel is owned by the Microsoft Corporation, Redmond, Wash. state in the U.S. Excel is a registered trademark of Microsoft Corporation. Fossil fuel data is typically obtained as Ultimate Analysis data with As-Received fuel water, fuel ash and calorific values. As used to develop this invention, and used throughout its presentation herein, such data was analyzed using Excel. All "$R^2$ values" mentioned herein, commonly termed the Coefficient of Determination, have been computed by Excel using regression analysis. Excel's $R^2$ value represents the percent variation in a y-variable that is explained by the independent x-variable. Only linear regression was used herein. There are classical problems associated with $R^2$ values as are well known to one skilled in statistics. One such problem, and one important to this invention, is evident when data presents an even scatter about a linear mean. Such a situation might lead to a high $R^2$ value which does not truly reflect a y-variable being predictable by the independent x-variable (simply put, the $R^2$ value may appear acceptable, but the functionality is too coarse to be useable). The most straightforward method to address such situations is to simulate data patterns associated with their end use and to then evaluate the direct impact their variances have on computed output. For example, the impact on The Input/Loss Method's computed calorific value of a 1.0% variance in predicted fuel carbon (and thus affecting computed calorific value) may be assessed most conservatively by assuming a 1.0% variance in effluent $CO_2$; such a 1.0% variance may be observed, and verified, from plotted data. Another method of evaluating distributed data patterns is to simply apply engineering judgement by looking at the plots: they are either unreasonable or portend fundamental understanding with obvious certainty.

The technologies underwriting The Input/Loss Method, witnessed by the aforementioned patents and patent applications, were based on recognizing that if the effluent concentrations from combustion are used to determine fuel chemistry, then fundamentally more unknowns are involved than practical equations are available. '994 presented a solution to this problem by teaching that fuel hydrogen may have a functional relationship with fuel carbon; see Eq.(45) in '994 and the definition of "reference fuel characteristics" in '994. Other relationships are fuel oxygen versus fuel carbon, and fuel nitrogen versus fuel carbon; refer to Eqs. (43) and (44) in '994 and associated discussion above Eq.(42) in '994. For example, the correlation constants $A_5$ & $B_5$ used in Eq.(45) in '994 derive directly from ultimate analysis data, for example, as seen in FIG. 3 of '994. Eq.(42) in '994 presents an explicit solution to moisture-ash-free (MAF) molar fuel carbon employing correlation coefficients: $A_3$ & $B_3$ from MAF molar fuel oxygen as a function of MAF molar fuel carbon of Eq.(43) in '994; and $A_5$ & $B_5$ from MAF molar fuel hydrogen as a function of MAF molar fuel carbon of Eq.(44) in '994. These correlations provided the missing equations. They all are simple single-variant molar correlations using hydrogen versus carbon, or oxygen versus carbon; e.g., the single-variant is molar hydrogen as observed in '994 Eqs.(45). There was no other known art or techniques for solving the underlying problem.

Wherein The Input/Loss Method has been installed at a number of power plants, certain situations have arisen in which single-variant relationships such as fuel hydrogen versus fuel carbon are simply not adequate. This has been found true when employing "reference fuel characteristics" as defined and taught in '994. It has been found that this situation is especially true if dealing with the following fuel types: Irish peat; Powder River Basin coals; and what is termed "High Seas" coal. Irish peat is of importance as it represents a typical indigenous fuel source, not only for the Republic of Ireland, but also for Poland, for Finland and for Minnesota in the U.S. Peat's dry chemistry may vary considerably given its haphazard formation as immature coal, and its fuel water content typically varies wildly. The MAF characteristics of peat are not unlike lignite found in Texas, Australia and Greece. Powder River Basin coals have an enormous, and growing, financial impact on the United States and Canada as it represents the largest single source of coal fuel being fired in North American power plants. Over 120 power plants use Powder River Basin coals, growing by some estimates at 15%/year. Powder River Basin coals have low sulfur concentrations, but are high in fuel water with highly variable fuel chemistries reflecting over a dozen mines located in several western states in the U.S. High Seas coal is defined as high energy coal which is frequently bought, literally, while coal-carrying cargo ships are on the high seas. It may be categorized, as high volatile bituminous coal. High Seas coal typically has low fuel water, but fuel chemistries reflecting variability associated with world-wide sourcing. High Seas coal typically has calorific values in the range of 25,586 to 31,401 kJ/kg (11,000 to 14,000 Btu/lbm). There are other fuels which, it is anticipated, will receive higher interest over the coming years, but which will have similar variabilities. One such fuel is switch grass, grown in the U.S. as an environmentally friendly (and renewable) fossil fuel. Another, is wood waste (i.e., bio-mass fuel), being burned in the western states of the U.S. If Irish peat, Powder River Basin coals and High Seas coals were not significantly used, then the method taught in '994 would be adequate given a supposed well-characterized fuel. By well-characterized is meant that needed correlations (e.g., MAF molar fuel hydrogen as a function of MAF molar fuel carbon) have $R^2$ values which exceed 90%. Note however that if an $R^2$ value at 90% is considered inadequate (versus, say 98%), or not, the practical application of '994 was, indeed, limited to this level of predictability as a direct consequence of simple single-variant correlations.

It is important to note that "reference fuel characteristics", as defined in '994, represents a taught procedure, one in which hydrogen versus carbon relationships are developed based on historical fuel data. It does not specify usable data. When the method of '994 was installed in PRB burning powers plants, coal from specific regions within the Basin would require characterization. The Boardman Coal Plant, operated by Portland General Electric and using The Input/Loss Method, was characterized specifically to PRB Decker coal. The Nebraska City Unit 1, operated by Omaha Public Power District and using The Input/Loss Method, was characterized specifically to PRB Caballo Rojo coal. And the same even for Irish peat. The Lough Ree Power Station, operated by the Electricity Supply Board and using The Input/Loss Method, was characterized specifically to Irish peat found near Lanesboro, Ireland, although the West Offlay Power Station, also burning Irish peat, not 56 km (35 miles) away, was characterized specifically to the Shannonbridge region. '994 taught a procedure requiring historical data, requiring unique reference fuel characteristics to be programmed in a computer for each installation. What is needed is a generic method such that a single procedure satisfies an entire Rank of coal, without routine need of historical data. At the time of '994 there was no other known art. When considering variable fuels, as defined by poor $R^2$ values resultant from using simple single-variant correlations, the '994 method has not proven to be generic as it suffers from a lack of flexibility under certain circumstances.

The databases of Ultimate Analyses and calorific values used to develop this invention derive from the following sources: 1) Pennsylvania State University, Organic Petrology Laboratory database containing over 1200 Ultimate Analyses and associated calorific values from over 400 mines; 2) Powder River Basin coal data containing approximately 250 samples from 19 different regions within the Basin; 3) so-called High Seas coal data containing 320 samples from over 50 mines from 14 states in the U.S., South Africa, Poland, Russia and Colombia, this data includes numerous spot analyses obtained from power plants actually using such coal (i.e., from the Moneypoint station, Republic of Ireland, from the Brandon Shores station, Maryland state in the U.S., and from the Jorf Lasfar station, Morocco); and 4) Irish peat data containing approximately 160 samples from 6 different regions within the Republic of Ireland, notably the data having been collected over a considerable time period, from 1963 through 2005. In total the analyzed data consisted of approximately 1930 Ultimate Analyses and corresponding calorific values.

As seen in FIG. 1 for Irish peat, as seen in FIG. 3 for Powder River Basin coals, and as seen in FIG. 5 for High Seas coal the ability of '994 technology to reasonably provide functionality between MAF molar fuel diatomic hydrogen versus MAF molar fuel carbon is wanting, as based on simple single-variant correlations. For the Irish peat data of FIG. 1, the $R^2$ value was found at 65.90%. For the Powder River Basin coal data of FIG. 3, the $R^2$ value was found at 71.93%. For the High Seas coal data of FIG. 5, the $R^2$ value was found at 81.77%. Note, that although these fuels are not well-characterized using single-variant correlations, their industrial use is quite real; such use demands an improved approach. It also must be noted that a poor $R^2$ value for MAF molar fuel hydrogen versus MAF molar fuel carbon, portents an even poorer $R^2$ value for fuel oxygen versus fuel carbon; and poorer yet for fuel nitrogen versus fuel carbon. For MAF molar fuel oxygen versus MAF molar fuel carbon, the $R^2$ values were found at 36.48% for Irish peat, 14.01% for Powder River Basin coals and 64.23% for High Seas coals. Such non-predictability results forced the user of '994 technology, for these types of fuels, to assume that MAF molar fuel oxygen be keep constant. As an example of the practical problem, the typical power plants using High Seas coal (e.g., Moneypoint, Brandon Shores and Jorf Lasfar) do not sort the fuel, they burn whatever is on the loading docks having acquired the fuel from anywhere in the world based on price, etc. An improvement of methods is needed if such fuels are to be described with sufficient predictability for Input/Loss methods to function with the high accuracy of which it is capable. In summary the following features associated with '994 methods have proven to be inadequate:

- its use of "reference fuel characteristics", as defined in '994, employing single-variant correlations and its use of the $L_5$ Factor;
- "reference fuel characteristics", as defined in '994, require historical data;
- poor $R^2$ values (<90%) for the important MAF molar fuel hydrogen versus MAF molar fuel carbon relationships and very poor $R^2$ values (<70%) for oxygen versus carbon relationships which results in forcing MAF molar fuel oxygen to be held constant;
- the use of equations which solve for elemental constituents which combine single-variant correlation constants and stoichiometric terms;
- assuming fuel nitrogen is constant; and
- the use of numerical minimum and maximum limits applied to fuel concentrations as taught being a portion of the "reference fuel characteristics" defined in '994, has caused inconsistencies (as seen in FIG. 1, FIG. 3 and FIG. 5, a maximum $\alpha_{MAF-4}$ implies a minimum $\alpha_{MAF-5}$, and typically a minimum $\alpha_{MAF-3}$, thus the MAF summation could lead to inconsistencies which is an intrinsic disadvantage of single-variant analysis).

As demonstrated in FIG. 1, FIG. 3 and FIG. 5, the method taught in '994 simply cannot produce $R^2$ values near 98% for many important fuels without specialized study. If the fossil fuel is well characterized, and especially if the coal is of a higher Rank and having low fuel oxygen (e.g., anthracite, semi-anthracite and sub-bituminous A) the method of '994 using single-variant correlations may produce $R^2$ values near 90%. However, if to reach predictability values at the 98% level, understanding the genesis of fossil fuels is required. It requires a clear inventive step beyond the established technology of '994. There is no known art which addresses fundamental fossil fuel genetics such that $R^2$ values at the 98% level might be achieved, at least for the majority of commercial fuels. Other than '994 and other Input/Loss methods discussed in the BACKGROUND OF THE INVENTION section of '994, there is no established art directly related to this invention. There is a clear need for a methodology which describes fossil fuel genetics in such a manner that reliable and independent stoichiometrics may be resolved, thus allowing a "complete As-Fired fuel chemistry" determined from effluent concentrations.

SUMMARY OF THE INVENTION

This invention relates to any fossil fueled thermal system, and especially relates to large commercial steam generators used in power plants, and, more particularly, to a method and apparatus for determining fuel chemistry in essentially real time based on effluents resulting from combustion, associated stoichiometrics, and the genetics of the fossil fuel based on multi-variant analysis. In addition, this invention teaches a device which evaluates Ultimate Analysis data providing diagnostic information on the sample of coal. The use of "multi-variant analysis" has lead to the discovery of the "genetics of fossil fuels", numerically defining a wide range of fossil fuels. Further extension of the multi-variant analysis technique has lead to a new L-Factor, termed $L_{10}$, which may be used to correct effluent concentrations and other "Choice Operating Parameters" using '877 methods. Choice Operating Parameters are a sub-set of "Operating Parameters". Knowing the system's fuel chemistry, the fuel calorific value, the fuel flow and the thermal performance associated with the thermal system may then be determined in essentially real time. The teachings of this invention may be implemented for monitoring any thermal system burning a fossil fuel, or a thermal system burning a mix of fossil fuels and inorganic fuels such as Recovery Boilers. Such monitoring is assumed to be conducted in a continuous manner (i.e., on-line, in essentially real time), processing one monitoring cycle after another.

This invention, through new a method, apparatus and device, extends the technology associated with Input/Loss methods and teaches its industrial use by computer producing a complete As-Fired fuel chemistry and to evaluate Ultimate Analysis data. Specifically The Input/Loss Method has been applied through computer software, installable on a personal computer termed a "Calculational Engine", and has been demonstrated as being highly useful to the operators of fossil-fired systems. The Calculational Engine receives data from the system's data acquisition device. The Calculational Engine's software consists of the ERR-CALC, EX-FOSS, FUEL and HEATRATE executable computer programs described herein, and in '994, '429 and '877. The programs ERR-CALC and HEATRATE have been modified by the teachings of this invention. The Calculational Engine continuously monitors system efficiency on-line, i.e., in essentially real time, as long as the thermal system is burning fuel. The application of this invention to The Input/Loss Method significantly enhances the system operator's ability to understand coal-fired power plants.

The present invention provides a procedure, termed multi-variant analysis, which allows discovery of the genetics of fossil fuels, from which generates matrix solution to fuel chemistry based on effluents ("Choice Operating Parameters").

The present invention provides a new L-Factor, termed $L_{10}$, which allows effluents from combustion to be corrected using the methods taught in '877. The high consistency observed in $L_{10}$ has resulted directly from the genetics of the fossil fuel as based on multi-variant analysis.

The present invention, founded on multi-variant analysis, also teaches how fuel flow may be computed, and with a determined boiler efficiency and knowing the energy flow to the working fluid, results in a system thermal efficiency through which the system operator receives essentially real time feed-back as to whether his/her adjustments to the system do good or harm to efficiency.

The present invention teaches a new method to classify coals, replacing or improving common standards such as ASTM D388 and ISO 2950. The present invention also provides a method and device to distinguish data outliers associated with Ultimate Analyses.

Other objects and advantages of the present invention will become apparent when its general methods are considered in conjunction with the accompanying drawings.

According to a first embodiment the present invention provides a method for quantifying the operation of a thermal system burning a fossil fuel having a heat exchanger/combustion region producing combustion products, the method comprising the steps of:

before on-line operation, using a genetics of the fossil fuel based on multi-variant analysis; and while operating on-line, using a mathematical description of the thermal system, the step of operating on-line comprising the steps of measuring a set of measurable Operating Parameters, including at least effluent concentrations of $O_2$ and $CO_2$, these measurements being made at a location downstream of the heat exchanger/combustion region of the thermal system, obtaining an effluent concentration of $H_2O$, as an obtained effluent $H_2O$, obtaining a fuel ash concentration selected from the group consisting of: a constant value of fuel ash, a predictable value of fuel ash, a measured value of fuel ash determined from a fuel ash instrument and a value of fuel ash determined from explicit solution, as an obtained fuel ash concentration, obtaining a concentration of $O_2$ in the combustion air local to the system, obtaining an Air Pre-Heater Leakage Factor, and operating a programmed computer to obtain a complete As-Fired fuel chemistry, including fuel water and fuel ash, based on the genetics of the fossil fuel, the mathematical description, the set of measurable Operating Parameters, the obtained effluent $H_2O$, the obtained fuel ash concentration, the concentration of $O_2$ in the combustion air local to the system and the Air Pre-Heater Leakage Factor.

According to a second embodiment the present invention provides a method for quantifying the operation of a thermal system burning a fossil fuel having a heat exchanger/combustion region producing combustion products, the method comprising the steps of:

before on-line operation, developing a genetics of the fossil fuel based on multi-variant analysis; and while operating on-line, developing a mathematical description of the thermal system, the step of operating on-line comprising the steps of measuring a set of measurable Operating Parameters, including at least effluent concentrations of $O_2$ and $CO_2$, these measurements being made at a location downstream of the heat exchanger/combustion region of the thermal system, obtaining an effluent concentration of $H_2O$, as an obtained effluent $H_2O$, obtaining a fuel ash concentration selected from the group consisting of: a constant value of fuel ash, a predictable value of fuel ash, a measured value of fuel ash determined from a fuel ash instrument and a value of fuel ash determined from explicit solution, as an obtained fuel ash concentration, obtaining a concentration of $O_2$ in the combustion air local to the system, obtaining an Air Pre-Heater Leakage Factor, and operating a programmed computer to obtain a complete As-Fired fuel chemistry, including fuel water and fuel ash, based on the genetics of the fossil fuel, the mathematical description, the set of measurable Operating Parameters, the obtained effluent $H_2O$, the obtained fuel ash concentration, the concentration of $O_2$ in the combustion air local to the system and the Air Pre-Heater Leakage Factor.

One of the advantages of these method embodiments is that they allow the genetics of fossil fuels to be determined based on multi-variant analysis. As will be apparent from the following description, each fossil fuel has unique molecular characteristics which are now knowable. Thus, as has been found when developing this invention, multi-variant relationships differ between broad fuel types, and differ consistently. A further advantage of the methodologies of the present invention is that they allow elucidation of the genetics of fossil fuels such that a reliable set of independent equations, including stoichiometric equations independent of correlation constants, can be formed to resolve a complete As-Fired fuel chemistry based on effluent concentrations by matrix solution. As is obvious in its mathematics, the advantage of stoichiometric equations independent of correlation constants implies that their development involves only common manipulations of a combustion equation, easily accomplished by one of original skill.

According to a third embodiment the present invention provides for an apparatus for assisting the operation of a thermal system burning fossil fuel, the apparatus comprising:

a data acquisition device to collect data from the thermal system including at least a selection of Choice Operating Parameters, the data acquisition device producing a set of acquired system data;

a computer with a processing means;

a set of instructions for configuring the processing means to determine a fuel chemistry of the fossil fuel and to receive as input the set of acquired system data, resulting in a programmed computer;

means by which the programmed computer receives as input the set of acquired system data;

the programmed computer producing the fuel chemistry of the fossil fuel; and means for reporting the fuel chemistry of the fossil fuel to assist in the operation of the thermal system.

According to a fourth embodiment the present invention provides a device for evaluating an Ultimate Analysis of a coal sample, the device comprising:

a set of instruments capable of producing the Ultimate Analysis of a coal sample and to produce an Ultimate Analysis output, said output comprising at least carbon, hydrogen and oxygen concentrations;

a data processing device with a processing means and a memory means wherein the memory means stores a set of descriptive fossil fuel data based on the genetics of fossil fuels organized by categories;

a set of instructions for configuring the processing means to compare the Ultimate Analysis with the set of descriptive fossil fuel data and to receive as input the Ultimate Analysis output from the set of instruments, resulting in a programmed data processing device capable of producing a comparative report on the Ultimate Analysis;

the set of instruments producing the Ultimate Analysis output;

means of communicating the Ultimate Analysis output from the set of instruments to the programmed data processing device;

the data processing device producing the comparative report on the Ultimate Analysis; and means of communicating the comparative report on the Ultimate Analysis.

One of the advantages of the apparatus embodiment of this invention is that it provides a computing vehicle for calculating a real time complete As-Fired fuel chemistry of a coal-fired power plant, providing needed information to the operator. Also, one of the advantages of the device embodiment of this invention is that it provides a computing vehicle for evaluating Ultimate Analysis data, providing diagnostic information on coal sample analyses. Both of these advantages stem from the consistency found in the genetics of fossil fuels.

BRIEF DESCRIPTION OF THE DRAWINGS

FIG. 8 follows the teachings of this disclosure. Refer to TABLE 2 for functionalities.

FIG. 14 follows the teachings of this disclosure. FIG. 14 represents the bases for generic determination of effluent $CO_2$ for a wide variety of fossil fuels. Refer to TABLE 3 for functionality.

FIG. 15 follows the teachings of this disclosure. The Ultimate Analysis data of High Seas coal were found more similar to hvAb and hvBb than hvCb, thus hvCb was dropped such that the resultant average MAF chemistry would lie within the High Seas database (an arbitrary choice). The resultant $R^2$ value is 97.27%. Refer to TABLE 7 for functionalities.

FIG. 16 follows the teachings of this disclosure. The resultant $R^2$ value is 99.25%. Note that a corrected $L_{10}$ is also plotted indicating an essentially constant $L_{10}$, following the teaching of Eq.(73). Refer to TABLE 8 for functionalities.

FIG. 20 also illustrates "Fuel Iterations" involving FUEL, EX-FOSS and HEATRATE.

DESCRIPTION OF THE PREFERRED EMBODIMENT

Figure 1:
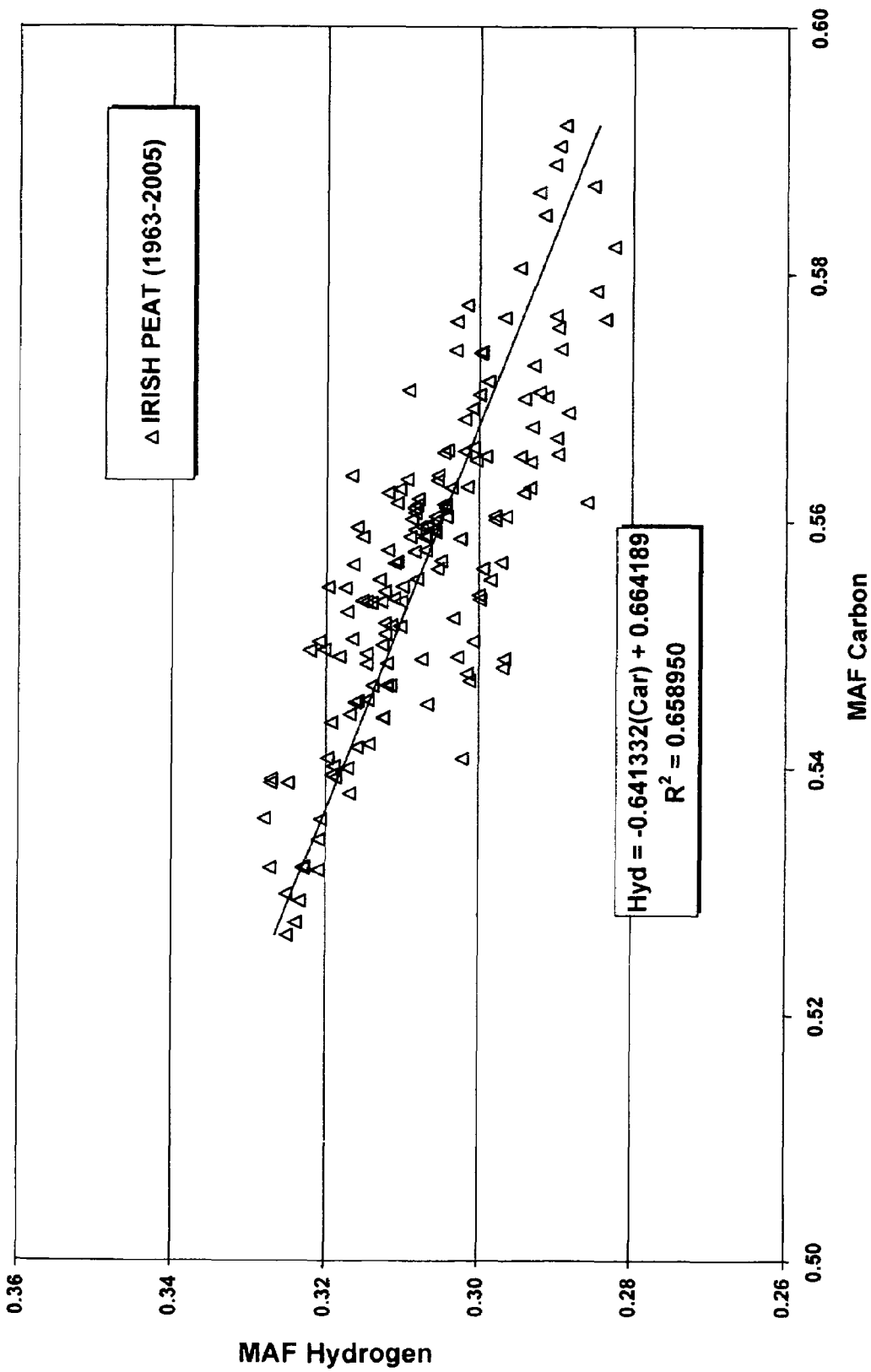
FIG. 1 (prior art) is a plot of MAF molar fuel diatomic hydrogen versus MAF molar fuel carbon for Irish peat following the teachings of '994, and as such it is considered prior art. The resultant $R^2$ value is 65.90%.

To assure an appropriate teaching of this invention, its description is divided by sub-sections. The first two present nomenclature, definitions of equation terms, typical units of measure, and meaning of terms used herein (such as Choice Operating Parameters and System Effect Parameters, the genetics of the fossil fuel, etc.). The remaining sub-sections, representing the bulk of the teachings, are divided as follows: system stoichiometrics; genetics of fossil fuels including a device to over-check Ultimate Analyses; the $L_{10}$ Factor and its use; determining complete As-Fired fuel chemistry; determining calorific value, boiler efficiency, fuel and effluent flows; correcting Choice Operating Parameters which includes a discussion on benchmarking real time monitoring systems; and the Calculational Engine apparatus required to operate this invention. These principle sections are then followed by a conclusion, THE DRAWINGS and related teachings. Determining a high accuracy boiler efficiency is taught in '429. Teachings of multidimensional minimization techniques, as broadly applicable to this invention are presented in '877. The present invention expands the accuracy and consistency of all Input/Loss methods when monitoring fossil fired steam generators in real time, and specifically builds upon and further expands the utility of The Input/Loss Method described herein and in '994, '429 and '877.

Definitions of Equation Terms and Typical Units of Measure Stoichiometric Terms:

$a$=Moles of combustion $O_2$ input to the system; moles/base.

$a\beta$=$O_2$ entering with system air leakage (typically via the air pre-heater); moles/base.

$a_{DRY-theor}$=Moles of combustion $O_2$ input to the system required for theoretical combustion associated with Dry (water free) fuel; moles/base.

$A_{Act}$=Concentration of $O_2$ in combustion air local to (and entering) the system as combustion air; the reference value for $A_{Act}$ is taken as 0.20948 obtained from the United States National Aeronautics and Space Administration (U.S. Standard Atmosphere 1976, NOAA-S/T-76-1562-NASA); molar fraction.

$b_A$=Moisture in the entering combustion air; directly proportional to the ambient air's specific humidity ($\omega_{Act}$); moles/base.

$=\omega_{Act} a(1.0+\phi_{Act})N_{DRY-AIR}/N_{H2O}$ $b_A\beta$=Moisture entering with system air leakage; moles/base.

$b_Z$=Moles of known water in-leakage entering and mixing with the combustion gases; moles/base.

$b_{PLS}$=Moles of pure limestone ($CaCO_3$) required for zero effluent CaO production moles/base.

$\equiv k_F - k_{Act} - r$ $d_{Act}$=Total effluent $CO_2$ at the system's boundary (i.e., Stack); moles/base.

g=Calculated effluent $O_2$ at the system's boundary without air leakage; moles/base.

$G_{Act}$=Total effluent oxygen at the system's boundary (g+a$\beta$); moles/base.

$G_{OHC1}$=Fitting intercept constant for $L_{10}$ versus MAF molar fuel diatomic oxygen, also termed a "fossil fuel regression constant"; molar fraction.

$G_{OHC2}$=Fitting intercept constant for $L_{10}$ versus MAF molar fuel carbon plus MAF fuel diatomic hydrogen, also termed a "fossil fuel regression constant"; molar fraction.

$H_{OHC1}$=Fitting slope constant for $L_{10}$ versus MAF molar fuel diatomic oxygen, also termed a "fossil fuel regression constant"; molar fraction.

$H_{OHC2}$=Fitting slope constant for $L_{10}$ versus MAF molar fuel carbon plus MAF molar fuel diatomic hydrogen, also termed a "fossil fuel regression constant"; molar fraction.

j=Calculated effluent $H_2O$ at the system's boundary without air leakage; moles/base.

$J_{Act}$=Total effluent water at the system's boundary (j+ $b_A\beta$); moles/base.

$J_{theor}$=Total effluent water at the system's boundary based on theoretical combustion of dried fuel; moles/base.

$J_{OHCk}$=Fitting intercept constants for MAF molar fuel quantities (k=1 for C+H, k=2 for C+O, and k=3 for H+O), also termed a "fossil fuel regression constant"; molar fraction.

$k_{Act}$=Effluent $SO_2$ measured at the system's boundary; moles/base.

$k_F$=A computed $SO_2$ equivalent to fuel sulfur ($x\alpha_6$) but less $SO_3$ production, and before limestone conversion or ash capture; moles/base.

$\equiv x\alpha_6(1.0-\Gamma_{SO3})$.

$K_{OHCk}$=Fitting slope constants for MAF molar fuel quantities (k=1 for C+H, k=2 for C+O, and k=3 for H+O), also termed a "fossil fuel regression constant"; molar fraction.

l=Effluent $SO_3$ at the system's boundary, a computed quantity; moles/base.

$n_i$=Molar quantities of dry gaseous effluents of combustion at the system boundary, without the air leakage terms; specifically those products associated with the following quantities:

$d_{Act}$, g, h, $k_{Act}$, $e_{Act}$, f, l, m, p, q, t and u;

note: $\Sigma n_i \equiv 100$ moles of dry gaseous effluent at the Stack is the assumed calculational "base" for Eq.(29F), see FIG. 19; moles/base.

Figure 19:
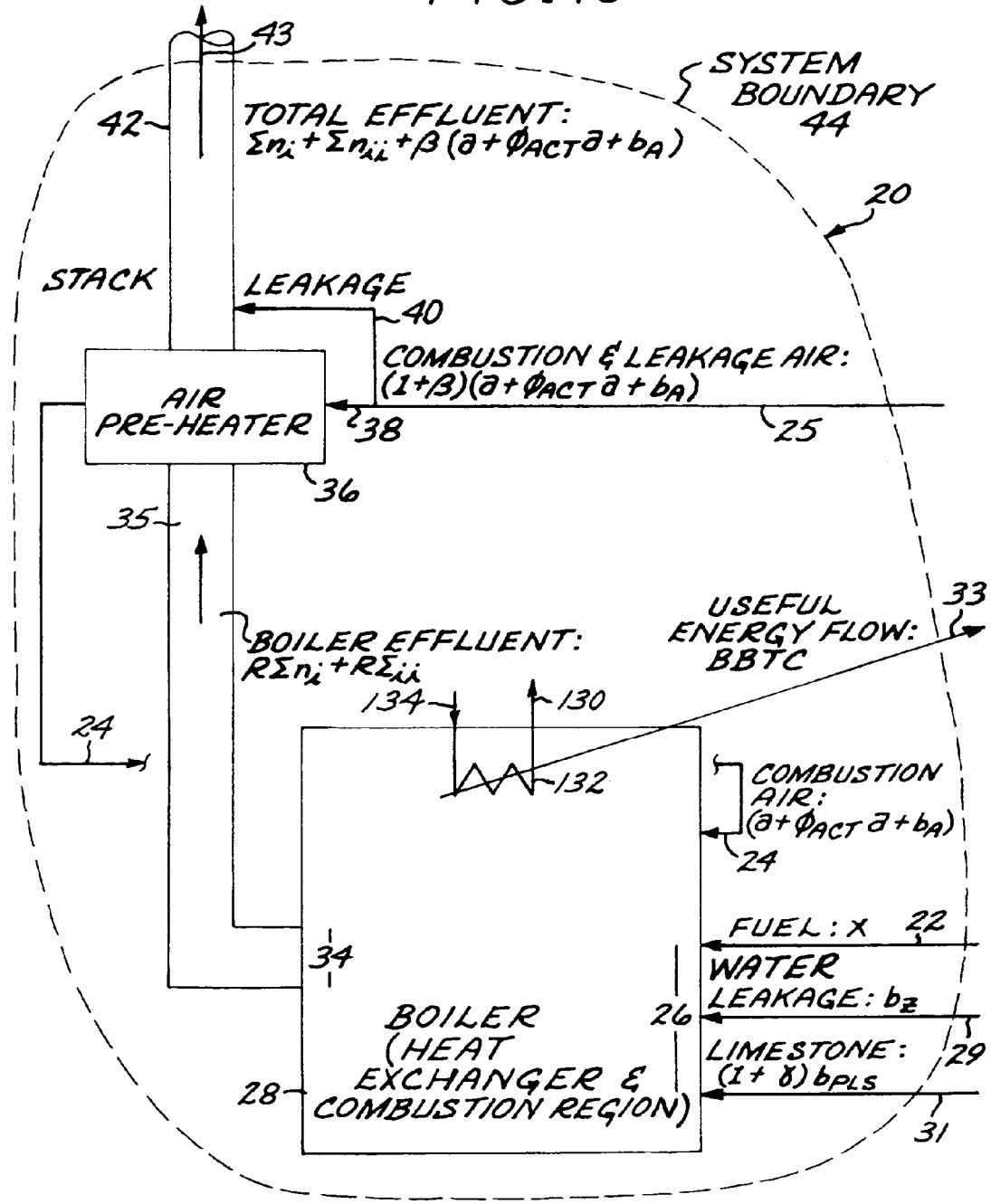
FIG. 19 is a schematic representation of a steam generator illustrating the application of stoichiometric relationships, and also contains definitions of some of the important terms used herein.

$n_{ii}$=Molar quantities of non-gas products of combustion at the system boundary, without the moisture term associated with air leakage, specifically those products associated with the following quantities:

j, r, $x\alpha_{10}$, $(1.0+\gamma)b_{PLS}$, v and w; see Eq.(29F) and FIG. 19; moles/base.

$N_k$=Molecular weight of compound k.

r=$SO_2$ captured by effluent ash; moles/base.

$R_{Act}$=Ratio of moles of dry non-atmospheric gas from the combustion process before entering the air pre-heater to the diluted non-atmospheric gas leaving, typically: (Moles of $CO_2$ entering the air pre-heater)/(Moles of $CO_2$ leaving the air pre-heater); defined as the Air Pre-Heater Leakage Factor; note that $R_{Act}$ may be assumed to be unity (=1.00) indicating no leakage is present (as may be assumed with Tubular Air Heaters); molar fraction.

$R'_{Act}$=Ratio of moles of dry atmospheric gas from the combustion process before entering the air pre-heater to the enriched atmospheric gas leaving, typically: (Moles of $O_2$ entering the air pre-heater)/(Moles of $O_2$ leaving the air pre-heater); molar fraction.

$WF_j$=As-Fired fraction of fuel composition j; weight fraction.

$WF_{H2O}=WF_2$=As-Fired fuel water fraction; weight fraction.

x=Moles of As-fired fuel required per 100 moles of dry gaseous effluent; moles/base.

$x_{theor}$=Moles of As-Fired fuel associated with theoretical combustion of dried fuel; moles/base.

$x_{DRY-theor}$=Moles of Dry fuel associated with theoretical combustion of dried fuel; moles/base.

$x_{MAF-theor}$=Moles of Moisture-Ash-Free (MAF) fuel associated with theoretical combustion of dried fuel; moles/base.

$x\alpha_{10}$=Mineral matter in As-Fired fuel, the terms "mineral matter" and "ash" are used interchangeably; moles/base.

z=Moles of $H_2O$ per mole of $CaSO_4$, supplied as input based on periodic laboratory analysis of boiler refuse, a minor term; molar fraction.

$\alpha_k$=As-Fired (wet-base) fuel constituent k per mole of fuel; $\Sigma\alpha_k$=1.0, where: k=1,2,3,4,5,6,10; see Eq.(29F) therein for terms; mole-k/mole-fuel.

$\alpha_{MAF-k}$=Moisture-Ash-Free (MAF) fuel constituent k per mole of MAF fuel;
$\Sigma\alpha_{MAF-k}$=1.0, where: k=1,3,4,5,6; see Eq.(29F) therein for terms; mole-k/mole-fuel.

$\beta$=Air Pre-Heater Dilution Factor (ratio of air leakage to true combustion air);
note that $\beta=f(R_{Act}, a, \phi_{Act})$ is defined below and developed by Eq.(22); if using $R'_{Act}$ then:
$R_{Act}=f(R'_{Act}, G_{Act}, \phi_{Act})$ per Eqs.(23), or
$R_{Act}=f(R'_{Act}, g'_{Act}, \phi_{Act})$ per Eqs.(23); molar fraction
$\beta \equiv 100(R_{Act}-1.0)/[a\ R_{Act}(1.0+\phi_{Act})]$ $\sigma$=Kronecker function: unity if $\alpha_6$>0.0, zero if no sulfur is present in the fuel.

$\gamma$=Molar ratio of excess $CaCO_3$ to stoichiometric $CaCO_3$ (e.g., $\gamma$=0.0 if no effluent CaO is present); molar fraction.

$\gamma=[(m_{LS}/m_{AF})\times N_{AF}/(\xi\ b_{PLS}N_{CaCO3})]-1.0$; where $m_{LS}$ is the system's indicated plant limestone flow, and $\xi$ is a mass ratio of actual limestone to pure $CaCO_3$ it contains.

$\Gamma_{SO3}$=Ratio of effluent $SO_3$ (l) to total fuel sulfur, $x\alpha_6$; see Eq.(29F); molar ratio
$\equiv l/(k_F+l)$ $\Gamma_{ESP}$=Ratio of $SO_2$ at the system boundary, to $SO_2$ found before ash capture (i.e., before the Electrostatic Precipitator or desulfurization system) and after limestone conversion; molar ratio
$\equiv k_{Act}/(k_{Act}+r)$ $\phi_{Act}$=Ratio of non-oxygen gases ($N_2$ and Ar) to oxygen in the combustion air; molar ratio.

$\phi_{Act} \equiv (1.0-A_{Act})/A_{Act}$ $\phi_{Ref}$=Reference ratio of non-oxygen gases (principally $N_2$ and Ar) to oxygen in the combustion air taken as 3.7737254 as being based on $A_{Act}$=0.20948; molar ratio.

Quantities Related to System Terms:

$AF_{input}$=Indicated Air/Fuel ratio defined by the indicated air flow and $m_{AF-PLT}$; unitless mass ratio.

$AF_{Act}$=Normalized Air/Fuel ratio; unitless mass ratio.

BBTC=Energy flow to the working fluid heated by combustion products; kJ/hr (Btu/hr).

$H_{Act}$=Relative humidity of ambient air local to the thermal system as a function of the psychrometric state; see Operating Parameters; fraction.

HBC≡Firing Correction; $kJ/kg_{AF}(Btu/lbm_{AF})$.

$HHV_{AF}$=Gross (or higher) calorific value; $kJ/kg_{AF}(Btu/lbm_{AF})$.

HHVP=As-Fired gross calorific value, based on $HHV_{AF}$ and used in system evaluations as corrected for a constant pressure process; $kJ/kg_{AF}$ $(Btu/lbm_{AF})$.

HR=System heat rate (HHV-based as $HR_{HHV}$; or LHV-based as $HR_{LHV}$); kJ/kWh (Btu/kWh).

$LHV_{AF}$=Net calorific value based on the measured or calculated gross calorific value ($HHV_{AF}$); $kJ/kg_{AF}(Btu/lbm_{AF})$.

LHVP=As-Fired net calorific value, based on $LHV_{AF}$ and used in system evaluations as corrected for a constant pressure process; $kJ/kg_{AF}$ $(Btu/lbm_{AF})$.

$m_{AF}$=As-Fired fuel flow; $kg_{AF}/hr$ $(lbm_{AF}/hr)$.

$m_{AF-PLT}$=Indicated plant fuel flow; $kg_{AF}/hr$ $(lbm_{AF}/hr)$.

$m_{LS}$=Indicated plant limestone flow associated with a thermal system such as a fluidized bed thermal system; $kg_{AF}/hr$ $(lbm_{AF}/hr)$.

$m_T$=Tube leakage flow; $kg_{AF}/hr$ $(lbm_{AF}/hr)$.

T=Temperature; ° C. (° F.).

$T_{Amb}$≡Ambient temperature local to the system, ° C. (° F.).

$T_{Cal}$≡Calorimetric temperature to which calorific value is referenced; ° C. (° F.).

$T_{Stack}$≡Boundary temperature of the system effluents, the effluent temperature, defines the "Stack"; ° C. (° F.).

$W_{output}$=Gross power generated from a power plant; kWe.

$\eta_{SYS}$=System efficiency (HHV-based as $\eta_{SYS-HHV}$; or LHV-based as $\eta_{SYS-LHV}$); unitless $\eta_B$=Boiler efficiency (HHV-based as $\eta_{B-HHV}$; or LHV-based as $\eta_{B-LHV}$); unitless.

$\omega_{Act}$=Specific humidity of ambient air local to the thermal system as a function the psychrometric state; see Operating parameters; kg-moisture/kg-dry-air (lbm-moisture/lbm-dry-air).

Subscripts and Abbreviations:

Act=Actual value obtained from the operating thermal system.

AF=As-Fired condition at the thermodynamic boundary (e.g., if fuel, As-Fired is wet with water and mineral matter).

DRY=Dry chemical base (i.e., free of water).

MAF=Moisture-Ash-Free chemical base (i.e., free of water and free of mineral matter).

PLS=Pure limestone ($CaCO_3$).

Ref=Reference value.

theor=Refers to conditions associated with theoretical combustion of dried fuel.

Meaning of Terms

The words "Operating Parameters", as taken within the general scope and spirit of the present invention, mean common data obtained from a thermal system applicable to the thermodynamic understanding of that system. The following quantities may be included in the definition of Operating Parameters, they are not encompassing but considered typical of a minimum set of data required for such thermodynamic understanding: effluents $CO_2$ and $O_2$ concentrations determined at the Stack, or before the air pre-heater (Boiler side of the air pre-heater); effluent $SO_2$ concentration if fuel sulfur is present, determined at the Stack, or before the air pre-heater (Boiler side of the air pre-heater); the mass, wet-base ratio of the indicated combustion air flow at the system's combustors, to the indicated plant fuel flow, termed $AF_{Act}$ (note that $AF_{Act}$ is obtained only for the determination of fuel ash as taught herein); effluent $H_2O$ concentration measurement, or assumptions made (or as otherwise may be determined); effluent temperature measurement, that is the average temperature associated with the combustion gases at the system boundary (caution must be exercised in measuring non-stratified gas flows); the inlet/outlet ratio of $CO_2$ (producing $R_{Act}$ as is preferred), or $O_2$ (producing $R'_{Act}$) across the air pre-heater where these ratios could be obtained on-line, off-line, based on periodic testing or judgement of such ratios used for the determination of air pre-heater leakage; determination of fuel temperature at an appropriate system boundary; air psychrometric measurements leading to relative and specific humidities, or as otherwise determined, at the system boundary (e.g., dry and wet bulb temperatures, or dry bulb and relative humidity, or dry bulb and dew point temperatures); quantities comprising the system's Firing Correction term, HBC as taught in '429; the discharge temperatures of the air as it exits each air heating or cooling device but before it reacts with the fuel (for example, such devices might include the air pre-heater, forced-draft fan, steam-to-air heater, etc.); and similar quantities. Operating Parameters also include a basic understanding of the fuel being burned: its general classification, its general water and its ash contents, and typical calorific values to be expected. Operating Parameters include the energy flow to the working fluid heated by combustion products (BBTC). For a typical steam generator, the measurements required to determine BBTC typically include feedwater flow to the steam generator, feedwater pressure and temperature, determination of the steam flow from the steam generator if different than the feedwater flow, steam pressure, steam temperature or quality (or assumed quality), and, if applicable, reheat flows, and reheat inlet and outlet pressures and temperatures. If employing a Reheater heat exchanger, determination of accurate reheat flows generally requires understanding of steam turbine flow distributions (involving high pressure turbine shaft seals, steam flows to feedwater heaters, turbine bypass leakages, attemperation spray flows and the like). Operating Parameters also include the electrical generation produced ($W_{output}$) if the working fluid powers a turbine-generator cycle.

The words "Choice Operating Parameters" (COP), as taken within the general scope and spirit of the present invention, are defined as meaning any sub-set of Operating Parameters which directly impact system stoichiometrics, and thus may impact the determination of fuel chemistry as taught herein. This invention assumes that Choice Operating Parameters may have error, said error may adversely affect the determination of fuel chemistry, but said error may be corrected as taught herein and through the optimization methods of '877. In the Preferred Embodiment Choice Operating Parameters are selected by the user of this invention from an available set. This available set of Choice Operating Parameters includes the following nine: 1) effluent $CO_2$ concentration measured at the Stack or Boiler; 2) $H_2O$ concentration measured, or as otherwise may be determined, at the Stack or Boiler; 3) the mass, wet-base ratio of the indicated combustion air flow at the system's combustors, to the indicated plant fuel flow, the Air/Fuel ratio termed $AF_{Act}$; 4) the Air Pre-Heater Leakage Factor, termed $R_{Act}$, which may be $\geq 1.00$, where unity (=1.00) indicates no leakage is present (as may be the case with Tubular Air Heaters); 5) the concentration of $O_2$ in the combustion air local to the system, or as otherwise determined, termed $A_{Act}$ (leading to the determination of $\phi_{Act}$); 6) the system's indicated plant limestone flow, termed $m_{LS}$; 7) effluent $O_2$ concentration measured at the Stack or Boiler; 8) mass flow associated with a heat exchanger tube leakage, termed $m_T$; and 9) the relative humidity of the ambient air local to the thermal system and which is associated with its combustion air, termed $H_{Act}$.

The words "System Effect Parameters" (SEP), as taken within the general scope and spirit of the present invention, mean any parameter of the thermal system or its fuel which directly impacts the determination of system efficiency. In the most general sense System Effect Parameters include any parameter used in Eqs.(103), (104A) through (105B) which allow system efficiency and thus system heat rate to be computed. For the Preferred Embodiment, System Effect Parameters include the following four types of quantities: the $L_{10}$ Factor; the computed As-Fired fuel flow ($m_{AF}$); the gross calorific value (either $HHV_{AF}$, $HHV_{DRY}$ or $HHV_{MAF}$); and the As-Fired fuel water fraction ($WF_{H2O}$) which may be used for determination of tube leakage or to convert $HHV_{DRY}$ to $HHV_{AF}$. The computed $L_{10}$ Factor is directly affected by fuel chemistry (of course fuel chemistry affects calorific value and boiler efficiency), and thus the $L_{10}$ Factor through fuel chemistry has an immediate impact on system efficiency. "Reference System Effect Parameters" are constant and targeted (i.e., desired) System Effect Parameters to which the System Effect Parameters are numerically driven by the minimization techniques through optimizing a selection of Choice Operating Parameters.

The words "Input/Loss methods", as taken within the general scope and spirit of the present invention, mean any method or combination of methods in which one or more of the following parameters is determined based on effluent concentrations and/or a selection of Choice Operating Parameters: moisture-ash-free fuel chemistry, dry fuel chemistry (i.e., water free), complete As-Fired fuel chemistry, fuel calorific value (i.e., fuel heating value), boiler efficiency, fuel flow, and/or effluent flow. In addition to '994, '429 and '877 and related patents, Input/Loss methods include the methods of U.S. Pat. Nos. 5,367,470 and 5,790,420. The words "The Input/Loss Method" refers specifically to the collection of technologies described in '994, '429 and '877, in addition to the teachings disclosed herein.

As used herein, the words "Calculational Engine" refers to a computer with a processing means and a memory means. Typically said computer is a common personal computer in which software descriptive of The Input/Loss Method as taught herein is installed (i.e., resulting in a programmed computer). Said computer may also include, broadly, any data processing unit such as a specialized computer, a hand-held computer, or an integrated circuit, all of which are capable of receiving sets of instructions and has memory (i.e., having a processing means and a memory means).

As used herein, if used, the words "obtain", "obtained", "obtaining", "determine", "determined", "determining", "determination", "establish", "established" or "establishing" are defined as measuring, calculating, computing, assuming, estimating or gathering from a database.

As used herein, the words "monitoring" or "monitored" are meant to encompass both on-line monitoring (i.e., processing system data in essentially real time) and off-line monitoring (i.e., computations involving static data). A "monitoring cycle" is meant to be one execution of the processes described in FIG. 20B and FIG. 20C.

As used herein, the words "smoke Stack" or "Stack" or "system boundary" are defined as the physical boundary of the thermal system where gaseous combustion effluents exit, entering the local environment; refer to 43 in FIG. 19, further discussed within THE DRAWINGS. Solid effluents such as ash, not leaving the Stack, are referenced to the generic system's boundary 44 in FIG. 19.

As used herein, the words "Boiler" or "Boiler Effluent" are defined as the region 35 in FIG. 19, or generically between the physical exit of the system's region 34 in FIG. 19 and entrance to its air pre-heater 36 in FIG. 19; see THE DRAWINGS.

Figure 20A:
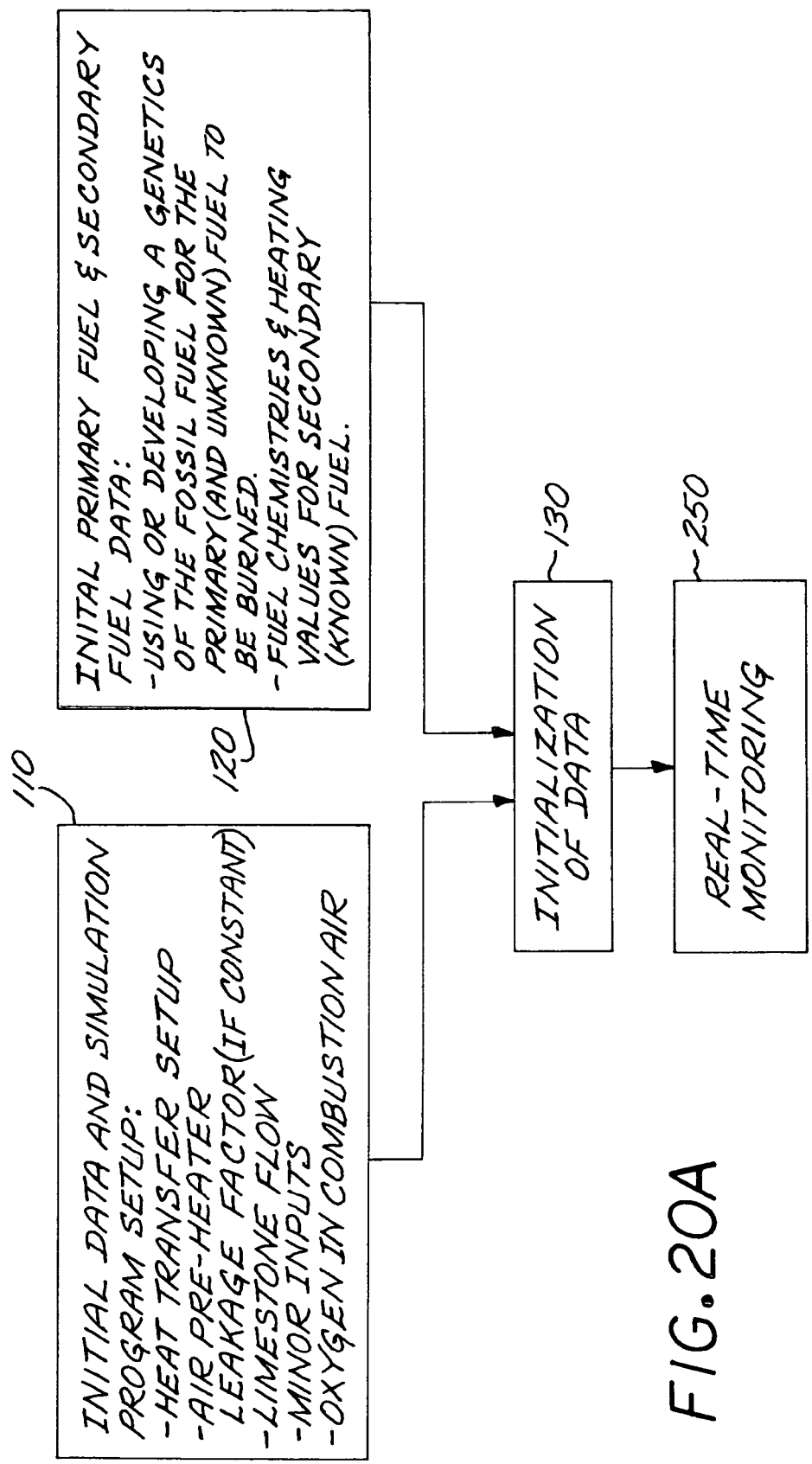
FIG. 20A, FIG. 20B and FIG. 20C is a block diagram of the general interactions and functions of The Input/Loss Method and supporting computer programs ERR-CALC, FUEL, EX-FOSS and HEATRATE used to implement this invention; herein collectively referred to as FIG. 20.

As used herein, the words "Fuel Iterations" are defined in conjunction with a detailed description of FIG. 20 found within THE DRAWINGS.

As used herein, the word "indicated" when used in the context of data originating from the thermal system is defined as the system's actual and uncorrected measurements of a physical process (e.g., pressure, temperature, mass flow, volumetric flow, density, and the like) whose accuracy or inaccuracy is not assumed. As examples, a system's "indicated plant fuel flow" or its "indicated plant limestone flow" denote system measurements the accuracy of which is unknown (they are "as-is", with no judgement applied). Such indicated measurements are said to be either correctable or not. If not correctable, it may be that the associated computed value from Input/Loss methods tracks the indicated value over time (the indicated not being corrected per se). In the case of indicated plant limestone flow when used as a Choice Operating Parameter ($\Lambda_6$), it is directly corrected as taught by this invention. In the case of indicated plant fuel flow when used as a System Effect Parameter, it may be shown that the computed fuel flow, $m_{AF}$, tracks the indicated plant fuel flow, $m_{AF-PLT}$.

Figure 3:
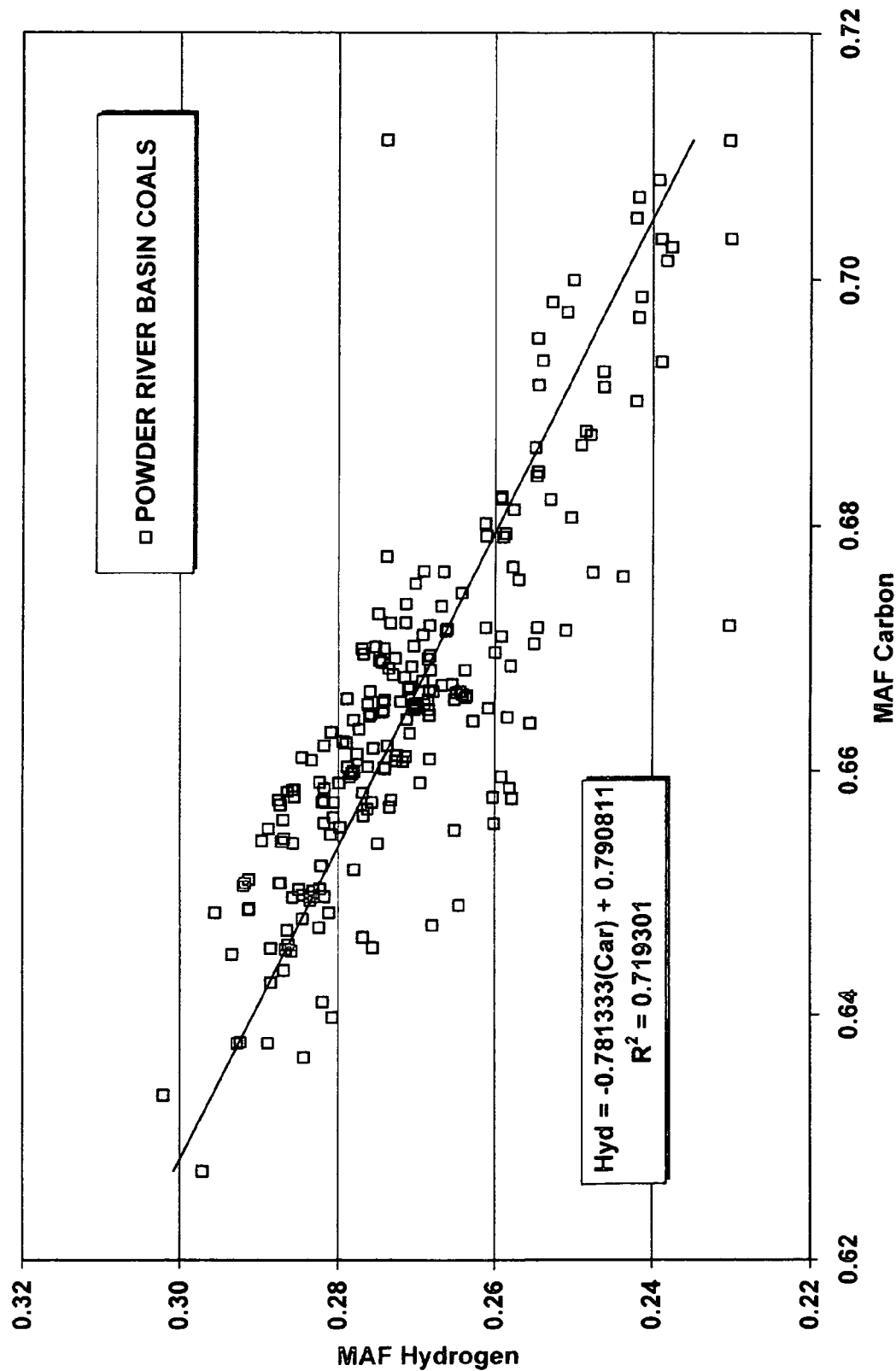
FIG. 3 (prior art) is a plot of MAF molar fuel diatomic hydrogen versus MAF molar fuel carbon for Powder River Basin coals following the teachings of '994, and as such it is considered prior art. The resultant $R^2$ value is 71.93%.

As used herein, the phrases "genetics of fossil fuels" or "genetics of the fossil fuel" are defined as the specific chemical patterns found common to certain fossil fuels. Genetics of fossil fuels results in elemental patterns numerically descriptive of molar relationships, for example the $CH_{c2}O_{c3}$ relationships as taught through TABLE 6. As defined, the term derives from the word "genesis" taken, in the context of this invention, as meaning to understand the chemical formation of fossil fuels. For the Preferred Embodiment, genetics of fossil fuels is based on "multi-variant analysis". Multi-variant analysis is defined as a combination of two or more elemental fuel constituents, multiplied by the same quantity, related mathematically to another elemental fuel constituent. The combination of two or more elemental fuel constituents may be dependent or independent quantities. Multi-variant analysis used herein comprise the following: combined MAF molar fuel carbon plus MAF molar fuel hydrogen as a function of MAF molar fuel oxygen; combined MAF molar fuel carbon plus MAF molar fuel oxygen as a function of MAF molar fuel hydrogen; or combined MAF molar fuel hydrogen plus MAF molar fuel oxygen as a function of MAF molar fuel carbon. Examples are found in Eqs.(61), (62), (63) and (74). Eq.(74) is formed when Eq.(71) is combined with Eq.(72) eliminating $L_{10}$. Note that these relationships employ diatomic hydrogen and diatomic oxygen, consistent with Eq.(29F), which is the Preferred Embodiment. Although the early discovery work anticipated specifying a molecular pattern using monatomic hydrogen and monatomic oxygen, both the monatomic and diatomic analyses produced essentially the same high Coefficients of Determination (if consistency developed). The diatomic is the Preferred Embodiment only since it is consistent with the combustion equation, Eq. (29F), thus eliminating conversion between different MAF bases. Also, there are other multi-variant analysis types which may be considered such as: combined MAF molar fuel carbon plus MAF molar fuel hydrogen plus MAF molar fuel sulfur as a function of MAF molar fuel oxygen; MAF molar fuel carbon less MAF molar fuel hydrogen as a function of MAF molar fuel oxygen; and so forth. In addition, the most accurate way to describe this invention is to recognize the mathematical significance of the teachings in the context of monitoring power plants. In this regard, fundamentally taught is a "closed-form solution" which allows resolution of fossil fuel chemistry based on Choice Operating Parameters. In the broadest mathematical sense, a set of equations is said to have a closed-form solution producing a unique answer if, when solving a given problem, adherence is made to: 1) the use of routine mathematical operations (i.e., =−×÷); and 2) the use of known functions. As broadly accepted in the mathematical community, a closed-form solution may not be reliant on iterative procedures, on limits, or on unusual functions. Simply put, by example, being provided a series of simultaneous liner equations, having n-equations and functions, with n-unknowns, with defined real coefficients, a set of unique answers will result; this is a closed-form solution and is what is being taught herein as applied to monitoring power plants. For this invention, the phrase "closed-form solution" is herein defined as comprising of a set of linear stoichiometric equations of the combustion process free of fossil fuel regression constants, and "known functionalities of the thermal system burning a fossil fuel". For the Preferred Embodiment, the set of stoichiometric equations of the combustion process are taught throughout this disclosure, being specifically applied in the section entitled "Determining Complete As-Fired Fuel Chemistry" (below). This section employs combined Eqs.(77), (79), (80) and (83), all free of fossil fuel regression constants. The phrase "known functionalities of the thermal system burning a fossil fuel" comprises all basic and immediate understandings of an in-situ (physical) thermal system, and its fossil fuel, without need for additional or extraordinary testing or analyses which lead to single-variant relationships; i.e., a priori functionalities. Examples of such basic and immediate understanding regards the thermal system include: whether Air Pre-Heaters are employed by the system (i.e., for consideration of air leakage); whether a Reheater is employed (i.e., for consideration of total working fluid energy flow); the identification of instrumentation and its placements (are Stack or Boiler $CO_2$ measurements made?, is an effluent $H_2O$ measurement made and where?, etc.); and the like. One important consequence of knowing the functionalities of the thermal system, is how to select a set of Choice Operating Parameters appropriate to the thermal system. For the Preferred Embodiment, basic and immediate understanding regards the fossil fuel comprises knowing the broad type of fuel used (e.g., its Rank as defined by ASTM D388), and associated data found in either TABLE 2, 3 or 4, and data found in TABLES 7 and 8. This data allows for closed-form solution; that is, employing combinations of Eqs.(61) through (63), (71) and (72). For the Preferred Embodiment, the data from these TABLES may be used a priori, in closed-form. Details are discussed in the section entitled "Determining Complete As-Fired Fuel Chemistry". Therefore, a closed-form solution contains the necessary and sufficient conditions for unique solution, that is: combinations of stoichiometric equations and known functionalities as needed, not dependent on iterative procedures. What are not considered known functionalities of the thermal system burning a fossil fuel are single-variant relationships such as hydrogen=ƒ(carbon) as taught in '994, being defined as a portion of "reference fuel characteristics" as they require additional laboratory testing. What is not considered a known functionality of the thermal system burning a fossil fuel, is the need to collect or use fuel samples for ultimate analyses, as such collection requires additional laboratory testing. As clearly seen in FIG. 1, FIG. 3 and FIG. 5 fuels described by '994 technology based on single-variant relationships require a posteriori examination. For example, this is the case: when preparing for a new installation; when different coal seams are encountered using the same Rank; when changes in fuel sourcing happen but within the same region, such as different regions within the Powder River Basin; and the like.

As used herein, the meaning of the words "using a genetics of the fossil fuel based on multi-variant analysis" is defined as using the information gathered from Eqs.(61), (62), (63), and (71) combined with (72), particular to a collection of fossil fuels of interest. Said information may be used to form one or more required equations used by a matrix solution to resolve fuel chemistry. Said data, or useable data, is found in TABLE 2, TABLE 3, TABLE 4, TABLE 7 and TABLE 8. This definition does not mean that all equations must be employed. For example, Eq.(72) after combining with Eq.(71) to form a re-ordered Eq.(74), is applied using the data found in TABLE 7 and TABLE 8; becoming equation #1 in the 5×5 matrix solution. See the section entitled DETERMINING THE COMPLETE AS-FIRED FUEL CHEMISTRY. Eq.(63) is applied using the data found in TABLE 4, re-ordered as Eq.(64); becoming equation #2 in the 5×5 matrix solution. In the 5×5 matrix solution there is no other information extracted from Eqs. (61), (62), (63), (71) or (72) which is required. The meaning of the words "developing a genetics of the fossil fuel based on multi-variant analysis" is defined as creating multi-variant relationships based on the general teachings of this invention, taken in the broadest interpretation of the inventive features discussed in this paragraph and elsewhere herein. For example, these teachings are not limited to multi-variant analysis involving only two elements; more than two may apply as would be applicable to equations of the form found in Eqs.(61), (62), (63) and (72).

As used herein, the meaning of the words "complete As-Fired fuel chemistry" is defined as comprising the following constituents of a fossil fuel: elemental carbon, elemental hydrogen, elemental oxygen, elemental sulfur, elemental nitrogen, mineral matter (ash), and water. It is understood by one skilled in the art that elemental hydrogen and elemental oxygen derive from the dry chemical make-up of the fossil fuel (water free) and are not influenced by the fuel's water content Often fuel water is termed "fuel moisture"; they mean the same. Fuel mineral matter is also termed "fuel ash"; they mean the same. Correctly stated, fuel ash is residue remaining after the combustion of a fossil fuel, commonly assumed to be the non-combustible mineral matter associated with the un-combusted fuel. The term "fuel ash" is commonly used in the industry, meaning mineral matter, and is employed herein. As used herein the terms "Ultimate Analysis" or "Ultimate Analyses" meaning multiple Ultimate Analysis, is defined as comprising the following constituents of a fossil fuel: elemental carbon, elemental hydrogen, elemental oxygen, elemental sulfur and elemental nitrogen. As strictly defined, an Ultimate Analysis is free of fuel gaseous components, free of fuel ash and free of fuel water; it truly represents Moisture-Ash-Gas-Free (MAGF) elemental constituents. For this disclosure, fuel gaseous components are not considered, they are considered however in '994, whose teachings of these terms, and other minor components of a fossil fuel, may be incorporated herein for expansion of the disclosure's methods by following the teachings found in '994. Note that an "As-Fired" condition refers to the actual fuel, with mineral matter and wet with water, in the state of being fired into the thermal system; that is, fuel 22 crossing the thermodynamic boundary 44 in FIG. 19.

As used herein, the words "operating a programmed computer" or "operating the programmed computer" are defined as the action encompassing either to directly operate a programmed computer, to cause the operation of a programmed computer, or to authorize the operation of a programmed computer at a facility controlled by the authorizer. In like manner, the word "calculating", for example in the context of "calculating a fuel calorific value" is defined as encompassing either to engage directly in the action of calculating, or to cause a calculating process through a programmed computer, or to authorize a calculating process through a programmed computer at a facility controlled by the authorizer.

As used herein, the words "calorific value" and "heating value" mean the same. As used herein, the words "gross calorific value" and "higher heating value" mean the same. As used herein, the words "net calorific value" and "lower heating value" mean the same.

As used herein, the words "$R^2$ value" or "$R^2$ values" mean the Coefficient of Determination as computed by the Excel computer program using linear regression.

As used herein, the meaning of the word "quantifying" in the context of "quantifying the operation of a thermal system" is taken in the usual dictionary sense, meaning "to determine or express the quantity of . . . "; for example, at a minimum what is being "quantified" is a complete As-Fired fuel chemistry.

System Stoichiometrics

Any study of the combustion of fossil fuels necessitates the formulation and use of a combustion equation. Combustion equations used by several Input/Loss methods are described in '994 by its designated Eq.(29), in '429 by its Eq.(19), in '877 by its Eq.(19-corr), in US2004/128111 by its Eq.(19BL). These combustion equations are cited to demonstrate the flexibility of the present invention to different situations. As examples: consideration of CaO as an ash constituent (termed $\alpha_{CaCO3}$), deriving from limestone found in the originating mineral matter is taught in '877 by its Eq.(19-corr); the study of black liquor fuel consisting of hydrocarbons and sodium compounds is taught in US2004/128111; and other variations are taught in the cited patents supporting The Input/Loss Method. This invention's methods are taught through a combustion equation defined by Eq.(29F) herein. Through Eq.(29F) stoichiometric terms become self-defined. Eq.(29F)'s nomenclature is unique in that brackets are used for clarity: for example, the expression "$x\alpha_2[H_2O]$" means the moles of fuel water/base, algebraically simply $x\alpha_2$; the expression "$d_{Act}[CO_2]$" means the effluent moles of carbon dioxide/base, algebraically simply $d_{Act}$; "$\beta b_A[H_2O]$" means the effluent moles of moisture found in the leakage air; etc. The stoichiometric base of Eq.(29F) is 100 moles of dry Stack gas (i.e., at the thermodynamic boundary).

$$x[\alpha_1[N_2] + \alpha_2[H_2O] + \alpha_3[O_2] + \alpha_4[C] + \quad (29F)$$
$$\alpha_5[H_2] + \alpha_6[S] + \alpha_{10}[ash]]_{As\text{-}Fired\ Fuel} +$$
$$b_Z[H_2O]_{In\text{-}Leakage} + [(1.0+\beta)(a[O_2] + a\varphi_{Act}[N_2] +$$
$$b_A[H_2O])]_{Air} + [(1.0+\gamma)b_{PLS}[(CaCO)_3]]_{As\text{-}Fired\ PLS} =$$
$$d_{Act}[CO_2] + g[O_2] + h[N_2] +$$
$$j[H_2O] + k_{Act}[SO_2]_{Effluent} + r[SO_2]_{Capture} +$$
$$[e_{Act}[CO] + f[H_2] + l[SO_3] + m[NO] +$$
$$p[N_2O] + q[NO_2] + t[C_{YP1}H_{ZP1}] +$$
$$u[C_{YP2}H_{ZP2}]]_{Minor\ Components} + x\alpha_{10}[ash] +$$
$$\sigma b_{PLS}[(CaSO)_4 \cdot zH_2O] +$$
$$[\{(1.0-\sigma+\gamma)b_{PLS}[CaO]]_{Excess\ PLS} + v[C_{Refuse}] +$$
$$w[C_{Reject}] + [\beta a[O_2] + \beta a\varphi_{Act}[N_2] + \beta b_A[H_2O]]_{Air\ Leakage}$$

Resolution of Eq.(29F) is had when all $n_i$ and $n_{ii}$ quantities have been determined. Minor component terms of Eq.(29F) are typically resolved either through direct measurement (e.g., for CO and NO), or assume zero values, or through obtained relationships. All minor components typically have only low parts-per-million concentrations and thus have little impact. Although non-traditional fuel components such as $\alpha_0[C_{YR}H_{ZR}]$, $\alpha_7[CO_2]$, $\alpha_8[CO]$ and $\alpha_9[H_2S]$ are not presented in Eq.(29F); treatment of such components is taught in '994 and whose teachings of these terms may be directly transferred. Note that the term $\alpha_0[C_{YR}H_{ZR}]$ represents a composite gaseous fuel which may be used for flame stability, as sometimes employed when firing with coal. As defined herein the principle unknown fuel constituents, resolved by this invention, include those indicated in Eq. (29F) as: $\alpha_1[N_2]$, $\alpha_2[H_2O]$, $\alpha_3[O_2]$, $\alpha_4[C]$, $\alpha_5[H_2]$, $\alpha_6[S]$ and $\alpha_{10}[ash]$. The minor effluents, $e_{Act}[CO]$, $f[H_2]$, $l[SO_3]$, $m[NO]$, $p[N_2O]$, $q[NO_2]$, $t[C_{YP1}H_{ZP1}]$ and $u[C_{YP2}H_{ZP2}]$ are presented for generalized teaching; their values are assumed to be constant or otherwise obtained. More specifically, many times effluent CO is measured, $NO_X$ is measured generically then divided into NO, $N_2O$ and $NO_2$ compounds based on estimation or periodic measurements. The unburned hydrocarbons $C_{YP1}H_{ZP1}$ and $C_{YP2}H_{ZP2}$ represent compounds which could be measured with hydrocarbon (combustibles) instrumentation, or otherwise obtained. The true importance and functionality of Eq.(29F) to The Input/Loss Method, or any other combustion equation used for any of the Input/Loss methods, lies in the fact that consistency of molar balances is required for successful system understanding, for conservation of mass flows and for resolution of fuel chemistry. For clarity the following major terms are associated with system stoichiometrics of Eq.(29F):

Total effluent (boundary) water=$J_{Act}$=$j+b_A\beta$
Boiler oxygen before air leakage (termed $g'_{Act}$)=$gR_{Act}$
Total effluent (boundary) oxygen=$G_{Act}$=$g+a\beta$
Total effluent (boundary) carbon dioxide=$d_{Act}$
Total effluents referenced to the boundary=$\Sigma n_i + \Sigma n_{ii} + \beta(a+a\varphi_{Act}+b_A)$
Total effluents before air leakage, referenced upstream of the air in-leakage=$R_{Act}\Sigma n_i + R_{Act}\Sigma n_{ii}$
Dry combustion air without air leakage referenced to the boundary=$(a+a\varphi_{Act})$
Wet combustion air without air leakage referenced to the boundary=$(a+a\varphi_{Act}+b_A)$
Dry air from air leakage found at the boundary=$\beta(a+a\varphi_{Act})$
Total in-flow of wet combustion air and wet air leakage found at the boundary=$(1.0+\beta)(a+a\varphi_{Act}+b_A)$.

Eq.(29F) describes at least three features of critical importance when determining fuel chemistry using one of the Input/Loss methods. The critical features include: 1) its ability to address air pre-heater leakage through application of the Air Pre-Heater Leakage Factor, $R_{Act}$, and through the Air Pre-Heater Dilution Factor, $\beta$; 2) the ability to describe effluent concentrations on either side of the air pre-heater, again through application of $R_{Act}$; and 3) the use of an explicit $\phi_{Act}$ term allowing for variable $O_2$ concentration in the system's local combustion air. Air pre-heater leakage dilutes all combustion effluents with moist air from the local environment, thus all important effluents $H_2O$, $CO_2$ and $O_2$ used for this invention are altered. Furthermore, many times, although not always, a power plant's more precise effluent measurements may be found on the air pre-heater's inlet (economizer outlet or Boiler), and not at the air heater outlet (or Stack); refer to FIG. 19. Although most environmental regulations require effluent measurements at the system's boundary, translation between the air heater inlet to outlet measurements is many times essential. Eq.(29F) allows for such translation through the $R_{Act}$ term, defined above such that 100 moles of dry gas are computed both at the upstream and downstream locations of the air pre-heater; see "Boiler" of FIG. 19. Thus effluents may be used by the present invention either upstream or downstream of the air pre-heater; refer to the $G_{Act}$ and $J_{Act}$ terms defined above, allowing conversion between measurements with and without air leakage. For example, combustion gas conditions for oxygen and water upstream of the air pre-heater and after exiting the heat exchanger/combustion region, see FIG. 19, would employ the terms: $gR_{Act}$ and $jR_{Act}$. That is, one would actually measure a $gR_{Act}$ moles of dry $O_2$ upstream of the air pre-heater and after exiting the heat exchanger/combustion region as based on 100 moles of dry gas found at that location. Combustion gases downstream of the air pre-heater typically exit the system to the environment (i.e., Stack), in other words the gaseous effluent boundary of the system (100 moles of dry gas at the Stack includes air leakage). If limestone is injected into the combustion process to control effluent $SO_2$ it will create additional effluent $CO_2$; further, it could decrease the effluent $H_2O$ if the sulfate product is matrixed with water, $CaSO_4 \cdot zH_2O$. Thus such effects must be considered. Of course $CO_2$, $H_2O$ and $O_2$ are three important effluents to the present invention. In addition to the basic stoichiometrics afforded, Eq.(29F) allows numerous and obvious determinations of molar and mass ratios.

Based on these teachings, the following further explains the importance of the Air Pre-Heater Leakage Factor, $R_{Act}$, and the Air Pre-Heater Dilution Factor, $\beta$, their definitions and developments and use. Consider that air in-leakage associated with a fossil-fired system, and as commonly associated with in-leakage at the system's air pre-heater, is defined by the American Society of Mechanical Engineers' Performance Test Code 4.3 (1974) as the mass of moist air leakage divided by the mass of wet combustion gas entering the air pre-heater. The wet combustion gas is taken at the gas inlet of the air pre-heater (i.e., Boiler, or economizer outlet before the air pre-heater). That is, as defined herein using Eq.(29F) nomenclature, noting that 100 moles of dry gas is the bases at the Boiler, is given by:

$$\text{Wet APH Leakage} \equiv \frac{R_{Act}\beta(a + a\varphi_{Act} + b_A)N_{MoistAir}}{(100 + R_{Act}j)N_{WetGas}} \quad (20)$$

where, as defined above:

$R_{Act}$=(Moles of $CO_2$ entering the air pre-heater)/(Moles of $CO_2$ leaving the air pre-heater). The expression for $R_{Act}$ is equivalent to (Moles of Boiler $CO_2$) divided by (Moles of Stack $CO_2$), noting that each of these would-be measurements is referenced to 100 moles of dry gas. The Air Pre-Heater Dilution Factor is then developed by performing a total dry gaseous effluent molar balance at the Stack, see FIG. 19:

100 moles dry gaseous effluent at Stack=$\Sigma n_i$+ $\beta(a+a\phi_{Act})$ (21)

and then solving for $\beta$: $\beta=(100-\Sigma n_i)/(a+a\phi_{Act})$. The stoichiometric base of Eq.(29F) implies that 100 moles of dry gaseous effluent upstream of the air pre-heater (Boiler) is given by $R_{Act}\Sigma n_i$ (thus $\Sigma n_i=100/R_{Act}$); therefore:

$$\beta = (100 - 100/R_{Act})/[a(1.0 + \varphi_{Act})] \quad (22)$$
$$\equiv 100(R_{Act} - 1.0)/[R_{Act}a(1.0 + \varphi_{Act})].$$

If, instead of obtaining the ratio of $CO_2$ across the air pre-heater, the ratio of $O_2$ is obtained, the following may then be developed:

$R'_{Act}$=(Moles of $O_2$ entering the air pre-heater)/ (Moles of $O_2$ leaving the air pre-heater).

where, converting from $R'_{Act}$ to $R_{Act}$, using algebraic manipulations results in, when measuring Stack $O_2$ (the term $G_{Act}$):

$$R_{Act} \equiv \frac{100 - R'_{Act}G_{Act}(1.0 + \varphi_{Act})}{100 - G_{Act}(1.0 + \varphi_{act})} \quad (23)$$

If measuring Boiler $O_2$ (for Eq.(24) termed $g'_{Act}$):

$$R_{Act} \equiv \frac{100R'_{Act} - R'_{Act}g'_{Act}(1.0 + \varphi_{Act})}{100R'_{Act} - g'_{Act}(1.0 + \varphi_{Act})} \quad (24)$$

There are, of course, a number of variations to these formulations, such as employing 100 moles of wet effluents at the Stack, thus replacing Eq.(21) with:

100 moles wet effluent at Stack=$(\Sigma n_i+j)$+ $\beta(a+a\phi_{Act}+b_A)$ (25)

or using an oxygen base for the wet effluents at the Stack, thus: $(\Sigma n_i+J_{Act})/a+\beta(1.0+\phi_{Act})$; or using a combustion equation which is based on a mole of fuel carbon $(x\alpha_4)$; etc. What is important to this invention, important to The Input/Loss Method, and important to any of the Input/Loss methods, is that the Air Pre-Heater Leakage Factor ($R_{Act}$) allows gaseous measurements to be employed on either side of the system air in-leakage. Typically, but not always, $O_2$ is measured in the combustion gas stream inlet to the air pre-heater (Boiler), while $CO_2$ is measured at the Stack (downstream from the air pre-heater).

After establishing system stoichiometrics, the next stage of the process involves the recognition that because a given fuel has an unique, although unknown, chemical composition, when burned it will yield unique concentrations of principle effluents $CO_2$, $H_2O$, $O_2$, and $SO_2$ (if fuel sulfur is present). The gaseous effluent concentrations are used to compute the fuel chemistry, with this chemistry fuel calorific value and boiler efficiency are then computed, in turn this information allows the computation of fuel flow and system efficiency. The gaseous effluents from any fossil combustion process are $N_2$, $CO_2$, $H_2O$, $O_2$ and $SO_2$ (if fuel sulfur is present). $H_2O$, when effluent from combustion, is in its superheated phase, thus acting as a gas. The source of $N_2$ is principally the air used to burn the fuel and has little chemical reactiveness, thus its sensitivity to the fuel's chemical composition is not significant. The use of a measured effluent $N_2$ is not practical, nor can add to the matrix solution, given that fuel nitrogen is generally one of the smallest components of a fossil fuel, effluent $N_2$ being the largest combustion product, thus even the slightest measurement error would have an enormous influence on computed fuel chemistry. $SO_2$ effluent concentrations are generally in the parts per million thus its impact may have minor importance on the global solution, but not always and thus may be treated seperately as taught by Eq.(79), or combined as taught by Eqs.(80) or (83).

As an intrinsic chemical relationship, the relative concentrations of carbon ($\alpha_4$), hydrogen ($\alpha_5$) and oxygen ($\alpha_3$) found in any fossil fuel will have significant impact on the relative concentrations of $CO_2$, $H_2O$ and $O_2$ found in the effluent. The concept of involving fuel oxygen in this statement is fundamentally different from '994. Considered when developing this invention was an "Oxy-Hydrocarbon" (OHC) approach to stoichiometrics—not a simple "hydrocarbon" approach—and this being possible only through multi-variant analysis of fossil fuels (explained below). The $CO_2$, $H_2O$ and $O_2$ effluents will be influenced by the following: $O_2$ used to burn the fuel (i.e., the Air/Fuel ratio); fuel water, $\alpha_2$; in-leakage of water including tube leaks ($b_Z$); and water in the combustion air ($b_A$). This implies that the molar fractions of $CO_2$, $H_2O$ and $O_2$ present in the effluent (the system's boundary, i.e., data at the Stack or data translated from air pre-heater inlet to the Stack) must be unique relative to the supplied fuel and supplied combustion air.

The following elemental molar balances may be derived from the combustion equation, Eq.(29F). The $\Gamma_k$ expressions are simply convenient groupings of quantities, principally comprising measured effluents (known values) which have the greatest influence on the individual fuel elements of interest. Many coal-fired units use supplementary firing with gaseous fuel or fuel oil. Such minor fuel terms, e.g., composite gaseous fuels described by $\alpha_0[C_{YR}H_{ZR}]$, not shown in Eq.(29F) but taught in '994, may be included within $\Gamma_k$ expressions and are multiplied, initially, by an estimated fuel moles, $x_{MAF}$. Such minor terms may be quickly resolved when converging on $x_{MAF}$. Given these groupings, the $\Gamma_k$ expressions of Eqs.(36) through (41), with solution of the moles of combustion oxygen (the term "a") as discussed below, may be treated as known quantities. The elemental wet fuel components are considered unknowns, as are the fuel moles; the unknowns include the following: $\alpha_1$, $\alpha_2$, $\alpha_3$, $\alpha_4$, $\alpha_5$, $\alpha_6$, $\alpha_{10}$ and "x" in Eq.(29F).

$$x\alpha_1 = \Gamma_{N2} - a\varphi_{Act} \quad (30)$$

$$x(\alpha_5 + \alpha_2) = \Gamma_{H2O} \quad (31)$$

$$x(\alpha_3 + \alpha_2/2) = \Gamma_{O2} \quad (32)$$

-continued $$x\alpha_4 = \Gamma_{CO2} \quad (33)$$

$$x\alpha_6 = \Gamma_{SO2} \quad (34)$$

where:

$$\Gamma_{N2} = 100 - (d_{Act} + e_{Act} + f + G_{Act} + k_{Act} + l + m/2 + q/2 + t + u) - 100\varphi_{Act}(R_{Act} - 1.0)/[R_{Act}(\varphi_{Act} + 1.0)] \quad (36)$$

$$\Gamma_{H2O} = (J_{Act} - b_A\beta) + f + (ZP1)t/2 + (ZP2)u/2 - b_Z - b_A + b_{PLS}\sigma z \quad (37)$$

$$\Gamma_{O2} = \quad (38)$$
$$d_{Act} + e_{Act}/2 + (G_{Act} - a\beta) + (J_{Act} - b_A\beta)/2 + m/2 + p/2 + q - a - b_A/2 - b_Z/2 + k_{Act} + 3l/2 + r + (3\sigma - 2 - 2\gamma + \sigma z)b_{PLS}/2$$

$$\Gamma_{OHS} = d_{Act} + e_{Act}/2 + (G_{Act} - a\beta) + (J_{Act} - b_A\beta)/2 + m/2 + p/2 + q - a - b_A/2 - b_Z/2 \quad (39)$$

$$\Gamma_{CO2} = d_{Act} + e_{Act} + (YP1)t + (YP2)u + v + w - (1.0 + \gamma)b_{PLS} \quad (40)$$

$$\Gamma_{SO2} = (\sigma b_{PLS} + k_{Act}/\Gamma_{ESP})[1.0 + \Gamma_{SO3}/(1.0 - \Gamma_{SO3})] \quad (41)$$

In these relationships the subscript "Act" means an effluent measurement or assumption (an "actual" value). The term $J_{Act}$ in Eqs.(37), (38) and (39) relating to the moles of effluent $H_2O$ could be input as a constant value or measured or otherwise obtained. All other values in Eqs.(36) through (41) are either measured, evaluated explicitly based on input data, internal models and/or have minor import but are carried in the formulations for teaching consistency of stoichiometrics.

Eq.(29F) teaches that fuel sulfur is allowed to produce both $SO_2$ and $SO_3$. For the $SO_2$ produced from fuel sulfur a portion is allowed to be captured by effluent ash or converted by limestone. The following relationships explain, resulting in Eq.(41); refer to the DEFINITIONS section above for meanings of the variables employed in Eq.(42). From a simple sulfur balance using Eq.(29F):

$$\Gamma_{SO2} = x\alpha_6 = k_{Act} + l + r + \sigma b_{PLS} \quad (42)$$

where:

$$x\alpha_6 = k_F + l$$
$$k_F = k_{Act} + r + \sigma b_{PLS}$$
$$k_{Act} + r = k_{Act}/\Gamma_{ESP}$$
$$l = k_F\Gamma_{SO3}/(1.0 - \Gamma_{SO3})$$
$$= (\sigma b_{PLS} + k_{Act}/\Gamma_{ESP})\Gamma_{SO3}/(1.0 - \Gamma_{SO3})$$

Therefore by reducing Eq.(42) using the above relationships, Eq.(41) results; this equation employs either known quantities, or measurable quantities or quantities which may be reasonably estimated knowing the functionalities of the thermal system. It will become apparent that prior methods as taught in '994, where fuel sulfur may have been assumed constant, are not adequate for the present invention. When sulfur is present in the fuel, the genetics of the fossil fuel allow its explicit computation.

As a group, these relationships are of critical importance for understanding The Input/Loss Method. If fuel chemistry is to be resolved, thus calorific value, boiler efficiency, accurate fuel flow and system efficiency, then stoichiometric relationships generally represented by Eqs.(30) to (41) must be resolved. These equations are not unique in their grouping of terms; further reductions and/or complexities are certainty possible. The grouping of terms adopted here principally follows from the right-side of Eq.(29F).

Eqs.(30) through (34) yield five equations with nine unknowns. For this situation, unknowns include $\alpha_1$ through $\alpha_6$, $\alpha_{10}$, and the terms "a" and "x". The term "x" is a convenience term and could be divided through changing the base of Eq.(29F) to unity moles of fuel, thus eliminating use of $x\alpha_j$ terms comprising two unknowns. However, if done, then the effluent's base becomes per mole of fuel, e.g., thus an effluent term $d_{Act}/x$, adding a different complexity involving the normalization of effluent measurements. Although the requirement $\Sigma\alpha_{MAF-j}=1.00$ is a convenience, it affords another, and viable, equation. By making a molar nitrogen balance, and assuming 100 moles of dry gaseous effluent at the boundary, the "a" quantity (moles of combustion oxygen) may be resolved independent of Eq.(30), thus reducing the unknowns; detailed below. Again, the entire combustion equation, Eq.(29F), could be divided through by $\alpha_4$, or $x\alpha_4$, thus setting a carbon base. Effluent $N_2$ could be resolved by difference assuming 100 moles of gaseous effluent ($CO_2$, $H_2O$, $O_2$, $SO_2$, the minor pollutants being measured or assumed), or $N_2$ could be measured directly. However, using effluent $N_2$ to resolve fuel nitrogen, $\alpha_1$, is not practical given fuel nitrogen is typically a minor fuel constituent (as is sulfur), any error made in measuring effluent $N_2$ would greatly effect all fuel constituents; it is not a practical equation. Or, further still, by assuming constant values for fuel nitrogen and sulfur, $\alpha_1$ and $\alpha_6$, with resolution of "a", and say: $\alpha_3=1.0-\Sigma\alpha_{MAF-j}$, $j\neq 3$, the system is reduced to three equations with four unknowns; these include Eqs.(31) through (33), with $\alpha_2$, $\alpha_4$, $\alpha_5$ and "x". As another example, if $\alpha_3$ is assumed constant, then the combined Eqs.(31) and (32) (with cancellation of $x\alpha_2$) represents one equation with two unknowns, "x" and $\alpha_5$. And, of course, further reductions and manipulations of unknowns and equations is entirely possible. However, the point is that close examination of the physical problem of combustion stoichiometrics, in which fuel chemistry is to be determined from effluents, indicates that the mathematical system has more unknowns than equations. In summary, these manipulations are discussed to emphasize that, as taught by this invention, a new approach must be provided which provides, not mere simple correlations of hydrogen versus carbon as was done in '994, but rather establishing the genetics of the fossil fuel. '994 solution employed, that was believed to be intrinsic chemical relationships, correlation constants within the resolution of the combustion equation (i.e., single-variant correlation constants appear within stoichiometric equations). Although '994 employed single-variant correlations based on MAF molar concentrations, single-variant correlations based on weight concentrations are commonly found throughout the fossil fuel literature.

To address the solution problem, whereas the '994 solution was achieved through relationships found between MAF molar fuel hydrogen and MAF molar fuel carbon (and representing a particular mined fuel), the present invention recognizes the genetics of the fossil fuel and employs its findings to achieve a matrix solution. The Preferred Embodiment does not require that the minor fuel constituents be assumed constant, they may be measured quantities (e.g., effluent $SO_2$, effluent CO, effluent $NO_X$, etc.) and/or otherwise obtained. Further, as will become apparent, the Preferred Embodiment allows use of multidimensional minimization techniques taught in '877 which addresses instrumentation errors.

Returning to the solution problem as posed by Eq.(29F), the problem is solved, in part, by reducing $\alpha_j$ quantities to a MAF molar basis, eliminating the influence of the two components not chemically involved with the Oxy-Hydrocarbon fuel per se, water and mineral matter (ash). Before addressing the genetics of fossil fuels, the following teaches how fuel water and fuel ash are resolved, the $\alpha_{MAF-i}$ terms required are then fully taught in subsequent sections. MAF molar fuel water is resolved by adding Eqs.(31) and (32), then substituting $x_{MAF}$ for $\Gamma_{CO2}/\alpha_{MAF-4}$; see Eq.(92):

$$\alpha_{MAF-2}=2[\alpha_{MAF-4}(\Gamma_{H2O}+\Gamma_{O2})/\Gamma_{CO2}-\alpha_{MAF-5}-\alpha_{MAF-3}]/3 \quad (42)$$

To determine fuel ash using explicit relationships requires examination of the total system. The only system effect of fuel ash is as a pure dilutive or concentrative influence on fuel, and of course on the fuel's calorific value. From a qualitative viewpoint, as fuel ash increases at the expense of carbon (for example), the amount of combustion air required to produce the same effluent $O_2$ actually increases given that more fuel is required to achieve the same energy flow to the working fluid given less combustibles in the fuel; in large commercial power plants the coal is borne by combustion air to the furnace region. Given a decreasing calorific value (higher ash) increased fuel flow is required to meet the same energy flow to the working fluid. Thus an ideal system parameter for such sensitivities, which is routinely measured at fossil-fueled systems, is the indicated Air/Fuel ratio. Generally such sensitivities are reasonable, a 10 percent increase in ash for a common coal will cause a linear effect in the Air/Fuel ratio. The wet, mass base, Air/Fuel ratio (termed $AF_{Act}$), a calculational quantity, is developed as follows:

$$AF_{Act}=(m_{Air}+m_{Moisture})/m_{AF} \quad (48A)$$

$$AF_{Act}=(1+\beta)[(a+a\varphi_{Act})N_{Air}+b_AN_{H2O}]/(xN_{AF}) \quad (48B)$$

Expanding the term $xN_{AF}$ in Eq.(48B), noting that $N_{AF}$ relates to the wet As-Fired fuel (i.e., j=1,2,3,4,5,6,10):

$$xN_{AF}=x(\Sigma_{j=1-6}N_j\alpha_j+N_{10}\alpha_{10}) \quad (49)$$

and then employing the following definitions of MAF fuel moles and fuel constituents:

$$x_{MAF}\equiv x/(1.0+\alpha_{MAF-2}+\alpha_{MAF-10}) \quad (50)$$

$$\alpha_{MAF-j}\equiv\alpha_j(1.0+\alpha_{MAF-2}+\alpha_{MAF-10}) \quad (51)$$

allows substitution of Eqs.(50) and (51) into Eq.(49) for x and $\alpha_j$, cancelling the term $(1.0+\alpha_{MAF-2}+\alpha_{MAF-10})$ as intended, and then substituting into Eq.(48B) yields a solvable form:

$$xN_{AF}=x_{MAF}(\Sigma_{j=1-6}N_j\alpha_{MAF-j}+N_{10}\alpha_{MAF-10}) \quad (52)$$

$$AF_{Act}=(1.0+\beta)[(a+a\varphi_{Act})N_{Air}+b_AN_{H2O}]/[x_{MAF}(\Sigma_{j=1-6}N_j\alpha_{MAF-j}+N_{10}\alpha_{MAF-10})] \quad (53)$$

Simplifying Eq.(53) and solving for MAF fuel ash, $\alpha_{MAF-10}$, yields the following results. Note in Eq.(54) that a normalized Air/Fuel ratio is used, becoming $AF_{Act}$, normalized to indicated plant data, defined by Eq.(57). $x_{MAF}$ is substituted using Eq.(56).

$$\alpha_{MAF-10}=[\Gamma_{Ash}\alpha_{MAF-4}/(\Gamma_{CO2}N_{10})]-\Sigma_{j=1-6}N_j\alpha_{MAF-j}/N_{10} \quad (54)$$

$$\text{where: } \Gamma_{Ash}\equiv(1.0+\beta)[(a+a\varphi_{Act})N_{Air}+b_AN_{H2O}]/AF_{Act} \quad (55)$$

$$x_{MAF}=\Gamma_{CO2}/\alpha_{MAF-4} \quad (56)$$

-continued $$AF_{Act} \equiv AF_{input}(AF_{REF1}/AF_{REF2}) \quad (57)$$

$$a = (\Gamma_{N2} - x_{MAF}\alpha_{MAF-1})/\varphi_{Act} \quad (58)$$

The variable $AF_{input}$ is the wet Air/Fuel ratio from the system's data collection device (an indicated value); the ratio $(AF_{Ref1}/AF_{Ref2})$ is used to scale $AF_{input}$. The value of $N_{10}$ in Eq.(54) is input as a constant, or fitted as a function of $\alpha_{MAF-10}$ (thus solving a quadratic equation), or fitted as a function of $HHV_{MAF}$. Note that a system's indicated plant fuel flow measurement could obviously be used in place of $AF_{Act}$, applying similar techniques as demonstrated in determining $\alpha_{MAF-10}$. However, use of an $AF_{Act}$ variable is preferred since it integrally involves effluent and combustion air terms (through $\Gamma_{CO2}$, $\Gamma_{N2}$ and $\Gamma_{Ash}$), and thus through such dependencies allows error analysis techniques to be operational and practical. It is noteworthy that the explicit procedure of determining fuel ash, and through use of the term $(1.0+\alpha_{MAF-2}+\alpha_{MAF-10})$ of Eqs.(50) and (51), allows any errors made in fuel water, $\alpha_{MAF-2}$, to be off-set by fuel ash, $\alpha_{MAF-10}$. This must occur since any given quantity $x\alpha_j$ (wet-base) must be equivalent to $x_{MAF}\alpha_{MAF-j}$ (MAF-base); if not, such wet to MAF conversions would numerically cause inconsistencies in the computed Air/Fuel ratio.

In summary, MAF fuel ash, $\alpha_{MAF-10}$, may be determined from the explicit solution taught by Eq.(54). By "explicit solution" is meant that only independent (known) variables appear on the right hand side of an equation, including Eq.(54), the dependent term on the left (e.g., the $\alpha_{MAF-10}$ term). However, if the typical fossil fuel has no, little or essentially constant fuel ash, then $\alpha_{MAF-10}$ may be held constant, including zero. Further, it has been found that for certain lignite fuels, fuel ash may be determined by knowing, or estimating, MAF calorific value. For Greek lignite and lignite A, the following has been found broadly descriptive:

$$\alpha_{MAF-10}=0.4534-1.5199\times10^{-5}HHV_{MAF-EST}; \text{ for kJ/kg} \quad (60A)$$

$$\alpha_{MAF-10}=0.4534-3.5352\times10^{-5}HHV_{MAF-EST}; \text{ for Btu/lbm} \quad (60B)$$

The estimated MAF calorific value, $HHV_{MAF-EST}$, may be reasonably constant especially for the poorer fuels, eliminating iterative procedures. On the other hand, the MAF molar fuel ash value for the poorer quality fuels has been found to be remarkably constant. In addition, as taught in '994, fuel ash instruments are available which determine on a dry basis the concentration of fuel ash. Thus a fuel ash concentration may be selected from the group consisting of: a constant value of fuel ash, a predictable value of fuel ash, a measured value of fuel ash determined from a fuel ash instrument and a value of fuel ash determined from explicit solution, as an obtained fuel ash concentration. The Preferred Embodiment is to determine MAF molar fuel ash from the explicit solution, Eq.(54). If however data required for Eq.(54) is missing, or fuel ash is not sufficiently variable, then the reasonable Preferred Embodiment is to hold MAF molar fuel ash constant.

As taught in the above three paragraphs, fuel water and fuel ash may be explicitly determined provided the MAF fuel chemistry is known, that is known $\alpha_{MAF-1}$, $\alpha_{MAF-3}$, $\alpha_{MAF-4}$, $\alpha_{MAF-5}$ and $\alpha_{MAF-6}$. Fuel water is dependent on $\alpha_{MAF-4}$, $\alpha_{MAF-5}$ and $\alpha_{MAF-3}$. Fuel ash, if determined using Eq.(54), is dependent on all fuel constituents less ash, including $\alpha_{MAF-2}$ of Eq.(42), "a" of Eq.(58), $x_{MAF}$, etc. as indicated. The following section teaches the genetics of fossil fuels, through which the complete fuel chemistry is resolved. Note that if the minor fuel constituents of sulfur, nitrogen and ash can be assumed constant (including zero), then the matrix solution need only consider MAF molar fuel oxygen, carbon and hydrogen; thus an Oxy-Hydrocarbon understanding of the fuel.

Genetics of Fossil Fuels

The teachings of '994 relied on simple single-variant correlations to provide missing equations. As discussed above, single-variant correlations have been shown, for many important fuels, as not being adequate. What was discovered using Irish peat data (having significant fuel oxygen), was that multi-variant analysis not only dramatically improved $R^2$ values, but improved $R^2$ values to the point that a base understanding of the genetics of fossil fuels is obtained. What was discovered was that the following multi-variant relationships have a profound ability to describe fossil fuels with unheard of accuracy; an accuracy which addresses the very genetics of fossil fuels.

$$\alpha_{MAF-4} + \alpha_{MAF-5} = J_{OHC1} + K_{OHC1}\alpha_{MAF-3}$$

$$\alpha_{MAF-4} + \alpha_{MAF-3} = J_{OHC2} + K_{OHC2}\alpha_{MAF-5}$$

$$\alpha_{MAF-5} + \alpha_{MAF-3} = J_{OHC3} + K_{OHC3}\alpha_{MAF-4}$$

Figure 2:
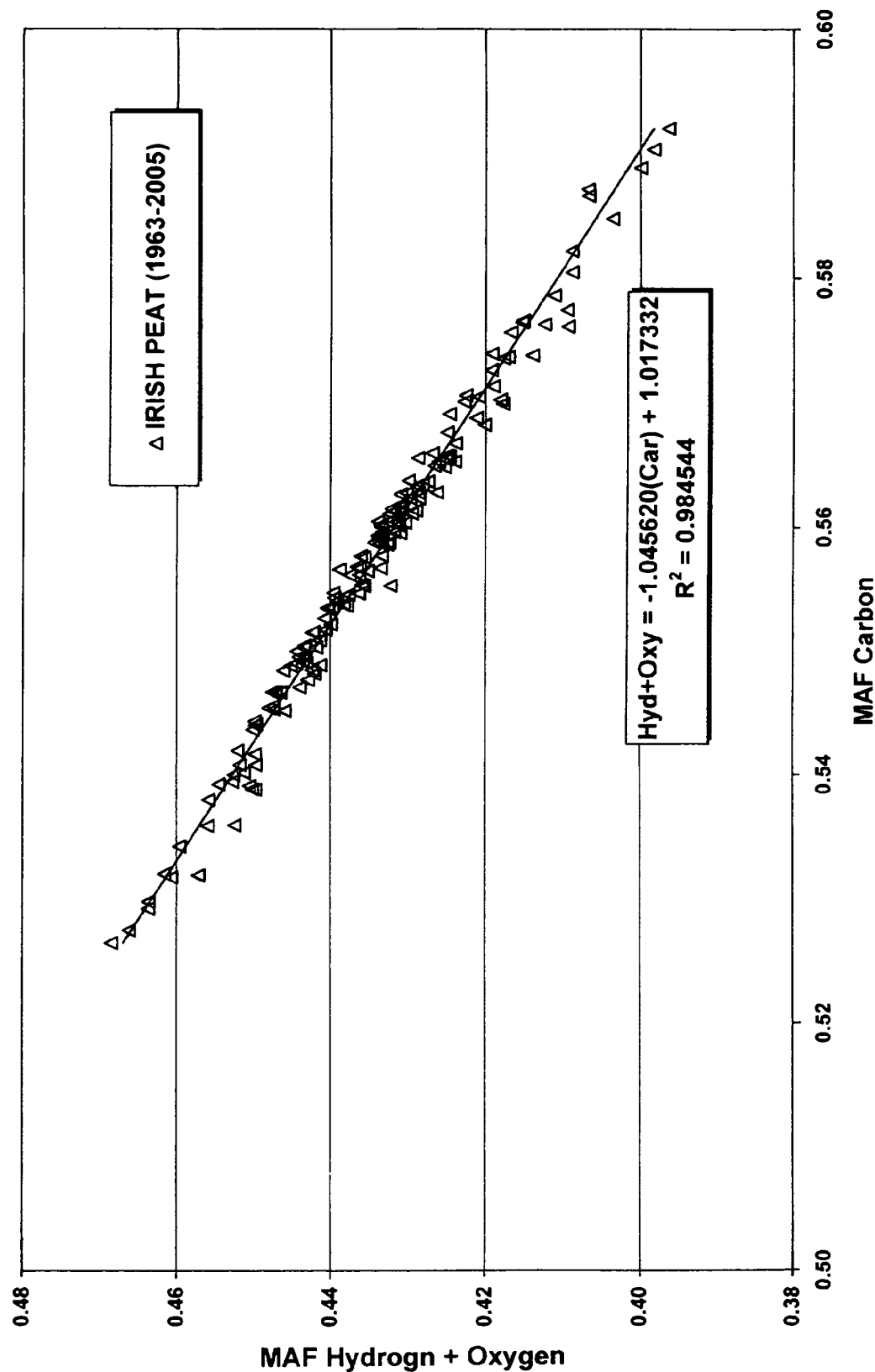
FIG. 2 is a plot of MAF molar fuel diatomic hydrogen plus MAF molar fuel diatomic oxygen versus MAF molar fuel carbon for Irish peat following the teachings herein, using the same Ultimate Analysis data as was used for FIG. 1. The resultant $R^2$ value is 98.45%. Refer to TABLE 4 for functionalities.
Figure 4:
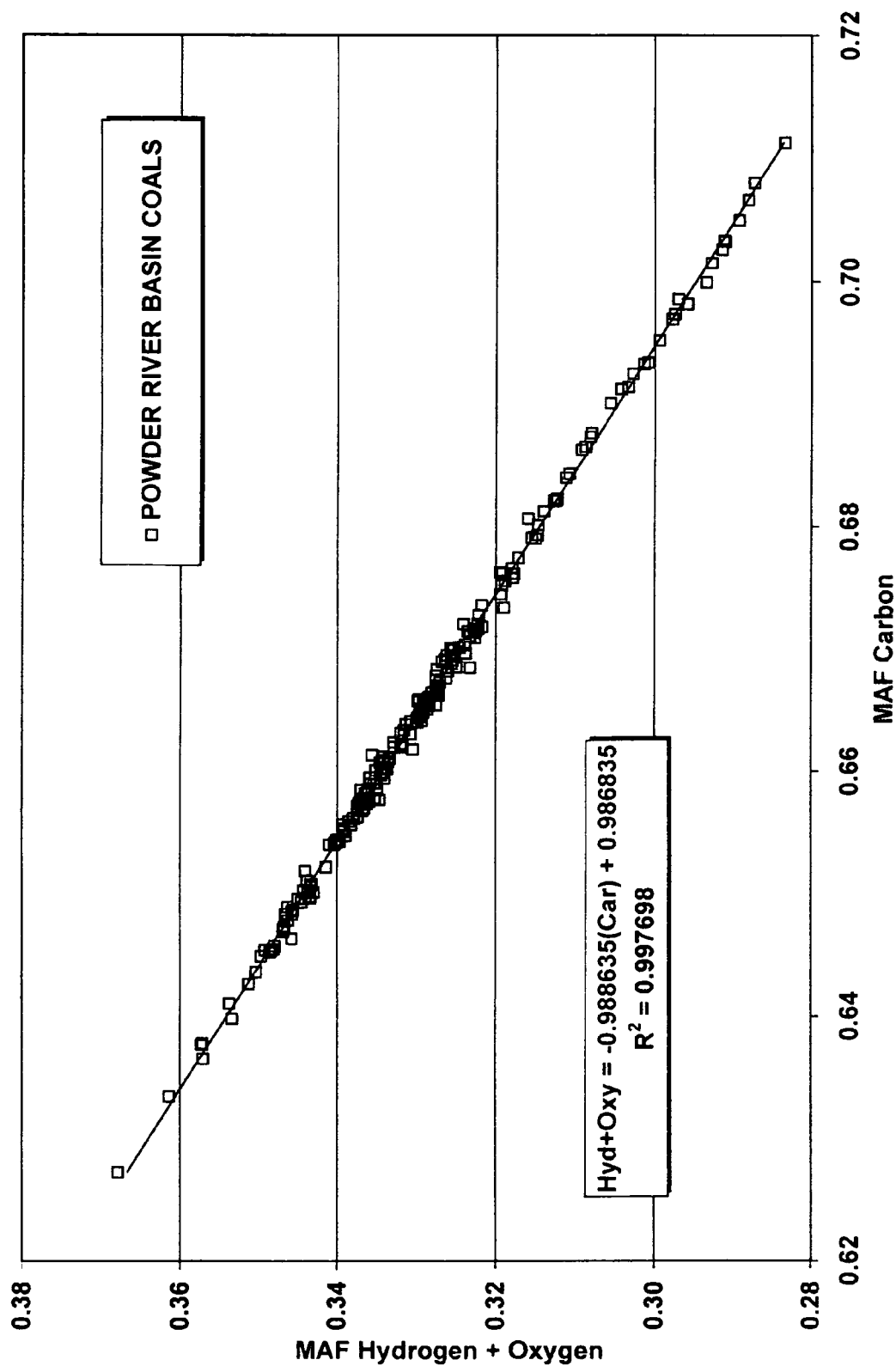
FIG. 4 is a plot of MAF molar fuel diatomic hydrogen plus MAF molar fuel diatomic oxygen versus MAF molar fuel carbon for Powder River Basin coals following the teachings herein, using the same Ultimate Analysis data as was used for FIG. 3. The resultant $R^2$ value is 99.77%. Refer to TABLE 4 for functionalities.

In these relationships, fuel hydrogen is taken in the diatomic form ($H_2$), as is fuel oxygen ($O_2$); as $\alpha_{MAF-5}$ and $\alpha_{MAF-3}$ result from Eq.(29F). This assumption, versus the monatomic, does not affect the outcome. The predictability of Eq.(63) versus '994 technology is best observed by comparing the Irish peat of FIG. 1 to FIG. 2 results in improving $R^2$ value from 65.90% to 98.45%. Comparing Powder River Basin coals of FIG. 3 to FIG. 4 results in improving $R^2$ value from 71.93% to 99.77%. Comparing High Seas and similar high volatile coals of FIG. 5 to FIG. 6 results in improving $R^2$ value from 81.77% to 99.77%. Note that the Irish peat data was obtained from laboratory analyses taken over 42 years; with a greater consistency of laboratory procedures, it is reasonable to assume that the $R^2$ value 98.45% for FIG. 2 would approach those found for FIG. 4 and FIG. 6. Although the use of multi-variant analysis may appear to be a simple extension of a single-variant approach ('994), there was nothing found in the fossil fuel literature which would suggest multi-variant analysis; and nothing found in the literature which would suggest that resultant multi-variant relationships, e.g., Eqs.(64) or (74), may be used to provide missing equations for matrix solutions to fuel chemistry.

Figure 5:
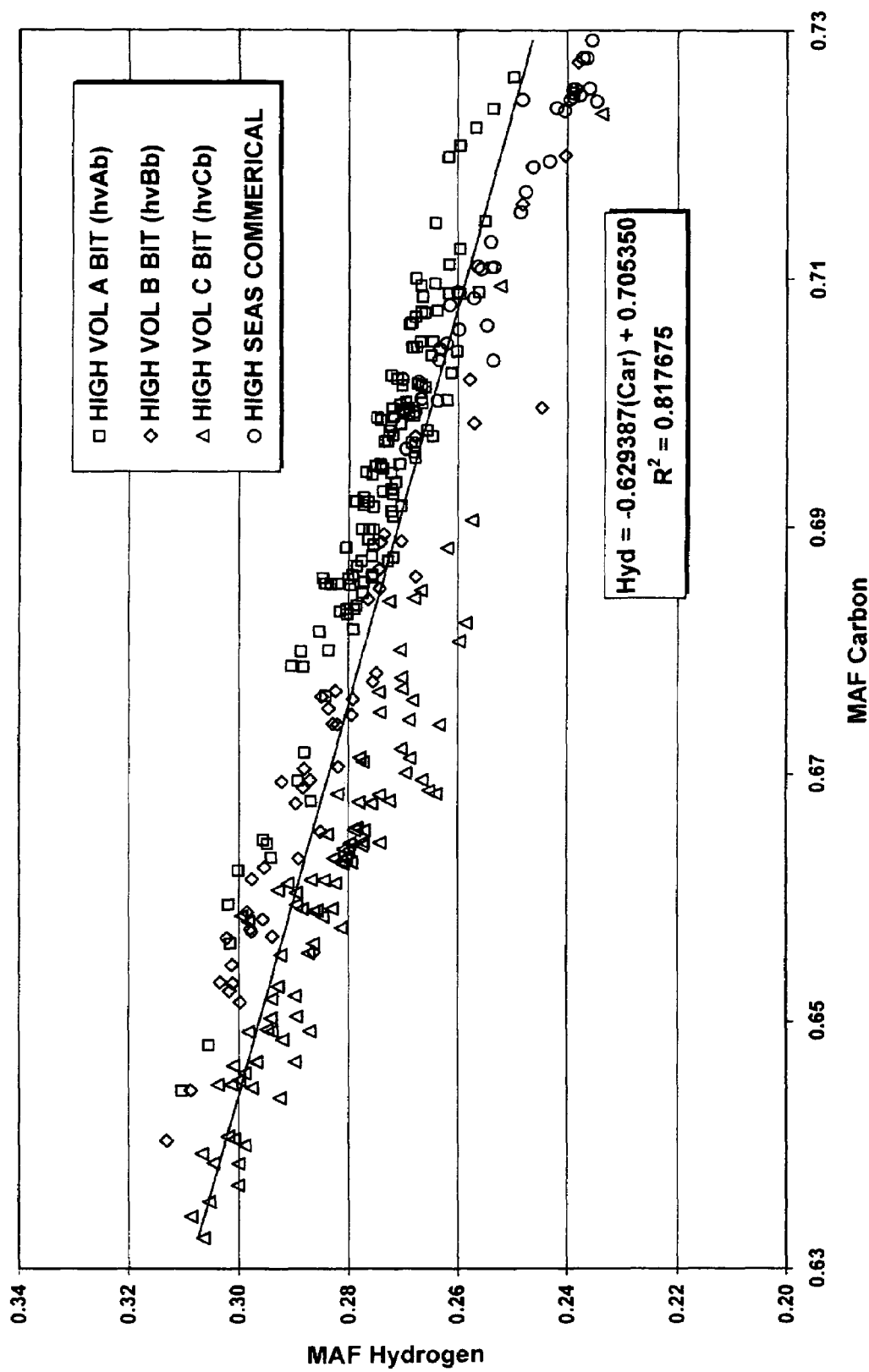
FIG. 5 (prior art) is a plot of MAF molar fuel diatomic hydrogen versus MAF molar fuel carbon for high volatile bituminous coals following the teachings of '994, and as such it is considered prior art. This plot encompasses the following Ranks: high volatile A bituminous (hvAb), high volatile B bituminous (hvBb), high volatile C bituminous (hvCb), and samples of High Seas commercial coal. The resultant $R^2$ value is 81.77%.
Figure 6:
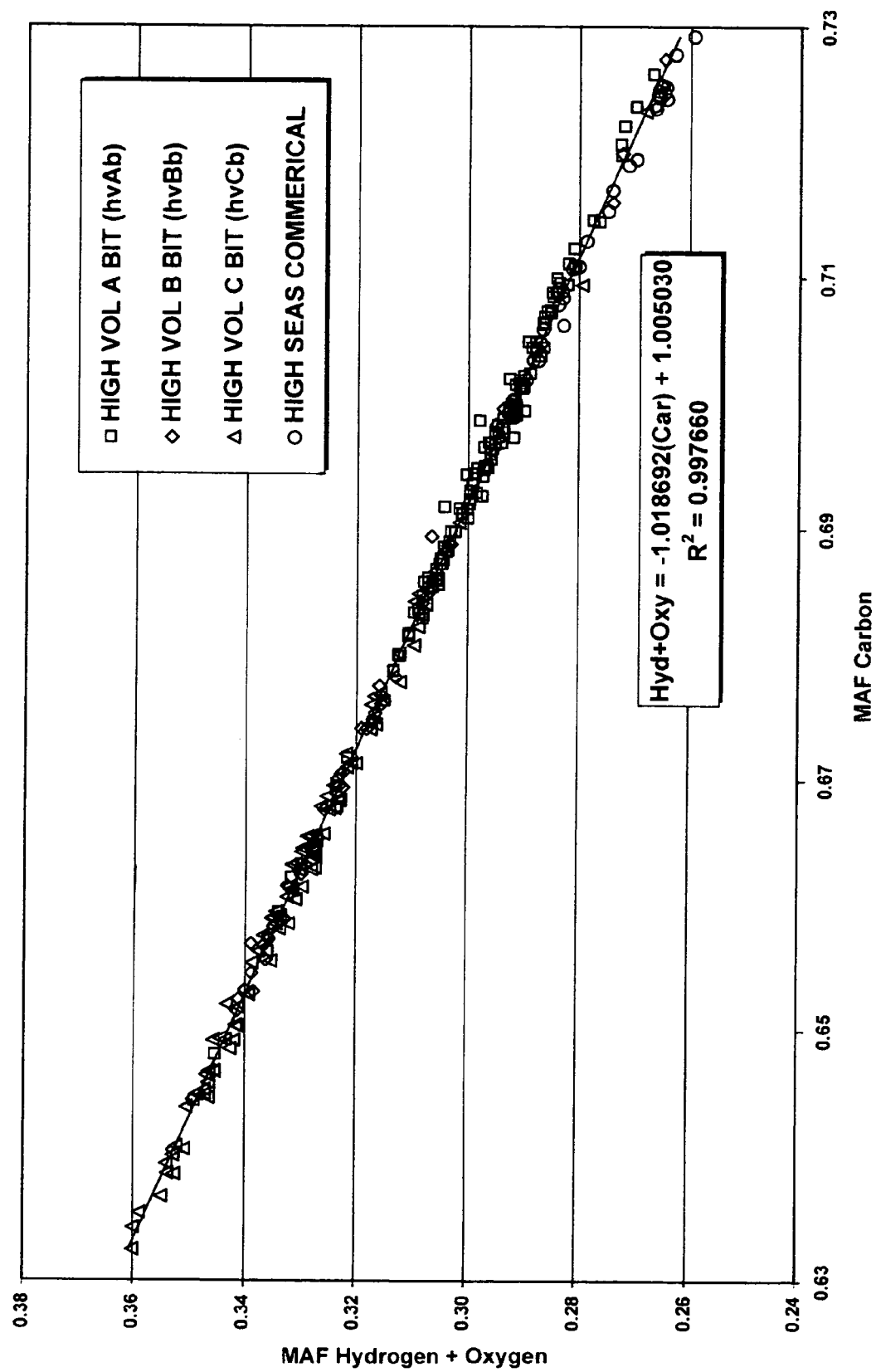
FIG. 6 is a plot of MAF molar fuel diatomic hydrogen plus MAF molar fuel diatomic oxygen versus MAF molar fuel carbon for high volatile bituminous coals following the teachings herein, using the same Ultimate Analysis data as was used for FIG. 5. The resultant $R^2$ value is 99.77%. Refer to TABLE 4 for functionalities.
Figure 7A:
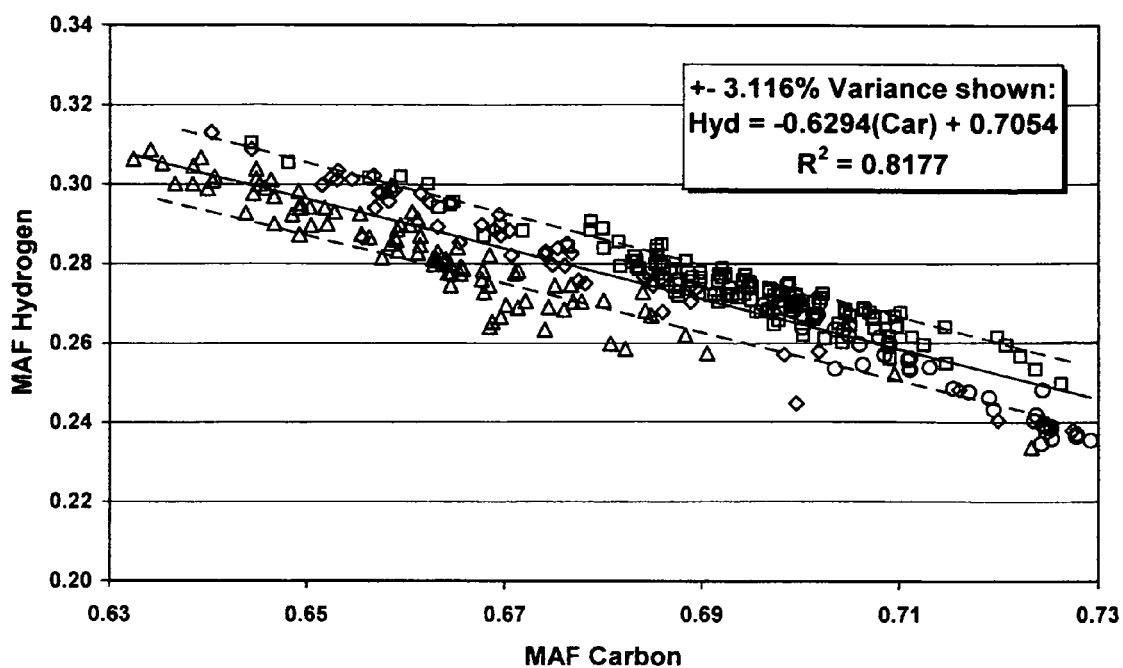
FIG. 7A is a repeat of FIG. 5, using its data, but also indicating both a +3.116% and a −3.116% variance of MAF molar fuel diatomic hydrogen for a given MAF molar fuel carbon. Observe that the preponderance of the data, although evenly distributed, is encompassed within a ±3.116% variance.
Figure 7B:
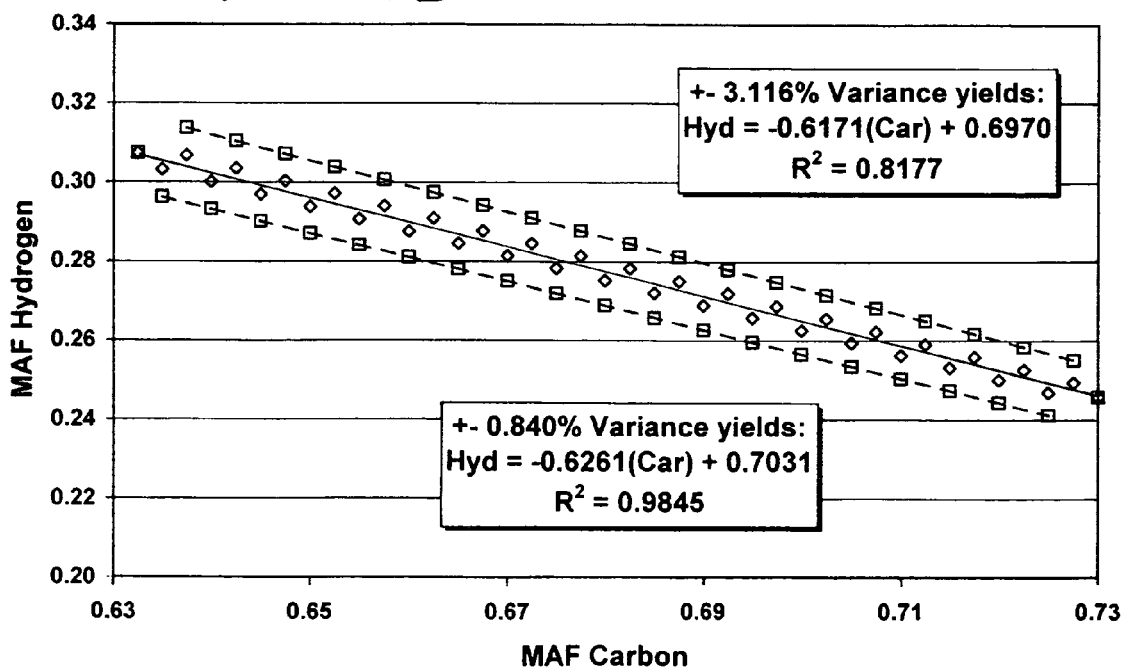
FIG. 7B is a demonstration, using the Excel spreadsheet program, of what a ±3.116% variance means to the computation of $R^2$. The same functionality of data was used as associated with FIG. 5 and FIG. 7A, but using contrived data such that it could be manipulated. The same average frequency in data variation was applied, resulting in the same $R^2$ as found for FIG. 5, at 81.77% (indicated by square symbols). Also plotted in FIG. 7B is a ±0.840% variance, resulting in an $R^2$ of 98.45% (indicated by diamond symbols). See TABLE 4 and TABLE 5 for detailed results.

The data of FIG. 5 (hvAb, hvBb, hvBc and spot High Seas data) is of interest given that the observed distribution of data about the linear mean is approximately uniform. FIG. 5 provides a statistical example in which the $R^2$ value computes artificially high. Using this as a "best case" of '994 methods, FIG. 7A over-plots on FIG. 5 data variance lines at ±3.116%. As observed, these variance lines essentially encompass the data scatter. Establishing the variance lines, FIG. 7B then forms an artificial repeat of FIG. 5 & FIG. 7A using contrived data biased about the mean such that Excel's $R^2$ value matches that of FIG. 5 & FIG. 7A. This is important for the FIG. 7B computed database then allows manipulation of data producing different $R^2$ values. One of these, indicating a ±0.840% variance, yields an $R^2$ value of 98.45, is plotted offering visual understanding of what ≈98% predictability implies. The quantified impact of these and other variances on The Input/Loss Method's computed calorific value based on FIG. 5 data is listed in TABLE 1. The analysis associated with TABLE 1 assumes a uniform distribution, thus the average error to be made in calorific value (CV) is taken as one-half of the full effect. Results indicate that '994 technology clearly indicates unacceptable results when the equivalent error on effluent $CO_2$ is much greater than 1.0% (i.e., the data of FIG. 5 having an $R^2$ value below 82% given a uniform distribution of variances). TABLE 1 also indicates that the effect on computed CV is very much and obviously acceptable when an $R^2$ value is found greater than 98%, a CV error of less than 1% or 263 ΔkJ/kg (113 ΔBtu/lbm). This level of predictability agrees with the commonly accepted error in measured CVs, determined between independent laboratories testing the same fuel samples, at ±233 ΔkJ/kg or ±100 ΔBtu/lbm. One can not ask more in understanding the genesis of fossil fuels than that associated with measurement uncertainty between laboratories testing the same fuel.

Figure 8:
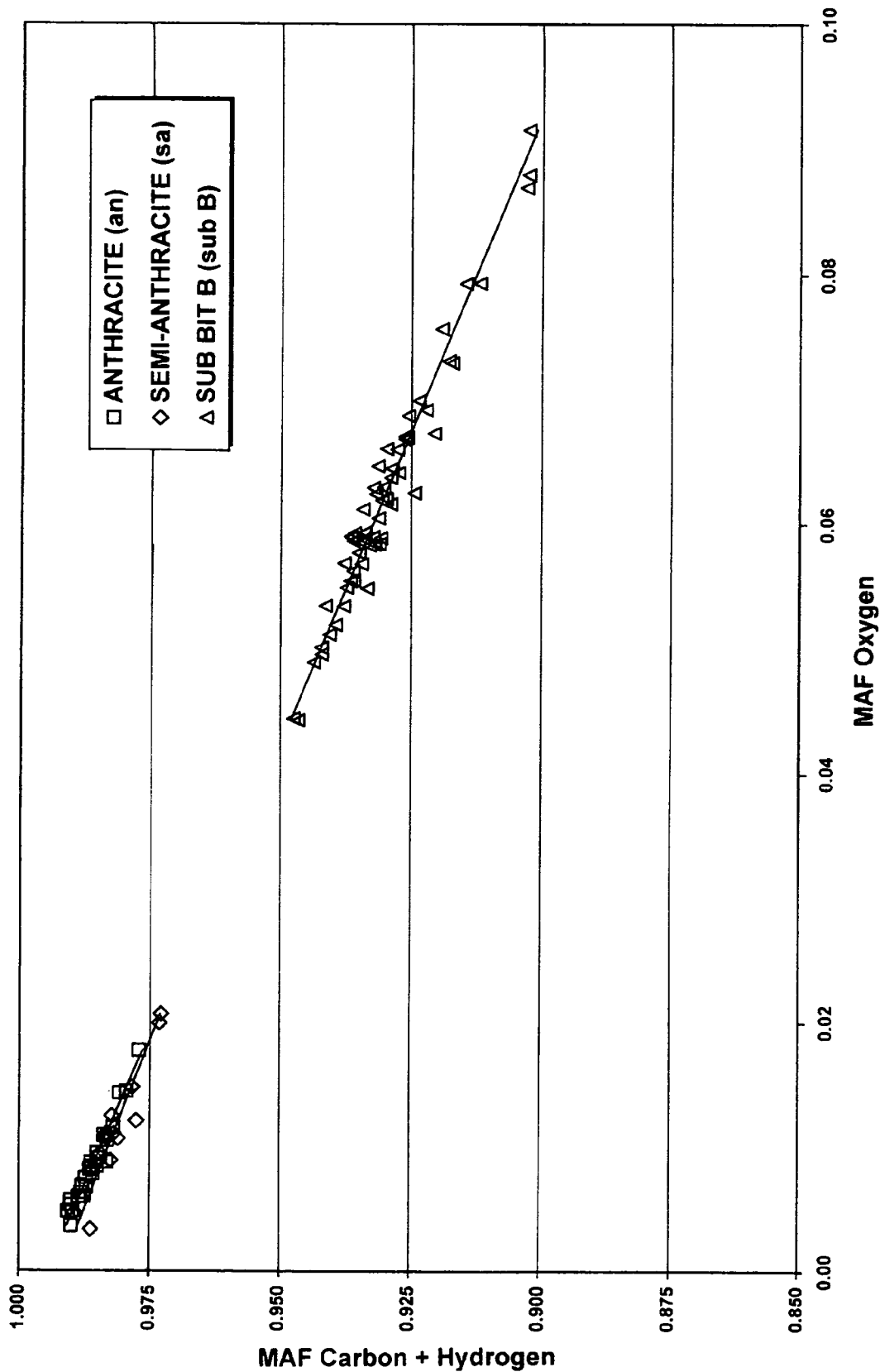
FIG. 8 is a plot of MAF molar fuel carbon plus MAF molar fuel diatomic hydrogen versus MAF molar fuel diatomic oxygen. This plot encompasses the following Ranks of coal: anthracite (an), sem-anthracite (sa) and sub-bituminous B (sub B).
Figure 9:
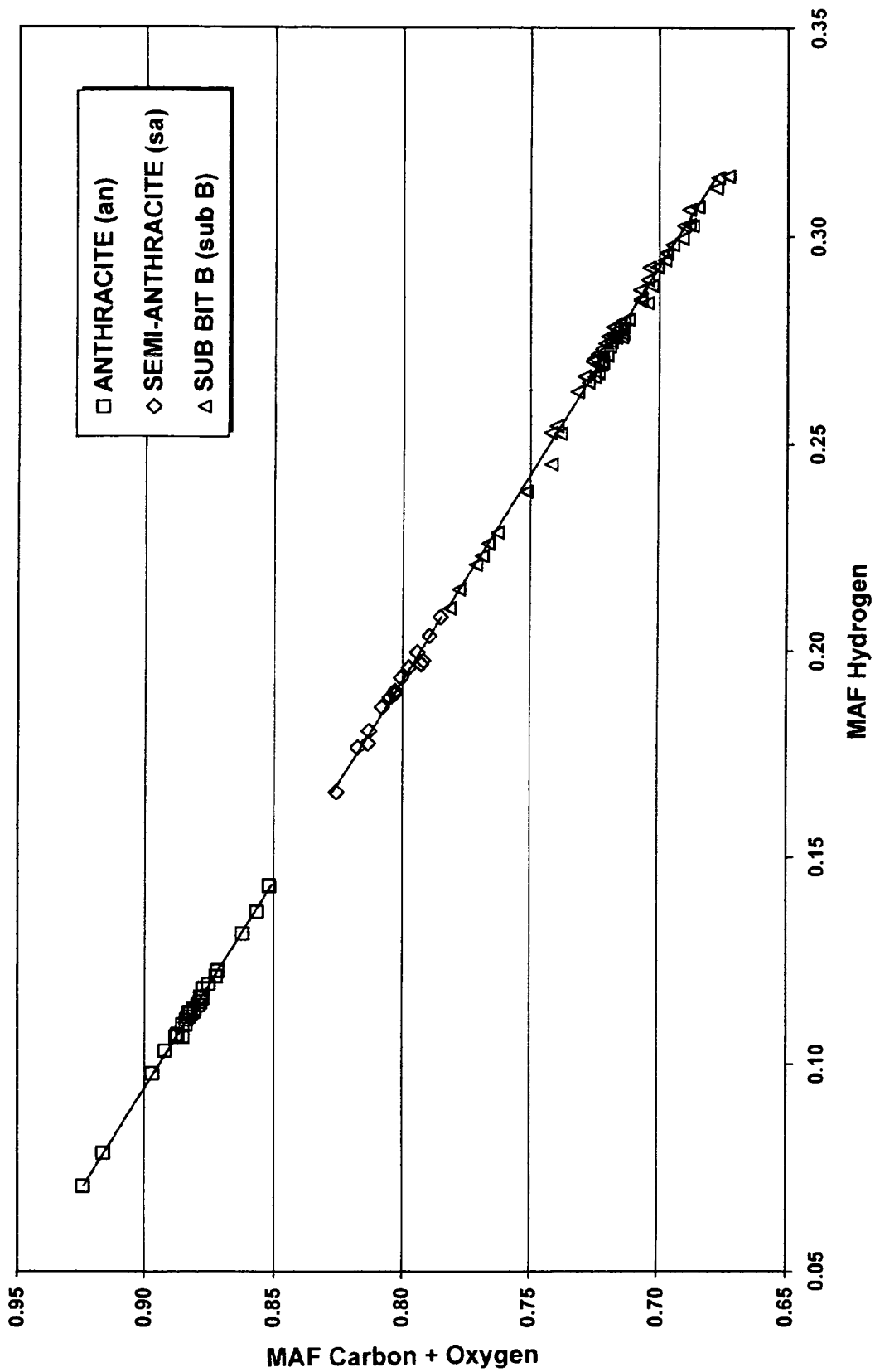
FIG. 9 is a plot of MAF molar fuel carbon plus MAF molar fuel diatomic oxygen versus MAF molar fuel diatomic hydrogen. This plot used the same Ultimate Analysis data as was used for FIG. 8 and follows the teachings of this disclosure. Refer to TABLE 3 for functionalities.
Figure 10:
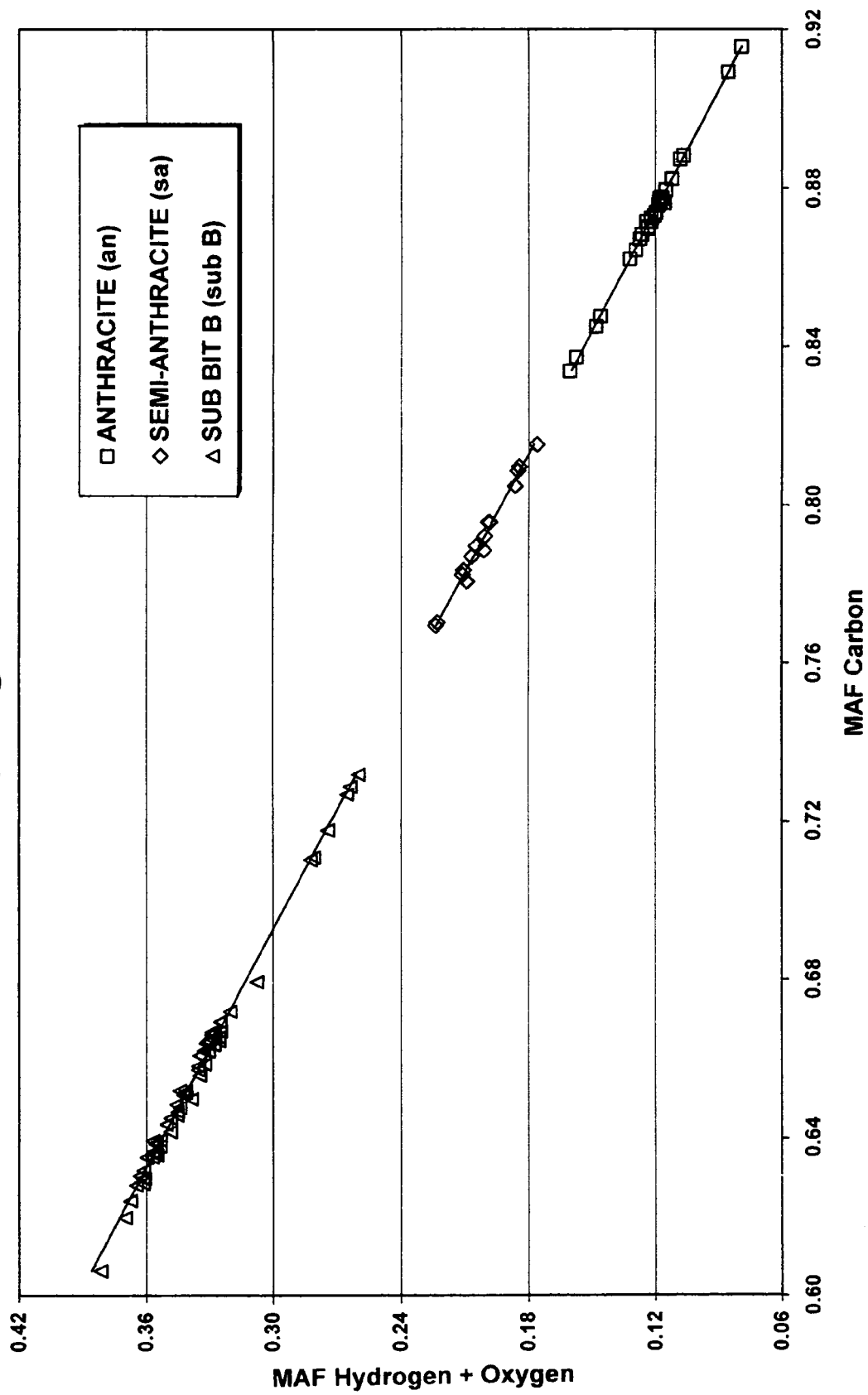
FIG. 10 is a plot of MAF molar fuel diatomic hydrogen plus MAF molar fuel diatomic oxygen versus MAF molar fuel carbon. This plot used the same Ultimate Analysis data as was used for FIG. 8 and follows the teachings of this disclosure. Refer to TABLE 4 for functionalities.
Figure 11:
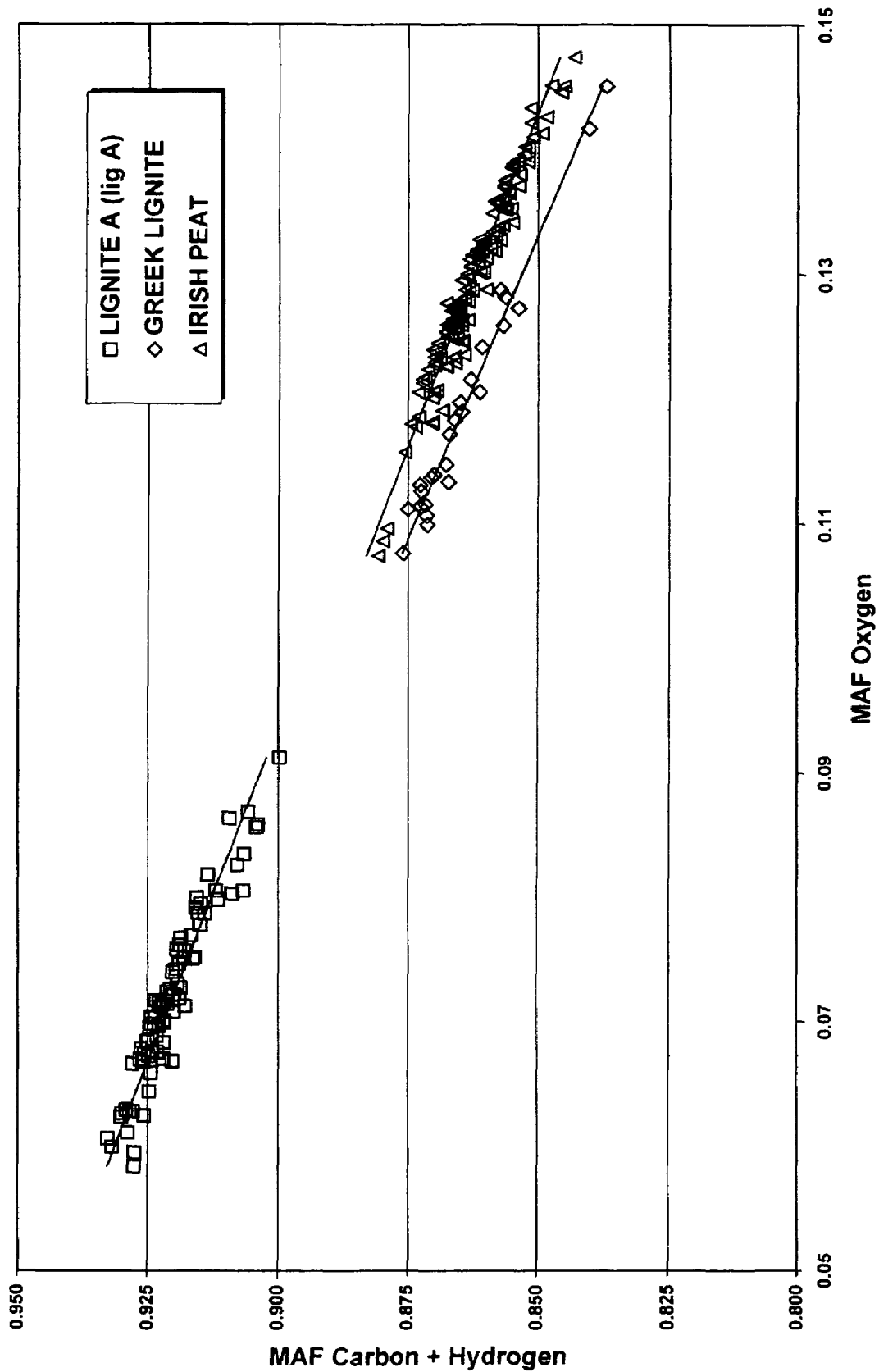
FIG. 11 is a plot of MAF molar fuel carbon plus MAF molar fuel diatomic hydrogen versus MAF molar fuel diatomic oxygen. This plot encompasses the following fossil fuels: lignite A (lig A), samples of Greek lignite (lig B) and Irish peat. Refer to TABLE 2 for functionalities.
Figure 12:
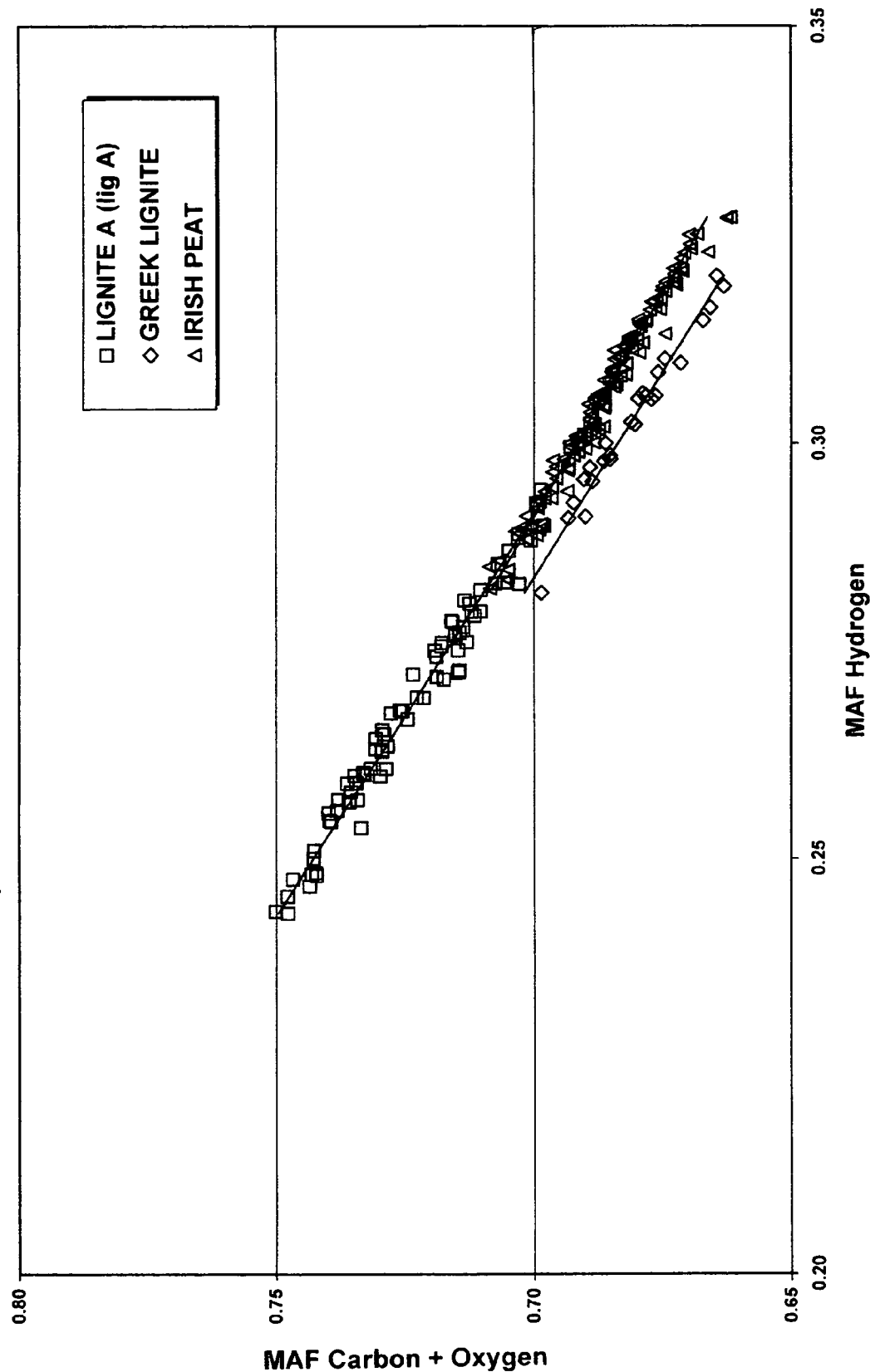
FIG. 12 is a plot of MAF molar fuel carbon plus MAF molar fuel diatomic oxygen versus MAF molar fuel diatomic hydrogen. This plot used the same Ultimate Analysis data as was used for FIG. 11. Refer to TABLE 3 for functionalities.
Figure 13:
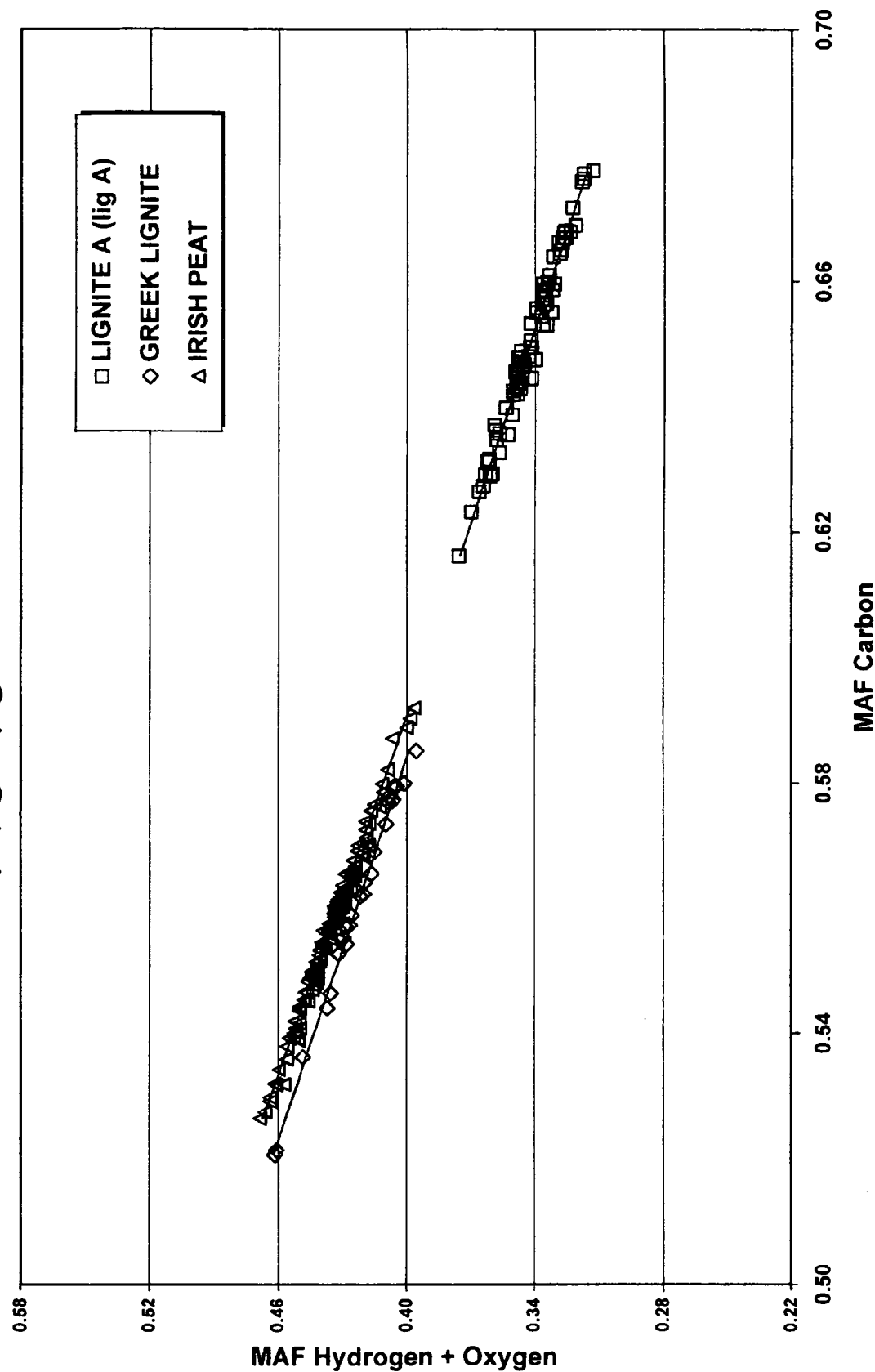
FIG. 13 is a plot of MAF molar fuel diatomic hydrogen plus MAF molar fuel diatomic oxygen versus MAF molar fuel carbon. This plot used the same Ultimate Analysis data as was used for FIG. 11. Refer to TABLE 4 for functionalities.

The predictability of these equations is seen in FIG. 8, FIG. 9 and FIG. 10 for anthracite, semi-anthracite and sub-bituminous B. The predictability of these equations is also seen in FIG. 11, FIG. 12 and FIG. 13 for lignite A, Greek Lignite and Irish peat. The $R^2$ values associated with these and other Ranks are presented in TABLE 2, TABLE 3 and TABLE 4. Such predictability is of such reliability that any of the Eqs.(61), (62) or (63) may be used in the matrix solution. Eq.(63) is chosen such that $(\alpha_{MAF-5}+\alpha_{MAF-3})$ was demonstrated as having no functionality with $L_{10}$ (explained below). In re-arranging terms, Eq.(63) becomes:

$$\alpha_{MAF-3} - K_{OHC3}\alpha_{MAF-4} + \alpha_{MAF-5} = J_{OHC3} \quad (64)$$

TABLE 2

MAF Molar Fuel Carbon + Diatomic Hydrogen
vs MAF Molar Fuel Diatomic Oxygen

| Rank | $J_{OHC1}$ | $K_{OHC1}$ | $R^2$ (%) |
|---|---|---|---|
| anthracite (an) | 0.994587 | −1.029322 | 94.61 |
| semi-anthracite (sa) | 0.992139 | −0.927044 | 88.07 |
| High Seas (hvAb, hvBb, spot) | 0.991273 | −0.968619 | 96.66 |
| sub-bituminous A (sub A) | 0.987991 | −0.917961 | 95.55 |
| Powder River Basin | 0.995394 | −1.017100 | 98.99 |
| sub-bituminous B (sub B) | 0.992029 | −0.993473 | 95.75 |
| sub-bituminous C (sub C) | 0.981005 | −0.849783 | 88.78 |
| lignite A (lig A) | 0.986298 | −0.919924 | 88.64 |
| Greek lignite | 0.986963 | −1.028534 | 97.45 |
| Irish peat | 0.984391 | −0.940798 | 94.18 |

TABLE 3

MAF Molar Fuel Carbon + Diatomic Oxygen
vs MAF Molar Fuel Diatomic Hydrogen

| Rank | $J_{OHC2}$ | $K_{OHC2}$ | $R^2$ (%) |
|---|---|---|---|
| anthracite (an) | 0.994791 | −1.003952 | 99.74 |
| semi-anthracite (sa) | 0.993794 | −1.004406 | 97.99 |
| High Seas (hvAb, hvBb, spot) | 0.982893 | −0.966008 | 99.51 |
| sub-bituminous A (sub A) | 0.994627 | −1.008012 | 99.42 |
| Powder River Basin | 0.996057 | −1.006130 | 99.73 |
| sub-bituminous B (sub B) | 0.992464 | −1.000103 | 99.33 |
| sub-bituminous C (sub C) | 1.000139 | −1.032331 | 98.55 |
| lignite A (lig A) | 1.000654 | −1.031797 | 97.59 |
| Greek lignite | 0.988563 | −1.016521 | 97.23 |
| Irish peat | 0.971585 | −0.933134 | 97.19 |
| Generic Non-Volatile (an, sa, sub A, sub B, sub C, lig A) | 0.995497 | −1.011011 | 99.95 |

TABLE 1

Practical Impact of $R^2$ on The Input/Loss Method Based on FIG. 5 Data

| Equation (from FIG. 5): Hyd = [−0.6294(Car) + 0.7054] (1.0 ± Var/100) | $R^2$ (%) Computed by Excel | Impact of ½ Variance on Effluent $CO_2$ (%) | Impact of Effluent $CO_2$ on Input/Loss As-Fired Calorific Value (CV), without Error Analysis or $L_{10}$ Correction |
|---|---|---|---|
| Variance = 0.000% | 100.00 | 0.0000 | none, CV = 29107.934 kJ/kg (12514.159 Btu/lbm) |
| Variance = 0.840% | 98.45 | 0.2720 | 0.90%, 263 ΔkJ/kg (113 ΔBtu/lbm) |
| Variance = 1.556% | 94.83 | 0.5040 | 1.65%, 481 ΔkJ/kg (207 ΔBtu/lbm) |
| Variance = 2.334% | 88.98 | 0.7560 | 2.46%, 716 ΔkJ/kg (308 ΔBtu/lbm) |
| Variance = 3.116% | 81.77 | 1.0095 | 3.26%, 948 ΔkJ/kg (408 ΔBtu/lbm) |

TABLE 4

MAF Molar Fuel Diatomic Hydrogen + Diatomic Oxygen
vs MAF Molar Fuel Carbon

| Rank | $J_{OHC3}$ | $K_{OHC3}$ | $R^2$ (%) |
|---|---|---|---|
| anthracite (an) | 0.989047 | −0.993931 | 99.80 |
| semi-anthracite (sa) | 0.986130 | −0.991377 | 98.60 |
| High Seas (hvAb, hvBb, spot) | 1.007944 | −1.022818 | 99.68 |
| High Volatile (hvAb, hvBb, hvCb, spot) | 1.005030 | −1.018692 | 99.77 |
| sub-bituminous A (sub A) | 0.990659 | −0.997212 | 99.50 |
| Powder River Basin | 0.986835 | −0.988635 | 99.77 |
| sub-bituminous B (sub B) | 0.989209 | −0.995069 | 99.43 |
| sub-bituminous C (sub C) | 0.971525 | −0.969655 | 98.13 |
| lignite A (lig A) | 0.963022 | −0.955311 | 96.97 |
| Greek lignite | 0.971701 | −0.978878 | 99.19 |
| Irish peat | 1.017332 | −1.045620 | 98.45 |

Figure 14:
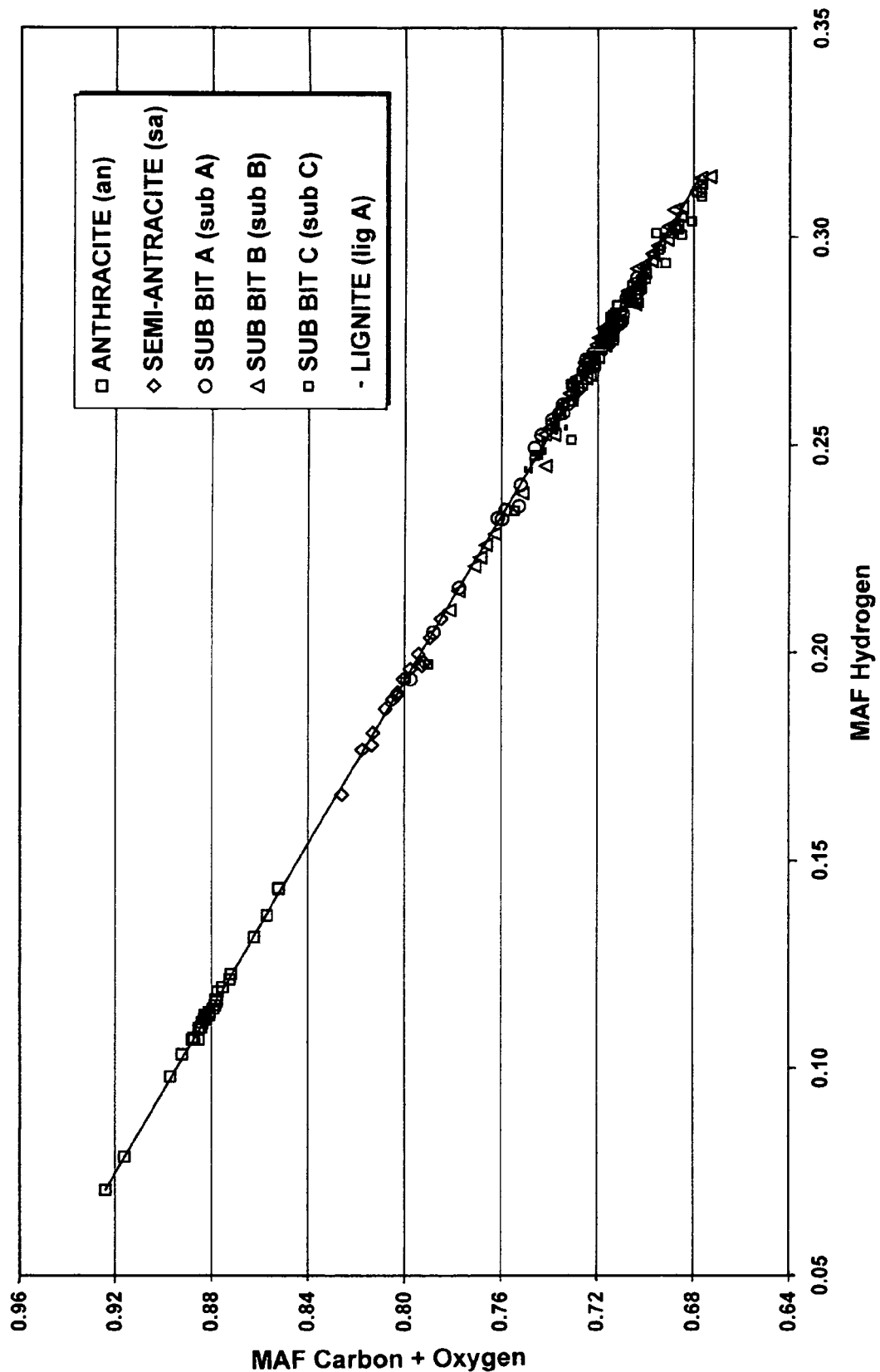
FIG. 14 is a plot of MAF molar fuel carbon plus MAF molar fuel diatomic oxygen versus MAF molar fuel diatomic hydrogen. This plot encompasses the following Ranks of coal: anthracite (an), semi-anthracite (sa), sub-bituminous A (sub A), sub-bituminous B (sub B), sub-bituminous C (sub C) and lignite A (lig A).

The consistency observed in the above TABLES is also observed in a wide collection of fuel samples, depending on which multi-variant analysis is chosen. FIG. 14 is a plot of MAF molar fuel carbon plus MAF molar fuel diatomic oxygen versus MAF molar fuel diatomic hydrogen using both the highest and lowest energy fuels: anthracite (an), sem-anthracite (sa), sub-bituminous A (sub A), sub-bituminous B (sub B), sub-bituminous C (sub C) and lignite A (lig A). As observed, with an $R^2$ value of 99.95% (TABLE 3), such predictability portents further use of Eq.(62) than just providing a missing equation for The Input/Loss Method. Eq.(62) may be used to over-check Ultimate Analysis results for any fuel falling into these general Ranks. In essence, Eq.(61), (62) and (63) may be used as an over-check for data outliers. As seen with careful observation of FIG. 14, two or three of the sub C data may be classed as outliers. What is being described through Eqs.(61), (62) and (63) is the inherent carbon, hydrogen and oxygen make-up of a fossil fuel, its Oxy-Hydrocarbon construct. Indeed, it can be demonstrated as consistent at the MAF molar level. A general comparison of '994 methods and those advocated by this invention is observed in TABLE 5. Note that all $R^2$ values for the present invention are greater than 98% except lignite A. Such genesis is simply not seen with single-variant analysis. With such genesis, the tools may then be employed to verify raw Ultimate Analysis laboratory data.

TABLE 5

Comparison of '994 versus Present Invention

| Rank | $R^2$ (%) for '994: MAF hydrogen = $f$(MAF carbon) | $R^2$ (%) for Present Invention: MAF hydrogen + MAF oxygen = $f$(MAF carbon) |
|---|---|---|
| anthracite (an) | 97.40 | 99.80 |
| semi-anthracite (sa) | 90.34 | 98.60 |
| High Volatile (hvAb, hvBb, hvCb, spot) | 81.77 | 99.77 |
| sub-bituminous A (sub A) | 90.52 | 99.50 |
| Powder River Basin | 71.93 | 99.77 |
| sub-bituminous B (sub B) | 86.64 | 99.43 |
| sub-bituminous C (sub C) | 87.36 | 98.13 |
| Greek lignite | 83.46 | 99.19 |
| lignite A (lig A) | 77.93 | 96.97 |
| Irish peat | 65.90 | 98.45 |

The genetics of a fossil fuel of interest, if a viable concept, should allow specification of the chemical construct of its Rank. Indeed, it should be consistent enough to be used to specify a coal's Ranks based on Ultimate Analysis results. To produce such findings, note that Eqs.(61), (62) and (63) represent three equations and three unknowns: the molar ratios of carbon to molecular hydrogen, to molecular oxygen. Solving for these equations (using data from TABLE 2, TABLE 3 and TABLE 4) results in specification of what a particular fossil fuel Rank truly means. TABLE 6 presents results for such analysis, presented by a generic chemical makeup: $CH_{c2}O_{c3}$ where the molar constants c2 and c3 are normalized to one mole of carbon. The consistency of TABLE 6 is apparent and belays the notion of separative analyses of TABLE 2, TABLE 3 or TABLE 4 data. TABLE 6 employs ASTM D388 defined Ranks, which is not to be taken as limiting the application. As an example of using TABLE 6, note that the poorer lignites and Irish peat fuels, at the MAF level, are more "friendly" toward the environment that the higher energy coals (an & sa) in that less effluent $CO_2$ is produced per burnt carbon. This would suggest more research towards reducing lignite's mineral matter (Irish peat has little mineral matter), and reducing the water content in these traditionally poor fuels. Using the type of data contained in TABLE 2, TABLE 3 and TABLE 4 to develop chemical makeups also will define the occasional strange fuel. One such fuel is Bear Canyon coal, although a western US coal, it is mined in Utah outside the Powder River Basin (its data is not part of FIG. 3 or FIG. 4). Bear Canyon computes as $CH_{0.9197}O_{0.0762}$, having a normalized molecular weight of 14.1577. The oxygen content of this coal indicates a High Seas coal while its hydrogen content indicates a lignite A or B. Since Bear Canyon coal has little water content (most unlike PRB coals), its genetics, as taught herein, would suggest it being most environmentally friendly, it being closer to methane than any other known coal.

TABLE 6

Reduction of Multi-Variant Analysis to $CH_{c2}O_{c3}$

| Rank | Hydrogen (c2) | Oxygen (c3) | Practical Oxygen Range |
|---|---|---|---|
| graphite | 0.0000 | 0.0000 | not applicable |
| anthracite (an) | 0.2600 | 0.0191 | $\geq 0.009$, $\leq 0.024$ |
| semi-anthracite (sa) | 0.4803 | 0.0283 | $\geq 0.025$, $\leq 0.054$ |
| High Seas (hvAb, hvBb, spot) | 0.7844 | 0.0790 | $\geq 0.055$, $\leq 0.121$ |
| sub-bituminous A (sub A) | 0.7661 | 0.1640 | $\geq 0.122$, $\leq 0.170$ |
| Powder River Basin | 0.8136 | 0.1751 | $\geq 0.171$, $\leq 0.183$ |
| sub-bituminous B (sub B) | 0.8348 | 0.1900 | $\geq 0.184$, $\leq 0.200$ |
| sub-bituminous C (sub C) | 0.8808 | 0.2074 | $\geq 0.201$, $\leq 0.215$ |
| lignite A (lig A) | 0.8295 | 0.2221 | $\geq 0.216$, $\leq 0.230$ |
| Greek lignite (lig B) | 1.0788 | 0.4249 | $\geq 0.390$, $\leq 0.458$ |
| Irish peat | 1.1314 | 0.4888 | $\geq 0.459$, $\leq 0.520$ |
| methane | 4.0000 | 0.0000 | not applicable |

The consistency of TABLE 6 suggests that these findings be used to over-check laboratory Ultimate Analyses. The LECO Corporation, St. Joseph, Mich. state in the U.S. manufacture laboratory equipment which is used to determine Ultimate Analyses. Their equipment includes the LECO CHN 600 instrument for determining elemental carbon (C), hydrogen (H) and nitrogen (N). Their LECO CHN 132 instrument determines elemental sulfur (S). The PerkinElmer Inc., Wellesley, Md. state in the U.S. manufactures a Model 2400 Series II CHNS/O Analyzer for elemental carbon, hydrogen, nitrogen, sulfur and oxygen (by difference). These instruments would benefit when analyzing coal samples by incorporating the teachings associated with TABLE 6. Many such analyzers run in an automatic fashion, analyzing a number of samples at the same time and thus convenient to form multi-variant relationships resulting in similar data to that found in TABLE 2, TABLE 3 and TABLE 4. A data processing device would then reduce such data to a $CH_{c2}O_{c3}$ form or its equivalence. The ability of the laboratory to report data outliers associated with such analyses would greatly improve diagnostics when testing coal samples; and would assist in discovery of unique fuels (such as Bear Canyon coal). Specifically, this invention consists of a data processing device for evaluating Ultimate Analysis data, the device comprising: a) a data acquisition device to collect data from the thermal system including at least a selection of Choice Operating Parameters, the data acquisition device producing a set of acquired system data; b) a computer with a processing means; c) a set of instructions for configuring the processing means to determine a fuel chemistry of the fossil fuel and to receive as input the set of acquired system data, resulting in a programmed computer; d) means by which the programmed computer receives as input the set of acquired system data; e) the programmed computer producing the fuel chemistry of the fossil fuel; and f) means for reporting the fuel chemistry of the fossil fuel to assist in the operation of the thermal system. Further, the invention also comprises a means to compare an Ultimate Analysis with a set of descriptive fossil fuel data based on the genetics of fossil fuels organized by categories (such as TABLE 6) including instructions to identify outlier Ultimate Analysis data. The following notes apply: 1) "a set of ultimate analysis instruments" means one or more than one instrument, examples of such instruments are cited above; 2) oxygen is typically computed by difference (i.e., O is produced by 1.0 minus C, H, N and S); 3) elemental concentrations are typically provided as weight fractions, conversion to molar is taught through Eqs.(94) & (93); 4) "a data processing" may be any one of the following: a device integrated within the ultimate analysis instrument, a common personal computer, a specialized computer, a hand-held computer, or an integrated circuit; and 5) the "genetics of fossil fuels" is a defined concept (its descriptive material being taught throughout this disclosure, e.g., Eqs.(61), (62), (63), (72), FIG. 16, FIG. 18, TABLE 6, etc.) and includes all numerical results herein. Also note that a comparison of coal Ranks assumes a nominal range of uncertainty about oxygen values found in TABLE 6, said uncertainties being found after analyses and are indicated in TABLE 6. Comparison of coal Ranks may also assume ranges of uncertainty about hydrogen (i.e., the "c2" term).

The consistency of multi-variant analyses leading to the genetics of fossil fuels, has proven definitive for a wide variety of fuels, but also has proven indicative of poor industrial practices when obtaining Ultimate Analyses. As demonstrated, multi-variant analysis is definitive for the following coals, lignites and peat: an, sa, sub A, Powder River Basin, sub B, sub C, lig A, Greek lignite (lig B), and Irish peat. However, such findings as these have not been found universal. The research supporting this invention has found that the volatile Ranks of coal (lvb, mvb, hvAb, hvBb and hvCb) do not produce high $R^2$ values when using analyses produced by laboratories following ASTM procedures. The reason for this is aggressive heating of laboratory samples performed before Ultimate Analyses which drives off hydrogen-base materials which are not tested. Although the $R^2$ values for such fuels are considerably higher when using multi-variant analysis, results are not satisfying given the high accuracy results discovered for non-volatile fuels. For MAF molar fuel carbon plus MAF molar fuel oxygen versus MAF molar fuel hydrogen $R^2$ values include: 88.35% for lvb; 91.44 for mvb; 84.51% for hvAb; 73.92% for hvBb; and 69.72% for hvCb. The database considered for FIG. 5, FIG. 6 and FIG. 7A, although internally consistent, was edited to eliminate what was believed to be the effects of volatile hydrocarbons driven off by aggressively heating laboratory samples, all from the U.S. The database considered for FIG. 5, FIG. 6 and FIG. 7A obtained from non-U.S. laboratories was not edited. Other than advising U.S. laboratories not to over-heat volatile coal samples, the inventive point is that multi-variant analysis affords an excellent method of checking that coal samples result in consistent Ultimate Analyses and calorific values.

$L_{10}$ Factor

Taught in '994 via its Eq.(72) is use of a "fuel factor". Taught in '877, U.S. Pat. Nos. 6,651,035, 6,745,152, application US2004/128111 and application WO2003/091881 all via an Eq.(72A-alt), is use of a "L Factor" for correction of effluent errors and for use in the detection of tube failures in steam generators. Both the "fuel factor" of '994, and the "L Factor" of '877, etc. are the same quantity, herein defined as the $L_5$ Factor. Taught in U.S. Pat. No. 6,560,563 is the use of an "L Factor". Taught in U.S. Pat. No. 6,691,054 is the use an "F Factor". Prior to the development of the present invention, the $L_5$ Factor was found adequate as a descriptive quantity which, when plotted as a function of MAF molar fuel diatomic oxygen, could be normalized in such a manner as to produce a constant value. A corrected and constant $L_5$ Factor ($L_{5\text{-}corr}$) proved useful when incorporated with a number of inventions associated with The Input/Loss Method. However, when used with Irish peat, Powder River Basin coals and High Seas coals, the $L_5$ Factor showed poor correlation. Thus in parallel with the development of the genetics of fossil fuels, and guided by that development, a new L Factor was discovered, termed the $L_{10}$ Factor, which indicates a high degree of predictability for a wide range of fuels, including Irish peat, Powder River Basin coals and High Seas coal. Its corrected value, $L_{10\text{-}corr}$, is essentially constant. The $L_{10}$ Factor is defined by the following, common units of measure being (mass of dry effluent)/(mass of MAF fuel):

$$L_{10} \equiv [x_{DRY\text{-}theor}N_{DRY\text{-}Fuel} + a_{DRY\text{-}theor}(1.0 + \phi_{Ref})N_{Air} - J_{theor}N_{H2O} - x_{DRY\text{-}theor}\alpha_{DRY\text{-}10}N_{Ash}]/(x_{MAF\text{-}theor}N_{MAF\text{-}Fuel}) \quad (70)$$

This form is taken to accent combustion moisture and ash terms (versus a direct effluent calculation). Note that Eq. (70)'s nomenclature follows Eq.(29F), but where a dried fuel is burned theoretically, producing no effluent $O_2$, nor pollutants; and divided by the mass of moisture-ash-free fuel per the stoichiometric base. Note that $x_{DRY\text{-}theor}$ is the moles of dried fuel based on theoretical combustion; $N_{DRY\text{-}Fuel}$ is the molecular weight of dried fuel; $a_{DRY\text{-}theor}$ is the moles of ambient dry air required to theoretically combust the dried fuel; etc.

Figure 15:
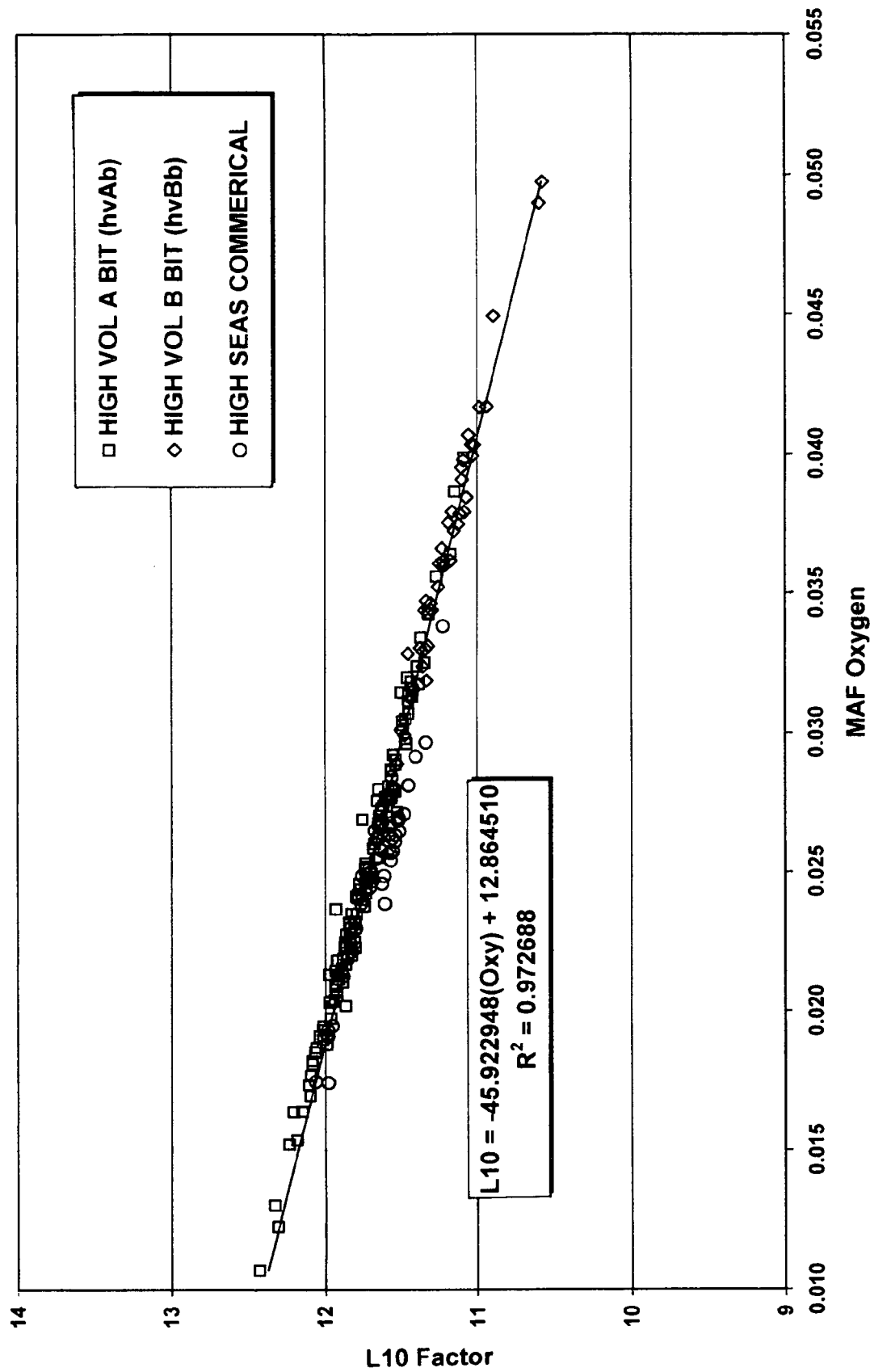
FIG. 15 is a plot of the $L_{10}$ Factor versus MAF molar fuel diatomic oxygen for high volatile bituminous and High Seas coals using FIG. 5 (FIG. 6 and FIG. 7A) data, with the exception of hvCb.
Figure 16:
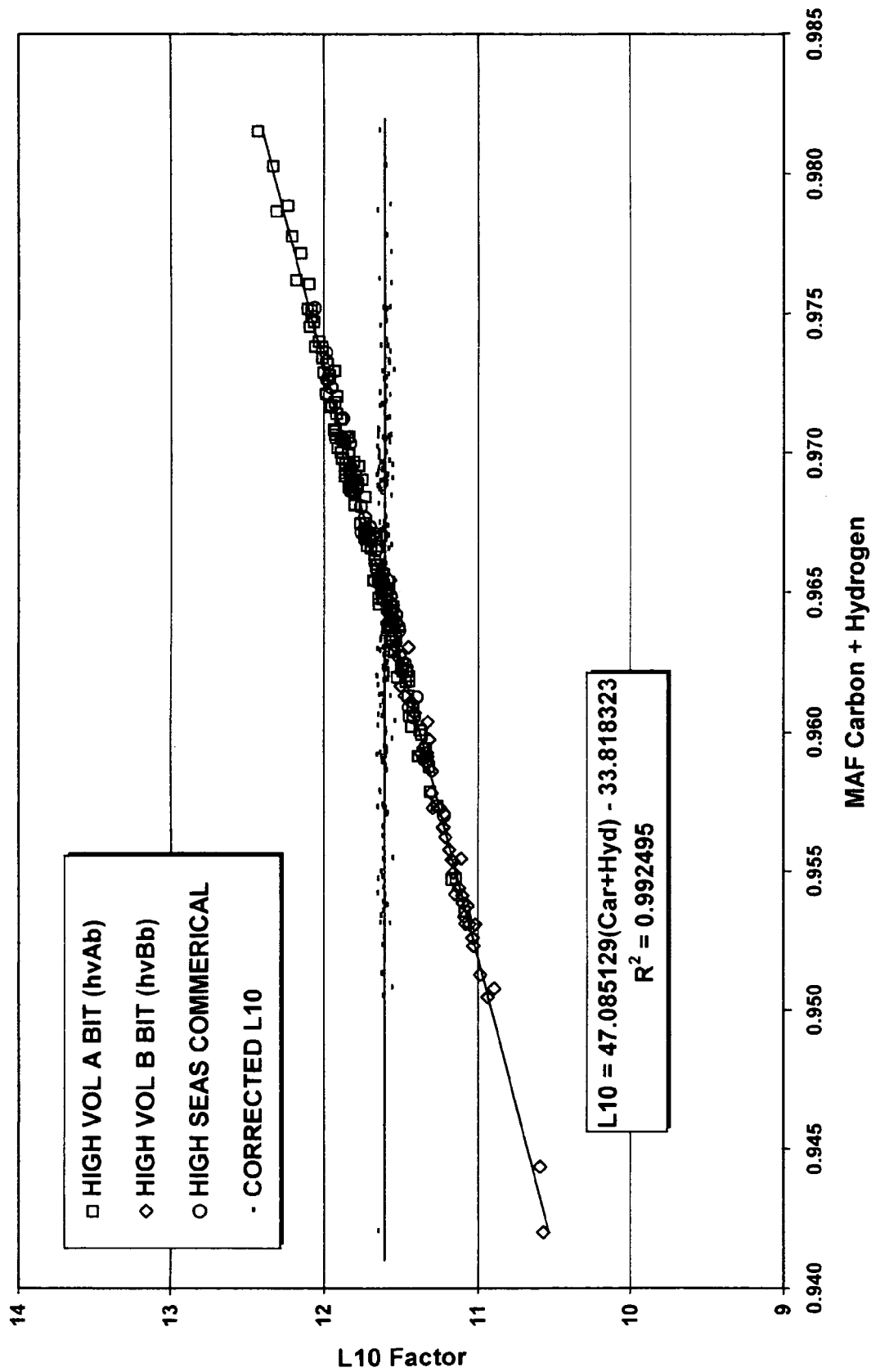
FIG. 16 is a plot of the $L_{10}$ Factor versus MAF molar fuel carbon plus MAF molar fuel diatomic hydrogen for high volatile bituminous and High Seas coals using the same Ultimate Analysis data as was used for FIG. 5 (FIG. 6, FIG. 7A and FIG. 15).
Figure 17:
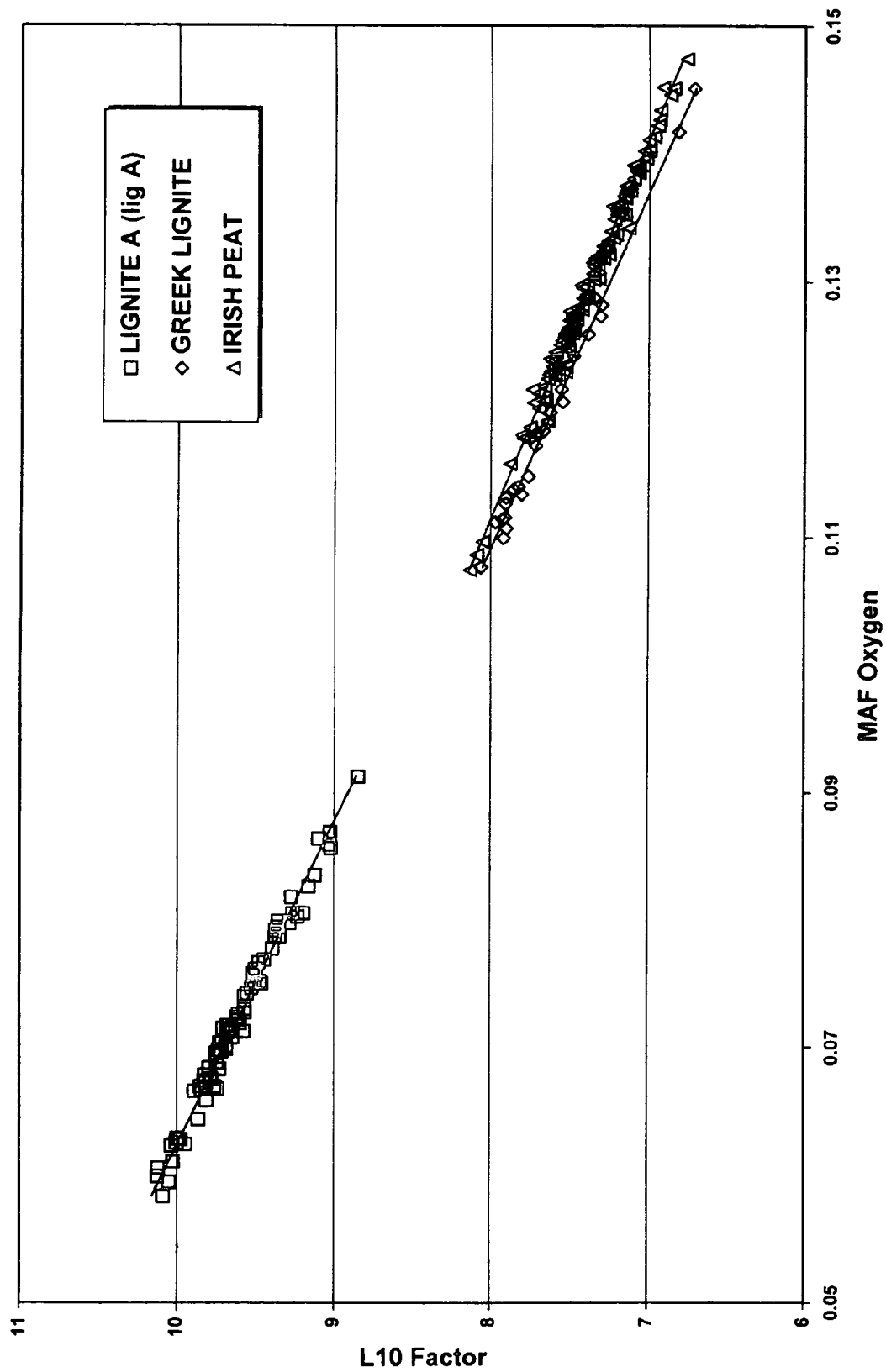
FIG. 17 is a plot of the $L_{10}$ Factor versus MAF molar fuel diatomic oxygen. This plot used the same Ultimate Analysis data as was used for FIG. 11. Refer to TABLE 7 for functionalities.
Figure 18:
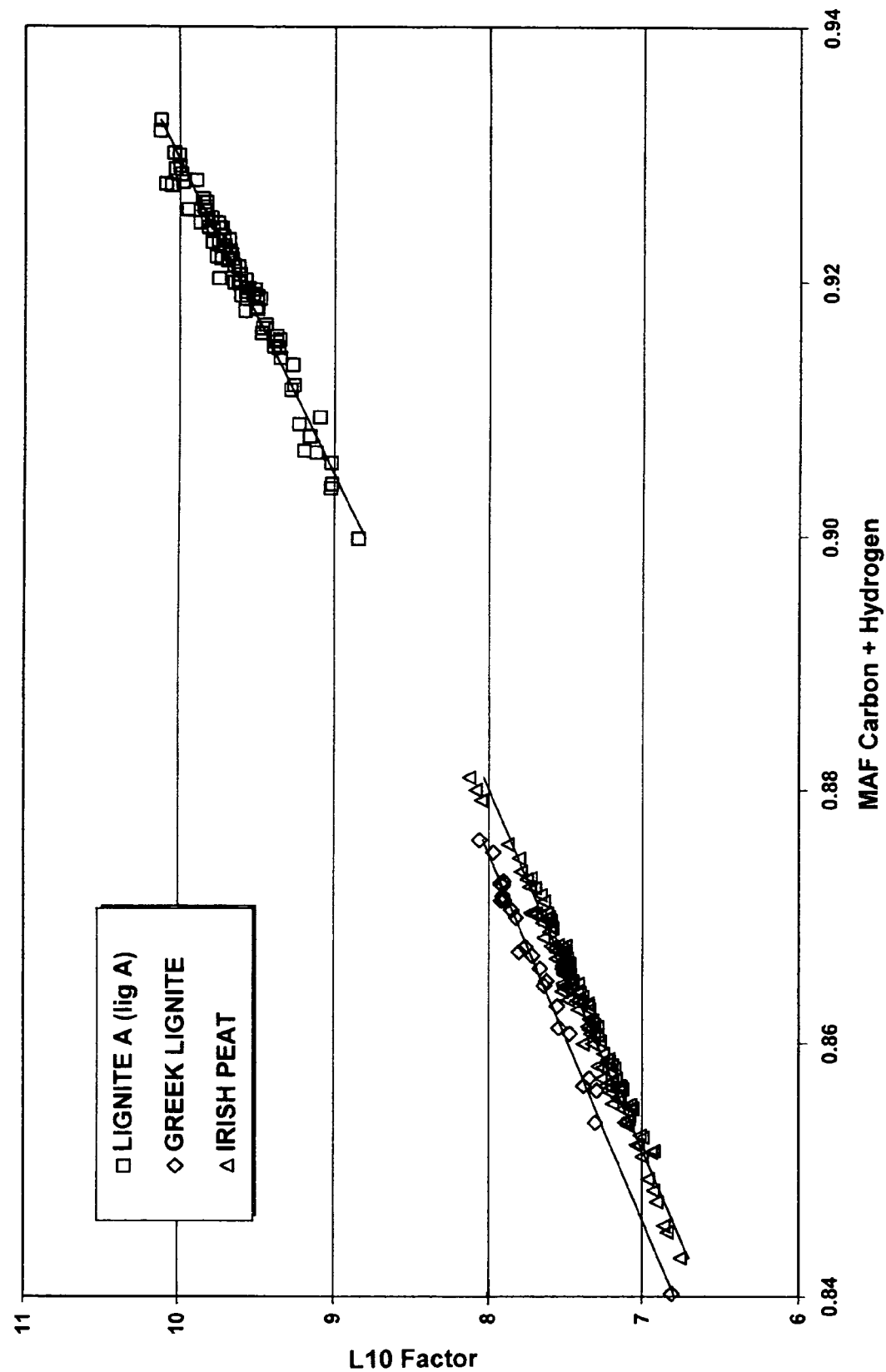
FIG. 18 is a plot of the $L_{10}$ Factor versus MAF molar fuel carbon plus MAF molar fuel diatomic hydrogen. This plot used the same fuels as for FIG. 11. Refer to TABLE 8 for functionalities.

When $L_{10}$ is plotted against either MAF molar fuel diatomic oxygen or the sum of MAF molar fuel carbon plus MAF molar fuel diatomic hydrogen, a high degree of predictability is found. FIG. 15, plotting High Seas coal data indicates an $R^2$ value of 97.27%. Using the same data as for FIG. 15, FIG. 16 plots against MAF molar fuel carbon plus MAF molar fuel diatomic hydrogen, indicating an $R^2$ value of 99.25%. FIG. 17 plots low energy fuels against MAF molar fuel oxygen. Using the same data as for FIG. 17, FIG. 18 plots against MAF molar fuel carbon plus MAF molar fuel diatomic hydrogen. The resultant correlations may be represented by the following:

$$L_{10} = G_{OHC1} + H_{OHC1}\alpha_{MAF\text{-}3} \quad (71)$$

$$L_{10} = G_{OHC2} + H_{OHC2}(\alpha_{MAF\text{-}4} + \alpha_{MAF\text{-}5}) \quad (72)$$

The regression constants, $G_{OHCk}$ and $H_{OHCk}$, for a number of Ranks, are presented in TABLE 7 and TABLE 8. Note that FIG. 16 also indicates the results of correcting $L_{10}$ such that a constant (corrected) value may be used with '877 methods. In the Preferred Embodiment, $L_{10}$ is corrected using the following formulation:

$$L_{10\text{-}corr} = L_{10} + [-H_{OHC2}(\alpha_{MAF\text{-}4} - \alpha_{MAF\text{-}4\text{-}Ref} + \alpha_{MAF\text{-}5} - \alpha_{MAF\text{-}5\text{-}Ref})] \quad (73)$$

where the reference values of the fuel ($\alpha_{MAF\text{-}4\text{-}Ref}$ and $\alpha_{MAF\text{-}5\text{-}Ref}$) are arbitrarily chosen, but should generally reflect the actual fuel and its reference MAF calorific value. FIG. 16 indicates essentially a straight line representation of the corrected $L_{10\text{-}corr}$. Notably the $L_{10}$ Factor indicates no correlation when plotted against MAF molar fuel carbon plus MAF molar fuel diatomic oxygen, nor against MAF molar fuel diatomic hydrogen plus MAF molar fuel diatomic oxygen.

TABLE 7

L10 vs. MAF Molar Diatomic Oxygen

| Rank | $G_{OHC1}$ | $H_{OHC1}$ | $R^2$ (%) |
|---|---|---|---|
| anthracite (an) | 12.554270 | −39.570934 | 93.12 |
| semi-anthracite (sa) | 12.721190 | −43.261728 | 94.71 |
| High Seas (hvAb, hvBb, spot) | 12.864510 | −45.922948 | 97.27 |

TABLE 7-continued

L10 vs. MAF Molar Diatomic Oxygen

| Rank | $G_{OHC1}$ | $H_{OHC1}$ | $R^2$ (%) |
|---|---|---|---|
| sub-bituminous A (sub A) | 12.565156 | −40.587183 | 98.72 |
| Powder River Basin | 12.772919 | −43.423015 | 99.61 |
| sub-bituminous B (sub B) | 12.601279 | −41.266314 | 98.82 |
| sub-bituminous C (sub C) | 12.434765 | −39.130897 | 97.58 |
| Penn Bit. Waste (Glob) | 12.520164 | −40.942945 | 92.68 |
| lignite A (lig A) | 12.448910 | −39.311755 | 97.94 |
| Greek lignite | 11.922373 | −35.957530 | 99.27 |
| Irish peat | 11.763082 | −33.769078 | 98.60 |

TABLE 8

L10 vs. MAF Molar Fuel Carbon + Diatomic Hydrogen

| Rank | $G_{OHC2}$ | $H_{OHC2}$ | $R^2$ (%) |
|---|---|---|---|
| anthracite (an) | −24.934121 | 37.685859 | 94.58 |
| semi-anthracite (sa) | −31.027299 | 44.067901 | 95.90 |
| High Seas (hvAb, hvBb, spot) | −33.818323 | 47.085129 | 99.25 |
| sub-bituminous A (sub A) | −30.125654 | 43.155046 | 98.425 |
| Powder River Basin | −29.52912 | 42.485604 | 99.65 |
| sub-bituminous B (sub B) | −27.727421 | 40.593960 | 98.57 |
| sub-bituminous C (sub C) | −28.664285 | 41.636430 | 95.03 |
| Penn Bit. Waste (Glob) | −35.328433 | 48.873806 | 94.65 |
| lignite A (lig A) | −27.384762 | 40.214575 | 96.63 |
| Greek lignite | −22.184593 | 34.500349 | 99.21 |
| Irish peat | −22.438731 | 34.581539 | 97.18 |

Perhaps as expected from '877 teachings, $L_{10}$ is linear with MAF molar fuel diatomic oxygen, but also linearity is achieved with MAF molar fuel carbon plus MAF molar fuel diatomic hydrogen (as lead by multi-variant analysis). Thus Eqs.(71) and (72) may be equaled for a given group of fuels, forming an independent equation to be used in the matrix solution as based on the multi-variant relationship of Eq. (72):

$$-\xi_{L1}\alpha_{MAF-3} + \alpha_{MAF-4} + \alpha_{MAF-5} = \xi_{L2}$$

where: $\xi_{L1} \equiv H_{OHC1}/H_{OHC2}$ $\xi_{L2} \equiv (G_{OHC1} - G_{OHC2})/H_{OHC2}$ Determining Complete As-Fired Fuel Chemistry The mathematical description of the thermal system used to obtain a complete As-Fired fuel chemistry is principally described by Eqs.(30) through (34), (42), (54) and (58), all using the combustion equation Eq.(29F); details afforded in the above teachings are included. In addition, the mathematical description of the thermal system used to obtain a complete As-Fired fuel chemistry includes the teachings of this section (six paragraphs). As taught above, the genetics of fossil fuels based on multi-variant analysis has justified two independent equations which add to the matrix solution. Returning to the stoichiometrics of Eqs.(30) through (34), the following add to the 3×3, 4×4 or 5×5 matrix solution (explained below). If twice Eq.(32) is subtracted from Eq.(31), substituting for "x" via Eq.(33) results in an expression applicable for a 3×3 matrix solution:

$$-2\alpha_{MAF-3} - \xi_{C1}\alpha_{MAF-4} + \alpha_{MAF-5} + 0.0 = 0.0$$

where: $\xi_{C1} \equiv (\Gamma_{H2O} - 2\Gamma_{O2})/\Gamma_{CO2}$

For the sulfur term, combining Eq.(34) and (33) results in an expression applicable for the 4×4 or 5×5 matrix solution:

$$+0.0+\Gamma_{SO2}\alpha_{MAF-4}+0.0-\Gamma_{CO2}\alpha_{MAF-6}+0.0=0.0 \qquad (79)$$

In addition, an expression applicable for the 5×5 matrix solution is developed by substituting terms of Eq.(42) into Eq.(38) such that the term $x_{MAF}\alpha_{MAF-6}$ is incorporated into the combined Eqs.(31) & (32); reducing terms yields:

$$-2\alpha_{MAF-3} - \xi_{S1}\alpha_{MAF-4} + \alpha_{MAF-5} + 2\alpha_{MAF-6} + 0.0 = 0.0$$

where: $\xi_{S1} \equiv (\Gamma_{H2O} - 2\Gamma_{OHS} - 2\xi_{S6})/\Gamma_{CO2}$ $\xi_{S6} \equiv k_{Act}[\Gamma_{SO3}/(1.0 - \Gamma_{SO3})]/(2\Gamma_{ESP}) +$ $b_{PLS}[\sigma/2 - 1.0 - \gamma + \sigma z/2 + \sigma\Gamma_{SO3}/(2.0 - 2\Gamma_{SO3})]$ Also, the sum of all MAF molar constituents becomes applicable for the 5×5 matrix solution as it allows solution for fuel nitrogen ($\alpha_{MAF-1}$):

$$\alpha_{MAF-3}+\alpha_{MAF-4}+\alpha_{MAF-5}+\alpha_{MAF-6}+\alpha_{MAF-1}=1.0 \qquad (83)$$

It becomes obvious then that the following five equations having five unknowns (an Ultimate Analysis) may be resolved in conventional fashion using a 5×5 matrix solution:

From genetics (based on $L_{10}$), Eq.(74):

$$-\xi_{L1}\alpha_{MAF-3}+\alpha_{MAF-4}+\alpha_{MAF-5}+0.0+0.0=\xi_{L2}$$

From genetics, Eq.(64):

$$+\alpha_{MAF-3}-K_{OHC3}\alpha_{MAF-4}+\alpha_{MAF-5}+0.0+0.0=J_{OHC3}$$

From stoichiometrics, Eq.(80):

$$-2\alpha_{MAF-3}-\xi_{S1}\alpha_{MAF-4}+\alpha_{MAF-5}+2\alpha_{MAF-6}+0.0=0.0$$

From stoichiometrics, Eq.(79):

$$+0.0+\Gamma_{SO2}\alpha_{MAF-4}+0.0-\Gamma_{CO2}\alpha_{MAF-6}+0.0=0.0$$

From stoichiometrics (MAF balance), Eq.(83):

$$+\alpha_{MAF-3}+\alpha_{MAF-4}+\alpha_{MAF-5}+\alpha_{MAF-6}+\alpha_{MAF-1}=1.0.$$

However, the above system of equations may be reduced given situations unique to a given thermal system. If little fuel nitrogen is present (or it is highly predictable), then four equations having four unknowns (an Ultimate Analysis less nitrogen) may be resolved in using a 4×4 matrix solution, nitrogen being held constant or equated to $(1.0 - \Gamma_{j=3,4,5,6}\alpha_{MAF-j})$:

From genetics (based on $L_{10}$), Eq.(74):

$$-\xi_{L1}\alpha_{MAF-3}+\alpha_{MAF-4}+\alpha_{MAF-5}+0.0=\xi_{L2}$$

From genetics, Eq.(64):

$$+\alpha_{MAF-3}-K_{OHC3}\alpha_{MAF-4}+\alpha_{MAF-5}+0.0+0.0=J_{OHC3}$$

From stoichiometrics, Eq.(77):

$$-2\alpha_{MAF-3}-\xi_{C1}\alpha_{MAF-4}+\alpha_{MAF-5}+0.0=0.0$$

From stoichiometrics, Eq.(79):

$$+0.0+\Gamma_{SO2}\alpha_{MAF-4}+0.0-\Gamma_{CO2}\alpha_{MAF-6}=0.0.$$

Further, if both fuel nitrogen and fuel sulfur are either highly predictable (and/or the fuel contains no sulfur), then three equations having three unknowns comprising the base Oxy-Hydrocarbon model as an intrinsic out-come of the genetics of fossil fuels, may then be resolved using a 3×3 matrix solution. Specifically, sulfur may be held constant, including zero, or resolved via Eq.(34) after determining $\alpha_{MAF-4}$ from the 3×3 matrix solution.

From genetics (based on $L_{10}$), Eq.(74):

$$-\xi_{L1}\alpha_{MAF-3}+\alpha_{MAF-4}+\alpha_{MAF-5}=\xi_{L2}$$

From genetics, Eq.(64):

$$+\alpha_{MAF-3}-K_{OHC3}\alpha_{MAF-4}+\alpha_{MAF-5}=J_{OHC3}$$

From stoichiometrics, Eq.(77):

$$-2\alpha_{MAF-3}-\xi_{C1}\alpha_{MAF-4}+\alpha_{MAF-5}=0.0.$$

Such collections of equations for the aforementioned matrix solutions are certainly not unique, to one skilled several variations will become apparent given any study. For example the above 3×3 matrix solution obviously may invoke Eq.(83) such that its right-hand side is constant; i.e., known and constant nitrogen ($\alpha_{MAF-1}$) and constant sulfur ($\alpha_{MAF-6}$):

From genetics, Eq.(64):

$$+\alpha_{MAF-3}-K_{OHC3}\alpha_{MAF-4}+\alpha_{MAF-5}=J_{OHC3}$$

From stoichiometrics, Eq.(77):

$$-2\alpha_{MAF-3}-\xi_{C1}\alpha_{MAF-4}+\alpha_{MAF-5}=0.0$$

From stoichiometrics (MAF balance), Eq.(83):

$$+\alpha_{MAF-3}+\alpha_{MAF-4}+\alpha_{MAF-5}=(1.0-\alpha_{MAF-1}-\alpha_{MAF-6}).$$

As another example, the 4×4 matrix solution may also employ the MAF balance of Eq.(83), replacing the $L_{10}$ relationship, by setting $\alpha_{MAF-1}$ constant; the right-hand side of Eq.(83) becoming $(1.0-\alpha_{MAF-1})$ after re-arranging. Although the 5×5 matrix solution, involving all MAF fuel constituents, is the Preferred Embodiment, the ERR-CALC and HEATRATE programs are provided with an input option which selects which of these matrix solutions is to be employed. Such selection is based principally on the predictability of the nitrogen and sulfur fuel components (e.g., knowing whether the fuel has sulfur); of course when employing the 5×5 matrix solution, such judgement is not required. In summary, the operator of the thermal system or a vendor selling to said operator may be using the genetics of the fossil fuel based on multi-variant analysis as taught herein, and may be using a mathematical description of the thermal system as taught herein to improve the system. On the other hand, the operator of the thermal system or a vendor selling to said operator may be developing the genetics of the fossil fuel based on multi-variant analysis as taught herein and may be developing a mathematical description of the thermal system based on the teachings herein to improve the system.

Once the Ultimate Analysis of MAF fuel constituents is resolved, MAF fuel moles may be computed from Eq.(56): $x_{MAF}=\Gamma_{CO2}/\alpha_{MAF-4}$. With the Ultimate Analysis of MAF fuel constituents known, with MAF fuel water of Eq.(42) and, with $x_{MAF}$, $AF_{Act}$ and "a", MAF fuel ash of Eq.(54) may then be resolved in an explicit manner, or otherwise obtained. To summarize, the matrix solutions presented in the preceding four paragraphs employ results from the genetics of the fossil fuel, based on multi-variant analysis, and employ mathematical description of the thermal system based on stoichiometrics. Terms are not mixed. The features incorporated into the matrix solutions presented in the preceding three paragraphs—representing a considerable inventive step beyond '994—include:

the use of multi-variant analysis resulting in applying at least one of the relationships described by Eqs.(61), (62), (63), and (71) combined with (72);

the genetics for all important Ranks of coal is listed in TABLES 2, 3, 4, 7 and 8, eliminates the need for routine historical data;

$R^2$ values typically exceed 98%, allowing the genetics of the fossil fuel of interest to be used to interrogate laboratory results;

the mathematical description does not intermingle correlation constants (resultant from multi-variant analysis) with stoichiometric terms, i.e., Eqs.(77), (79), (80) and (83) contain only stoichiometric terms free of regression constants for fossil fuel;

fuel nitrogen need not be kept constant (when using the 5×5 matrix solution);

the need for minimum and maximum limits applied to fuel concentrations is obviously eliminated since the computed MAF constituents must satisfy all equations in the matrix solution, numerical consistency is intrinsic.

Thus all fuel constituents, and the fuel moles, are therefore determined on a MAF basis. From these values, the wet base molar fuel fractions are then determined, as are the wet base moles of fuel (x) and the wet base (As-Fired) weight fractions ($WF_j$) of all fuel constituents j:

$$\alpha_j=\alpha_{MAF-j}/(1.0+\alpha_{MAF-2}+\alpha_{MAF-10}) \quad (90)$$

$$x=x_{MAF}(1.0+\alpha_{MAF-2}+\alpha_{MAF-10}) \quad (91)$$

$$x\alpha_j=x_{MAF}\alpha_{MAF-j} \quad (92)$$

$$WF_j=\alpha_j N_j/(\Sigma \alpha_j N_j) \quad (93)$$

$$WF_{DRY-j}=WF_j/(1.0-WF_2) \quad (94)$$

Determining Calorific Value, Boiler Efficiency, Fuel and Effluent Flows

This section includes the mathematical description of the thermal system used to obtain a calorific value, boiler efficiency, fuel and effluent flows. Having obtained a complete As-Fired fuel chemistry, the fuel's calorific value (i.e., heating value) is next computed. Following the teachings of '994, calorific value is determined based on a differential analysis. References are cited in '994. Note that the term $N_{MAF}$ is the molecular weight of the MAF-base fuel (without fuel water and without fuel ash).

For calorific value units of measure in kJ/kg:

$$\Delta HHV_{MAF-delta} = HHV_{MAF-Ref} - \\ \frac{(-414928.58\alpha_{MAF-3} + 427034.81\alpha_{MAF-4} + 181762.20\alpha_{MAF-5} + 297011.59\alpha_{MAF-6})_{Ref}}{N_{MAF-Ref}} \quad (98A)$$

$$HHV_{MAF-uncorr} = \\ \frac{(-414928.58\alpha_{MAF-3} + 427034.81\alpha_{MAF-4} + 181762.20\alpha_{MAF-5} + 297011.59\alpha_{MAF-6})_{Actual}}{N_{MAF-Actual}} \quad (99A)$$

For calorific value units of measure in Btu/lbm:

$$\Delta HHV_{MAF-delta} = HHV_{MAF-Ref} - \\ \frac{(-178387.18\alpha_{MAF-3} + 183591.92\alpha_{MAF-4} + 78143.68\alpha_{MAF-5} + 127692.00\alpha_{MAF-6})_{Ref}}{N_{MAF-Ref}} \quad (98B)$$

$$HHV_{MAF-uncorr} = \\ \frac{(-178387.18\alpha_{MAF-3} + 183591.92\alpha_{MAF-4} + 78143.68\alpha_{MAF-5} + 127692.00\alpha_{MAF-6})_{Actual}}{N_{MAF-Actual}} \quad (99B)$$

$$HHV_{MAF} = HHV_{MAF-uncorr} + \Delta HHV_{MAF-delta} \quad (100)$$

$$HHV_{DRY} = HHV_{MAF}(1.0 - WF_{DRY-10}) \quad (101)$$

$$HHV_{AF} = HHV_{DRY}(1.0 - WF_2) \quad (102)$$

The preferred correlations used to determine calorific values for the present invention are based on chemical binding energies. Studies have demonstrated that traditional correlations, such as the Mott-Spooner correlation based on Dulong's formula—well known in the industry—are not adequate. The Preferred Embodiment of the present invention requires at least the coefficients used in determining calorific value to fall within certain ranges associated with three principal constituents of coal. Studies have indicated that using the above preferred constants, which fall within the required ranges, reduces the standard deviation of five dozen wildly varying coal analyses from ±530 to ±214 ΔkJ/kg (±228 to ±92 ΔBtu/lbm, i.e., ΔBtu/pound). The ranges of these coefficients, i.e., multiples the molar fractions $\alpha_j$ in Eqs.(98A) and (99A), for units of kJ/kg, or their equivalent weight fractions (for this presentation of ranges, the symbol $WF_j$ represents percent weight of j), include the following: for carbon molar fraction $390358\alpha_{carbon}/N_{fuel}$ to $429994\alpha_{carbon}/N_{fuel}$, or in weight percent carbon, $325WF_{carbon}$ to $358WF_{carbon}$; for hydrogen molar fraction $180623\alpha_{hydrogen}/N_{fuel}$ to $293109\alpha_{hydrogen}/N_{fuel}$ assuming the diatomic hydrogen, or in weight percent hydrogen, $896WF_{hydrogen}$ to $1454WF_{hydrogen}$; and for also for oxygen molar fraction $-275190\alpha_{oxygen}/N_{fuel}$ to $-579178\alpha_{oxygen}/N_{fuel}$ assuming diatomic oxygen, or in weight percent oxygen, $-86WF_{oxygen}$ to $-181WF_{oxygen}$. These ranges are independent of the fuel base, whether MAF, dry or As-Fired fuel constituents are used. Also, the ranges of these coefficients, i.e., multiples the molar fractions $\alpha_j$ in Eqs.(98B) and (99B), for units of Btu/lbm, or their equivalent weight fractions (for this presentation of ranges, the symbol $WF_j$ represents percent weight of j), include the following: for carbon molar fraction $168154\alpha_{carbon}/N_{fuel}$ to $184969\alpha_{carbon}/N_{fuel}$, or in weight percent carbon, $140WF_{carbon}$ to $154WF_{carbon}$; for hydrogen molar fraction $77611\alpha_{hydrogen}/N_{fuel}$ to $125993\alpha_{hydrogen}/N_{fuel}$ assuming diatomic hydrogen, or in weight percent hydrogen, $385WF_{hydrogen}$ to $625WF_{hydrogen}$; and for the oxygen molar fraction $-118396\alpha_{oxygen}/N_{fuel}$ to $-249591\alpha_{oxygen}/N_{fuel}$ assuming diatomic oxygen, or in the weight percent oxygen, $-37WF_{oxygen}$ to $-78WF_{oxygen}$. These ranges are independent of the fuel base, whether MAF, dry or As-Fired fuel constituents are used.

Boiler efficiency is defined as either gross calorific based, $\eta_{B-HHV}$ (i.e., higher heating value, HHV), or net calorific based, $\eta_{B-LHV}$ (i.e., lower heating value, LHV). In the Preferred Embodiment boiler efficiency is determined using the methods of '429. Another of the Input/Loss methods may be used to determine boiler efficiency, provided consistency between boiler efficiency, fuel flow and effluent flow is maintained. The details of such consistency is thoroughly discussed in '994. In addition to '429, the following procedures for determining boiler efficiency have sufficient accuracy and consistency for use by this invention: the American Society of Mechanical Engineers' (ASME) Performance Test Codes (PTC) 4.1 and 4; the German standard "Acceptance Testing of Steam Generators, DIN 1942, DIN DEUTSCHES Institut Fur Normung E.V., February 1994; the European standard (draft) prEN 12952-15:1999 (also: CEN/TC 269/WG 3 N 337), "Water-Tube Boilers and Auxiliary Installations—Part 15: Acceptance Tests", November 1999, European Committee for Standardization, Central Secretariat, rue de Stassart, 36, Brussels; and the British Standard "Code for Acceptance Tests on Stationary Steam Generators of the Power Station Type", BS 2885:1974, ISBN: 0 580 08136 2.

As taught in '429, and considered important for this invention, is that the As-Fired fuel flow compute identically from either efficiency base:

$$m_{AF} = \frac{BBTC}{\eta_{B-HHV}(HHVP+HBC)} = \frac{BBTC}{\eta_{B-LHV}(LHVP+HBC)} \quad (103)$$

For Eq.(103), such computations, if following the Preferred Embodiment, required that: 1) the Firing Correction term HBC be employed; 2) the calorific values be properly corrected, if needed, for a constant pressure process (resulting in HHVP or LHVP); and 3) the calorimetric temperature, $T_{Cal}$, be consistently employed in all terms making up boiler efficiency. All of these teachings may be found in '429. However, this invention is not limited to the use Eq.(103) and the HBC term (although preferred), as many of the industrial standards to set HBC to zero and use methods other than '429 to compute boiler efficiency; the important criteria is to maintain consistency of use when determining fuel flow, effluent flow, etc. based on boiler efficiency, BBTC and calorific value.

Knowing the complete As-Fired fuel chemistry leads to a high accuracy boiler efficiency, a boiler efficiency which in-turn leads to system efficiency. The systems' over-all thermal efficiency is defined in a consistent manner, as taught in '994. System thermal efficiency is also expressed in-terms of heat rate, HR (kJ/kWh or Btu/wKh, i.e. Btu/kilowatt-hour), the reciprocal of efficiency with units conversion.

$$\eta_{SYS-HHV} = W_{output} / [m_{AF}(HHVP+HBC)] \quad (104A)$$

$$= W_{output}\eta_{B-HHV} / BBTC \quad (104B)$$

$$\eta_{SYS-LHV} = W_{output} / [m_{AF}(LHVP+HBC)] \quad (105A)$$

$$= W_{output}\eta_{B-LHV} / BBTC \quad (105B)$$

For heat rate units of kJ/kWh:

$$HR_{HHV} = 3600.0000/\eta_{SYS-HHV} \quad (106A)$$

$$HR_{LHV} = 3600.0000/\eta_{SYS-LHV} \quad (106B)$$

For heat rate units of Btu/kWh:

$$HR_{HHV} = 3412.1416/\eta_{SYS-HHV} \quad (107A)$$

$$HR_{LHV} = 3412.1416/\eta_{SYS-LHV} \quad (107B)$$

By knowing the complete As-Fired fuel chemistry and the As-Fired fuel flow, and using a mathematical description of the thermal system based on stoichiometrics, individual effluent flows, $m_{species-i}$ (kg/hr or lb/hr), may then be determined:

$$m_{species-i} = m_{AF}\Phi_i N_i / (xN_{AF}) \quad (108)$$

where $\Phi_i$ is the moles of an effluent species on a dry-basis; i.e., $\Phi_i$ is the effluent concentration in moles. The term $\Phi_i$ derives directly from solutions or measurements of the right-hand terms of Eq.(29F), for example $\Phi_{SO2}=k_{Act}$. To determine the total effluent flow, Eq.(108) may be summed, noting that $\Sigma\Phi_i=100.0$ moles. Individual emission rates, termed $ER_i$, in units of measure following those of reciprocal calorific value (kg-effluent/million-kJ, or pounds-effluent/million-Btu of fuel energy input), is given by the following:

$$ER_i = 10^6 m_{species-i} / (m_{AF}HHV_{AF}) \quad (109A)$$

$$= 10^6 \Phi_i N_i / (xN_{AF}HHV_{AF}) \quad (109B)$$

As seen, an individual emission rate may be evaluated independently of the As-Fired fuel flow, Eq.(109B). However, the computational accuracy of the fuel flow, as determined using the present approach, intrinsically affects an individual emission rate through $HHV_{AF}$, x and $N_{AF}$. Further, the process described herein allows the determination of total effluent dry volumetric flow, at standard conditions of gaseous effluent, denoted by VF, as required by environmental regulations. VF is determined by the following (in standard-m³/sec or standard-ft³/hr):

$$VF = \rho_{gas} m_{AF} N_{gas} / (xN_{AF}) \quad (110)$$

where $\rho_{gas}$ and $N_{gas}$ are the standard density and average molecular weight of the effluent dry gas.

Correction of Choice Operating Parameters and System Benchmarking

This section includes the mathematical description of the thermal system used to obtain a multidimensional minimization analysis. This invention recognizes that those products from combustion which are used to determine a complete As-Fired fuel chemistry, as measured by routine power plant instrumentation, may have error associated with their signals. As taught herein, quantities employed to determine fuel chemistry consist not only of the principle effluents $CO_2$, $H_2O$ and $O_2$ but also the Air Pre-Heater Leakage Factor, etc. This invention has defined Choice Operating Parameters (COP) as all parameters which may directly impact system stoichiometrics, and thus may impact the determination of fuel chemistry. To correct errors in COPs one of two methods may be employed: 1) apply judgement based on a power engineer's experience with a particular instrument (e.g., plot signals vs. time, compare multiple signals reading the same value, etc.); and 2) use the methods as taught in '877. For the Preferred Embodiment, '877 methods are herein modified as follows. First, the use of the L Factor as a System Effect Parameter (SEP) must not employ $L_5$, but $L_{10}$ as defined via Eq.(70). Second, '877 methods must recognize that the relative humidity associated with the combustion air represents a significant sensitivity to system stoichiometrics when employing the methods of this invention. Third, a modified Objective Function has shown to be better suited for the genetics of fossil fuels. In the Preferred Embodiment, COPs may be selected by the power plant engineer from any combination or all of the following:

$\Lambda_{1S}=d_{Act}$; Stack $CO_2$ (with effects from Air Pre-Heater leakage) (111S)

$\Lambda_{1B}=d_{Act}R_{Act}$; Boiler $CO_2$ (without effects from Air Pre-Heater leakage) (111B)

$\Lambda_{2S}=J_{Act}=j+b_A\beta$; Stack $H_2O$ (with $H_2O$ from Air Pre-Heater leakage) (112S)

$\Lambda_{2B}=j\ R_{Act}$; Boiler $H_2O$ (without $H_2O$ from Air Pre-Heater leakage) (112B)

$\Lambda_3=AF$; Air/Fuel ratio (for explicit determination of fuel ash) (113)

$\Lambda_4=R_{Act}$; Air Pre-Heater Leakage Factor (114)

$\Lambda_5 = A_{Act}$; Concentration of $O_2$ in the combustion air (115)

$\Lambda_6 = m_{LS}$; System's indicated plant limestone flow (116)

$\Lambda_{7S} = G_{Act} \equiv g + \alpha\beta$; Stack $O_2$ (with Air Pre-Heater leakage) (117S)

$\Lambda_{7B} = g\ R_{Act}$; Boiler $O_2$ (without Air Pre-Heater leakage) (117B)

$\Lambda_8 = m_T$; Tube leakage flow rate (118)

$\Lambda_9 = H_{Act}$; Relative humidity of ambient air local to the thermal system (119)

Selecting one or more of the Choice Operating Parameters for use must depend on common understanding of power plant stoichiometrics and associated relationships to physical equipment. What the ERR-CALC program produces (FIG. 20B, item 255), employing one or more of the minimization techniques as taught by '877, are correction factors, for each chosen $\Lambda_k$ which are then applied to the raw uncorrected signal ($\Lambda_{0-k}$). The resulting corrected signal is then processed within the Fuel Iterations, defined in conjunction with a description of FIG. 20. A multidimensional minimization analysis includes driving an Objective Function, $F(\vec{x})$, to a minimum value (ideally zero), by optimizing COPs. Although COPs ($\Lambda_k$) values do not appear in the Objective Function, they directly impact SEPs directly. SEPs are driven towards Reference System Effect Parameters by the following:

$$\lambda_L \equiv [(L_{10} - L_{10\text{-}Ref})/L_{10\text{-}Ref}] \quad (120A)$$

$$\lambda_W \equiv [(m_{AF} - m_{AF\text{-}PLT})/m_{AF\text{-}PLT}] \quad (120B)$$

$$\lambda_H \equiv [(HHV_{AF} - HHV_{AF\text{-}Ref})/HHV_{AF\text{-}Ref}] \quad (120C)$$

$$\lambda_F \equiv [(WF_{H2O} - WF_{H2O\text{-}Ref})/WF_{H2O\text{-}Ref}] \quad (120D)$$

In these equations The Objective Function most useful for the methods and apparatus of this invention is given by Eq.(121). Note that the Bessel function of the first kind of order zero ($J_0$) is highly suited to the sensitivities found in coal-fired stoichiometrics.

$$F(\vec{x}) = \Sigma_{k \in K}\{S_i[1.0 - J_0(\lambda_L)]^{MC_k} + S_i[1.0 - J_0(\lambda_W)]^{MC_k} + S_i[1.0 - J_0(\lambda_H)]^{MC_k} + S_i[1.0 - J_0(\lambda_F)]^{MC_k}\} \quad (121)$$

In Eq.(121), the symbol $MC_k$ is termed a Dilution Factor (whose concept was introduced in '877), but here assigned individually by COP resulting in greater solution stability. In Eq.(121) $S_k$ is a scaling factor accounting for differing numerical magnitudes of $\lambda_j$. In Eq.(121), the symbol $\Sigma_{k \in K}$ indicates a summation on the index k, where k variables are contained in the set K defined as the elements of $\vec{\Lambda}$. For example, assume the user has chosen the following: $\Lambda_{1S}$ is to be optimized to minimize the error in $L_{10}$ and $HHV_{AF}$, $\Lambda_{2S}$ is optimized for $L_{10}$ and $m_{AF}$ ($M_W$=1.40), $\Lambda_4$ is optimized for $L_{10}$, and $\Lambda_{7B}$ is optimized for $L_{10}$. Therefore:

$\vec{\Lambda} = (\Lambda_{1S},\ \Lambda_{2S},\ \Lambda_4,\ \Lambda_{7B})$, $K = \{\Lambda_{1S},\ \Lambda_{2S},\ \Lambda_4,\ \Lambda_{7B}\}$, thus $\vec{x} = (x_1,\ x_2,\ x_3,\ x_4)$; $x_1 = S_1\Lambda_{1S}$; $x_2 = S_2\Lambda_{2S}$; $x_3 = S_3\Lambda_4$; $x_4 = S_4\Lambda_{7B}$; where Eq.(121) for this example then becomes:

$$F(\vec{x}) = S_1\{[1.0 - J_0(\lambda_L)]^{MC_1} + [1.0 - J_0(\lambda_H)]^{MC_1}\} + S_2\{[1.0 - J_0(\lambda_L)]^{MC_2} + [1.0 - J_0(\lambda_W)]^{MC_2}\} + S_3[1.0 - J_0(\lambda_L)]^{MC_3} + S_4[1.0 - J_0(\lambda_L)]^{MC_4}$$

Upon optimization, COP correction factors ($C_k$) are determined simply as: $C_k = \Lambda_k / \Lambda_{0-k}$. Note that the only output from ERR-CALC are correction factors.

The consistency demonstrated herein by the genetics of the fossil fuels, as implemented by this invention for the determination of fuel chemistry, has proven of such remarkable consistency and accuracy that, it is believed, ambient relative humidity may offer a vehicle through which a power plant's monitoring system may be benchmarked. This statement is saying that a system's stoichiometrics (i.e., fuel chemistry versus effluent production of $CO_2$, $H_2O$, $O_2$, etc., determined by The Input/Loss Method) may be verified using an independent parameter associated with combustion, ambient relative humidity, which is not directly influenced by the understanding (or not) of fuel chemistry, fuel flow and boiler efficiency. However, a relative humidity computed by The Input/Loss Method is indeed greatly affected by fuel chemistry, an understood system stoichiometrics and calorific value; such sensitivity on the computed is extreme. As a practical application, use of this benchmarking technique would verify reported carbon emissions based on the monitoring system's ability to replicate an environmental parameter which would be measured by all parties, both regulator and the system operator. Of course other air psychrometric parameters such as specific humidity, web bulb temperature, etc. might be used, but relative humidity as ranging from 0.0 to 100% is most convenient for '877 optimization procedures.

Figure 21:
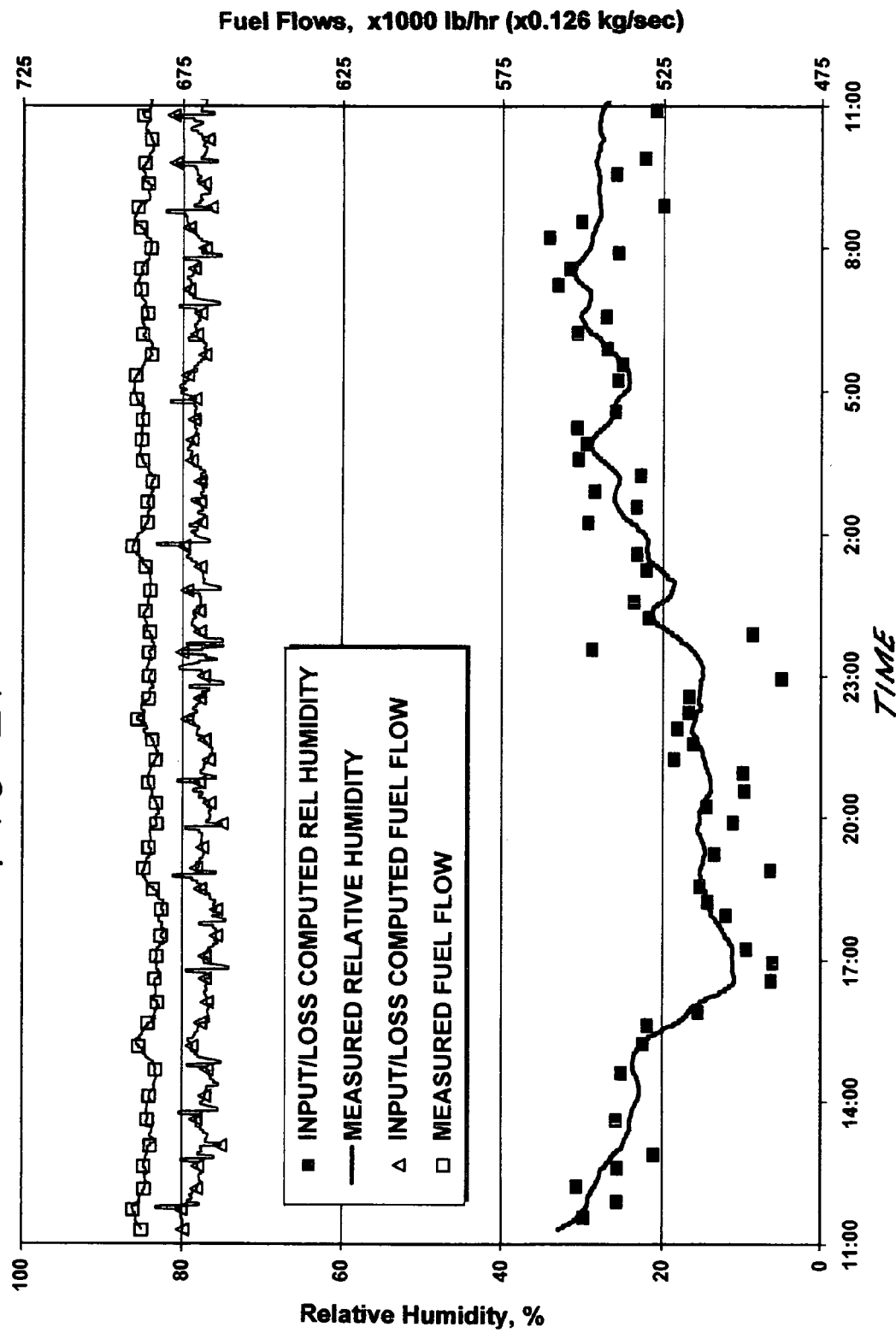
FIG. 21 is a plot of an emulation of a power plant, using the methods taught herein, in which the system's measured relative humidity is being essentially matched by a computed relative humidity demonstrating stoichiometric understanding. The indicated plant fuel flow was demonstrated to have a bias of 2.4%.

The procedure for benchmarking an on-line monitoring system is thus: 1) monitor the power plant such that SEP for the plant's indicated plant fuel flow is invoked, optimizing on both the COP for effluent $H_2O$ ($\Lambda_{2S}$), and the COP for relative humidity ($\Lambda_9$); 2) set to a constant the input of relative humidity to The Input/Loss Method; 3) ERR-CALC, using '877 methods modified as above, will produce correction factors for both $\Lambda_{2S}$ and $\Lambda_9$; 4) bias the plant's indicated plant fuel flow until the corrected relative humidity computed by The Input/Loss Method agrees with a directly measured (and independent) value. When agreement is reached, fuel chemistry, fuel calorific value (CV, dependent on fuel chemistry), boiler efficiency (dependent on fuel chemistry and CV) and the energy flow to the working fluid heated by combustion products (BBTC) all must be accurate. Given this, all emission flows, e.g., carbon emission, must be accurately computed; it may be nothing else. As an example of such benchmarking FIG. 21 is a plot of an emulation of a power plant and its data in which the system's measured relative humidity is being matched by a computed relative humidity. FIG. 21 demonstrates stoichiometric understanding. Plotted are comparisons between the indicated plant fuel flow and the computed. Note that upset marks on the computed fuel flow trace represent interruptions in which fuel flow bias was being adjusted. An emulation of an actual system was employed for FIG. 21 since certain patent offices do not allow demonstration of invention before filing. The indicated plant fuel flow was shown to have an average bias of 2.41%.

Calculational Engine Apparatus for Input/Loss Methods

Obtaining a complete As-Fired fuel chemistry, including fuel water and fuel ash (as based on: a) using a genetics of the fossil fuel based on multi-variant analysis; b) using a mathematical description of the thermal system; c) measuring a set of measurable Operating Parameters, including at least effluent concentrations of $O_2$ and $CO_2$, these measurements being made at a location downstream of the heat exchanger/combustion region of the thermal system; d)

obtaining an effluent concentration of $H_2O$, as an obtained effluent $H_2O$; e) obtaining a fuel ash concentration selected from the group consisting of: a constant value of fuel ash, a predictable value of fuel ash, a measured value of fuel ash determined from a fuel ash instrument and a value of fuel ash determined from explicit solution, as an obtained fuel ash concentration; f) obtaining a concentration of $O_2$ in the combustion air local to the system; and g) obtaining the Air Pre-Heater Leakage Factor), may be incorporated into a fuel chemistry determining apparatus to improve the understanding of fossil-fueled thermal systems, including a produced output provided from associated analytical models dependent on fuel chemistry. The produced output from the apparatus includes the fuel's calorific value (CV, dependent on fuel chemistry), boiler efficiency (dependent of fuel chemistry and CV), fuel flow per Eq.(103), and system efficiency of Eqs.(104) & (105). The produced output from the apparatus thereby provides a means to assist the operator of the thermal system in the monitoring and improvement of system efficiency on a continuous operating basis such as would be used for the on-line monitoring of power plants.

In summary, this invention includes an apparatus for assisting the operation of a thermal system burning a fossil fuel, the apparatus comprising: a) a data acquisition device to collect data from the thermal system including at least a selection of Choice Operating Parameters, the data acquisition device producing a set of system acquired data; b) a computer with a processing means; c) a set of instructions for configuring the processing means to determine a fuel chemistry of the fossil fuel and to receive as input the set of system acquired data, resulting in a programmed computer; d) means by which the programmed computer receives as input the set of system acquired data; e) the programmed computer producing the fuel chemistry of the fossil fuel; and f) means for reporting the fuel chemistry of the fossil fuel to an operator of the thermal system. The aforementioned computer may be a common personal computer, or, broadly, any data processing unit. In addition, set of instructions for configuring the processing means to determine a fuel chemistry of the fossil fuel includes programming the teachings of this invention including the genetics of the fossil fuel, the mathematical description of the thermal system, determination of an Ultimate Analysis of the fossil fuel, and determination of a complete As-Fired fuel chemistry.

CONCLUSION

Although the present invention has been described in considerable detail with regard to certain Preferred Embodiments thereof, other embodiments within the scope and spirit of the present invention are possible without departing from the general industrial applicability of the invention. For example, the descriptions of this invention assume that a steam generator's working fluid is water, however the general procedures of this invention may be applied to any type of working fluid provided that the working fluid is definable at the boundary of the system. Examples of other working fluids are: mixtures of water and organic fluids, organic fluids, liquid metals and so forth. Further, the concept of multi-variant analysis leading to the genetics of fossil fuels was presented with two elements (any two elements of the group consisting of carbon, hydrogen and oxygen), which is the Preferred Embodiment. However, this invention is not to be limited by this concept. Multi-variant analysis leading to the genetics of fossil fuels may well employ three elements in any combination: carbon, hydrogen, oxygen and sulfur. For example, Eq.(61) might be replaced with: $\alpha_{MAF-4} + \alpha_{MAF-5} + \alpha_{MAF-6} = J'_{OHC1} + K'_{OHC1} \alpha_{MAF-3}$; thus forming a (carbon+hydrogen+sulfur) fit versus oxygen. Indeed, success has been had with such employments. Accordingly, the general theme and scope of the appended claims should not be limited to the descriptions of the Preferred Embodiment disclosed herein.

Although a Preferred Embodiment of the present invention has been demonstrated via THE DRAWINGS and described in considerable detail the foregoing DESCRIPTION OF THE PREFERRED EMBODIMENT, it will be understood that the invention is not limited to the embodiments disclosed, but those methods are capable of numerous rearrangements, modifications and substitutions without departing from the scope and spirit of the present invention as set forth and defined by the claims herein.

The Drawings

The FIGS. 1 through 18, and FIG. 21 have been discussed in detail within the foregoing DESCRIPTION OF THE PREFERRED EMBODIMENT. Analytical findings of these FIGURES are presented in TABLES 2, 3, 4, 7 and 8. TABLE 6 presents generic chemical makeups of numerous fossil fuels, when normalized to carbon in the form $CH_{c2}O_{c3}$.

FIG. 19 is a schematic representation of a thermal system, particularly a steam generator system illustrating use of stoichiometric relationships important in applying this invention. It should be studied in conjunction with combustion equation, Eq.(29F). FIG. 19 depicts a steam generator denoted as 20. In this system 20, a fuel feed 22 and combustion air 24 are all provided to the upstream side region 26 of the heat exchanger/combustion region 28. Note that this region 28 does not include the air pre-heater 36. In addition, in some types of steam generators 20 such as fluidized bed combustors, other materials may be injected into region 26, such as a flow of limestone 31 to minimize effluent $SO_2$ by chemically binding sulfur as $CaSO_4$. Other sorbents may be injected to control sulfur, to control other pollutants, and/or to control the combustion process. The fuel feed 22 contains, in general, combustible fossil material, water and mineral matter (commonly called ash); 22 represents an As-Fired fuel given it is the fuel being burned after crossing the system boundary 44. Fuel ash is an unburnable component that passes through the system with little physical change, but which is heated and cooled. In the heat exchanger/combustion region 28, the steam generator's fuel 22 is burned with the combustion air 24 to form hot products of combustion. Heat from the products of combustion is transferred to a working fluid that enters 134 heat exchangers 132 that are depicted as integral with the heat exchanger/combustion region 28. The heated working fluid 130 is used in a manner appropriate to a working fluid to generate a useful output 33 (for example, in a conventional power plant such useful output, BBTC, may be supplied to a turbine-generator cycle for the production of electrical power, $W_{output}$). Heat exchangers 132 may consist of a series of heat exchangers. There may be working fluid leakage 29 into the products of combustion 28 and into region 35, not associated with water in the fuel feed 22, or moisture in the combustion air 24. Working fluid leakage 29 consists of known flows, or flows which may be otherwise reasonably assumed or determined; and may result from, for example, soot blowing associated with coal-fired systems, or working fluid used to atomize the fuel 22 before combustion, or used in pollutant control processes located at 35 or 42. The products of combustion leave the heat exchanger/combustion region 28 on its downstream region 34, the cooler products of combustion then commonly flow through ducts, region 35, which may contain fly ash removal equipment, passing then to an air pre-heater 36, where a further portion of the combustion gas energy is transferred to an incoming air stream 38, which air then becomes the combustion air 24. The total air delivered to 20 is the incoming air flow 25. In many cases, an air leakage flow 40 enters the flow of the products of combustion as it passes through the air pre-heater 36. The further cooled products of combustion leave the air pre-heater 36 and pass to the Stack 42, the gases then being exhausted to the local environment 43. Within the steam generator system 20 the combustion gas path is defined as that region encompassing the flow of products of combustion, said products also termed combustion gases, generally occupying regions 28, 35, the gas side of 36, and 42, exiting as 43.

FIG. 19, given its general system description provided above, is applicable to a wide variety of fossil-fired systems including a coal-burning power plant, an oil-burning power plant, a gas-fired power plant, a biomass combustor, a fluidized bed combustor, a conventional electric power plant, a steam generator, a package boiler, a combustion turbine, a combustion turbine with a heat recovery boiler, a peat burning power plant, and a Recovery Boiler used in the pulp and paper industry. This list is not meant to be exhaustive, however, and is presented to illustrate some of the areas of applicability of the present invention which encompass any thermal system burning a fossil fuel and which has at least one heat exchanger whose working fluid is being heated by the products of combustion. This invention is applicable to a wide variety of Input/Loss methods.

Within fossil-fired systems, some quantities are readily measured with adequate accuracy, and others may not be measured on-line (in real time) with accuracy sufficient to quantify the operation of the system 20 to the required accuracy to optimize efficiency. For example, working fluid flows, pressures and temperatures may be readily measured with good accuracy by conventional sensors located at defined boundaries such as 134, 130, 25, 33, 42, 29 and 31. Choice Operating Parameters all may, under ideal conditions, be directly measured with common industrial accuracy either in real time or periodically, then corrected using the methods of '877 if required. In FIG. 19 quantities which may be (or are) Choice Operating Parameters include: the combustion gas concentrations in the regions 35 and 42 (including $CO_2$, $H_2O$, and $O_2$, termed $\Lambda_{1B}$, $\Lambda_{2B}$, $\Lambda_{7B}$ at region 35, and $\Lambda_{1S}$, $\Lambda_{2S}$, $\Lambda_{7S}$ at region 42); the indicated combustion air flow 24 (when combined with indicated plant fuel flow 22 then allows the Air/Fuel ratio to be determined, $\Lambda_3$, which allows the fuel ash fraction to be computed); the ratio of gas concentrations across the air pre-heater, regions 35 and 42 (either the $O_2$ or the $CO_2$ ratio across these regions, preferably the $CO_2$ ratio, thus allowing the Air Pre-Heater Leakage Factor $R_{Act}$ to be determined, $\Lambda_4$); the concentration of $O_2$ in the combustion air local to the system 25 (termed $A_{Act}$, or $\Lambda_5$, allowing $\phi_{Act}$ to be determined); the indicated plant limestone flow 31 ($\Lambda_6$); and the relative humidity associated with the combustion air local to the system 25 ($\Lambda_g$). In addition, another Choice Operating Parameter is tube leakage flow, not shown ($\Lambda_8$), which may be determined by optimizing the fuel's average water content in the fuel or using the computed As-Fired fuel flow ($m_{AF}$); when optimized, the tube leakage flow becomes defined, consistent with stoichiometrics of Eqs.(29F) through the term $b_Z$. Refer to Eqs.(111S) through (119). This invention teaches to employ '877 methods to correct such measurements or their assumptions if such measurements are not available.

FIG. 20 illustrates an important portion of this invention, specifically the general calculational sequences associated with The Input/Loss Method. Boxs 110, 120 and 130 represents general data initialization steps including using or developing a genetics of the fossil fuel, data collection, data organization and routine set-ups of all programs. Box 250 initiates continuous on-line monitoring of a thermal system. Box 255 depicts obtaining a set of correction factors for Choice Operating Parameters by either applying judgement based on a power engineer's experience with a particular instrument resulting in a set of obtained correction factors, or through use of the ERR-CALC program resulting in a set of correction factors based on a multidimensional minimization analysis (whose methods are taught herein, and further discussed in '877). If correction factors are not to be updated at the same frequency as the Fuel Iterations (defined below), Box 255 is bypassed; and, if bypassed, its previously computed correction factors are applied to $\Lambda_{0-1}$ then employed within the Fuel Iterations. Box 260 depicts the FUEL program which reduces fuel data from identified multiple sources, including an estimate of the unknown fuel, prepares a composite fuel, and then prepares an input file for the system simulator EX-FOSS. Reduction of fuel data involves combining the primary (computed) fuel chemistry from a previous iteration, with secondary fuels which have constant and known chemistries, producing a composite fuel. Box 270 is system data acquired from the process as on-line (in essentially real time) including at least the following Operating Parameters (refer to the section entitled MEANING OF TERMS for details): working fluid pressures, temperatures and flows, air psychrometrics, useful system output, Air pre-Heater Leakage Factor, and other related data. Box 280 depicts the system simulator EX-FOSS which, given an input of a composite fuel chemistry and composite calorific value from FUEL, inputs from Box 270, and routine set-up data, produces the following: boiler efficiency using the methods of '429, As-Fired fuel flow ($m_{AF}$) using Eq.(103), complete effluent concentrations of Eq.(29F), system efficiency and heat rate terms using Eqs. (104A) through (107B), effluent mass flow using the summation of Eq.(108), effluent volumetric flow using Eq.(110), emission rates of all effluents including the common pollutants using Eq.(109B), and other thermal performance parameters including, for example, energy flow to the working fluid heated by combustion products (BBTC), and the Firing Correction (HBC) which may be taken as zero. The determination of many of these parameters is taught herein, others are taught in '994 and '429. Box 285 depicts the HEATRATE program within which, given the corrected Choice Operating Parameters, produces fuel chemistry, the $L_{10}$ Factor of Eq.(70), and fuel calorific value for both the composite fuel (as either gross or net values), and, given the known compositions of secondary fuels, the composition of the primary (unknown) fuel is then computed. Designation 287 tests for convergence of the process based on composite fuel moles (x), certain effluents such as $CO_2$ and $H_2O$, calorific value and computed fuel water fraction; if the convergence criteria is not met the process continues to iterate from Box 260. In general, convergences lie within $0.5 \times 10^{-4}$ percent of the computed As-Fired fuel moles. Note that the iterations encompassing 260, 270, 280, 285 and 287 define what is meant by "Fuel Iterations". In summary, Fuel Iterations are the iterative calculations between EX-FOSS, as input with a known fuel chemistry and calorific value from a previous iteration, but with unknown effluents (to be computed by EX-FOSS, except for effluent $O_2$ which is input); and HEATRATE as input with known effluents (i.e., the corrected Choice Operating Parameters), but with unknown fuel chemistry and calorific value (to be computed by HEATRATE). If the convergence criteria is met, Box 292 then reports the final effluent and emission information. Typically, monitoring cycles are scheduled for every 2, 3 or 4 minutes using updated data based on 15 minute running averages. Once converged and all computations have been completed, Box 294 produces reportable results from the EX-FOSS and HEATRATE. Results include thermal performance information whereby improvements may be had, and provides reports to regulatory authorities. Box 296 represents a decision to return to Box 255 for another monitoring cycle (which may be automated). Box 298 of FIG. 20 is to quit.

Figure 22:
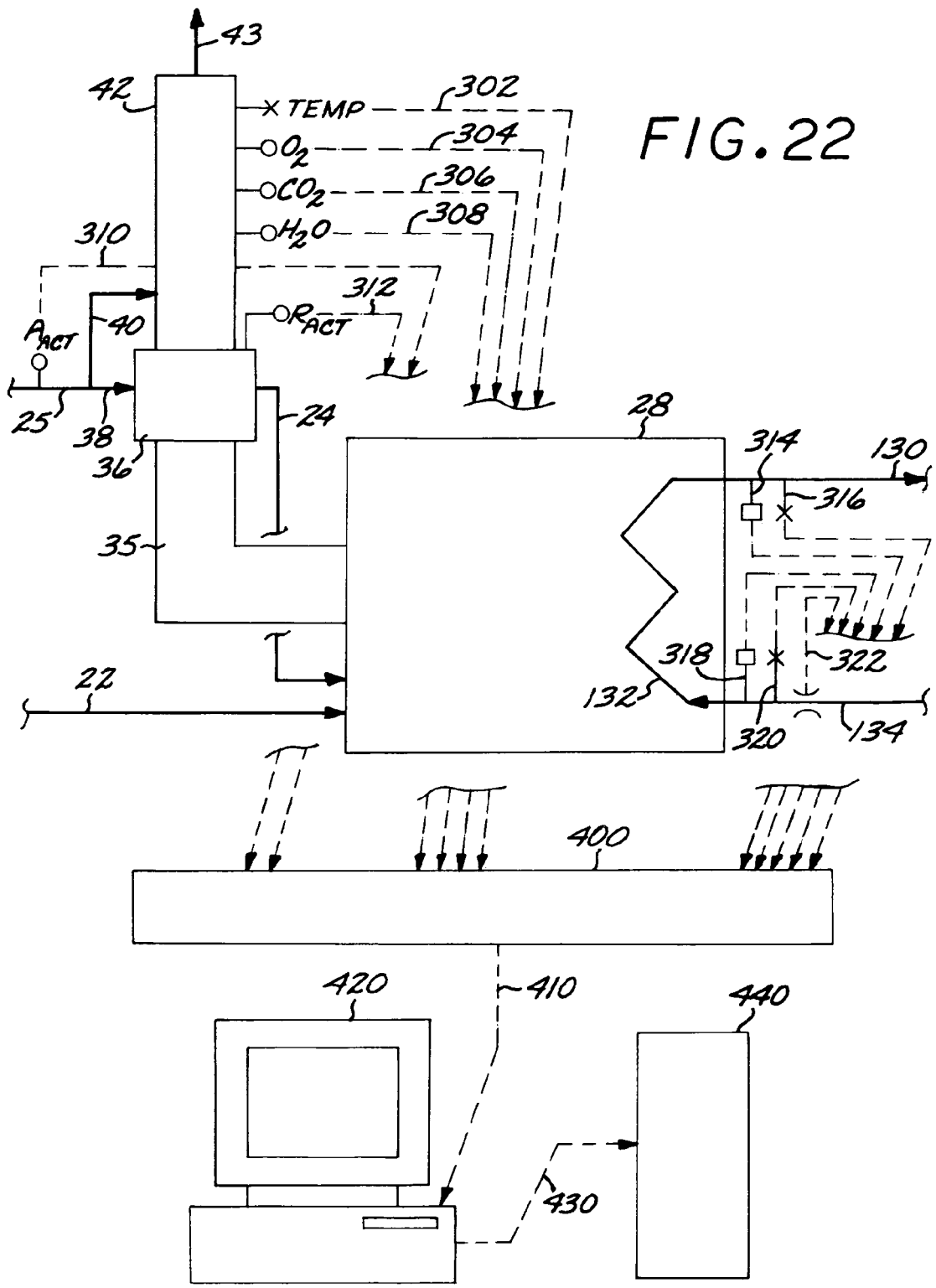
FIG. 22 is a representation of the apparatus of this invention showing a computer receiving Operating Parameters data including a selection of Choice Operating Parameters, from a power plant and producing output reports of computed quantities as taught herein.

FIG. 22 is a representation of the apparatus of this invention showing a computer receiving acquired system data, such as Operating Parameters, from a data acquisition device and producing output reports via a programmed computer. Specifically the represented power plant of FIG. 22, with item numbers corresponding to FIG. 19, and meaning the same as described for FIG. 19, is instrumented such that Operating Parameter data and selected Choice Operating Parameter (COP) data are collected in a data acquisition device 400. Within the data acquisition device 400 said data is typically converted to engineering units, averaged and/or archived, resulting in a set of acquired system data. Examples of said data acquisition device 400 include a data acquisition system, a Distributed Control System, an analog signal to digital signal conversion device, a pneumatic signal to digital signal conversion device, an auxiliary computer collecting data, or an electronic device with data collection and/or conversion features. After processing, the data acquisition device 400 transfers the set of acquired system data 410 to a computer 420 with a processing means and a memory means. The processing vehicle for transfer of the set of acquired system data 410 may be either by wire or by wireless transmission. The computer 420 is programmed with procedures which determine a complete As-Fired fuel chemistry, including fuel water and fuel ash. The computer 420 is also programmed with procedures which determine an Ultimate Analysis as a sub-set of a complete As-Fired fuel chemistry. The computer 420, operating with the programmed procedures descriptive of this disclosure produces at least a complete As-Fired fuel chemistry based on the genetics of a fossil fuel and a mathematical description of the thermal system. If 420 is programmed with the procedures descriptive of any one of the Input/Loss methods, the computer 420 produces at least an Ultimate Analysis based on stoichiometric descriptions of the combustion process. The computer 420, operating with the programmed procedures descriptive of this disclosure, also may determine any one or all of the following as taught herein: the fuel's calorific value, the energy flow to the working fluid heated by combustion products (BBTC) 33, boiler efficiency, fuel mass flow 22, effluent mass flow 43, effluent volumetric flow 43, emission rates of the pollutants, and/or system thermal efficiency. Instrumentation indicted in FIG. 22 includes Stack temperature 302 (also termed the effluent temperature), Stack $O_2$ (the COP $\Lambda_{7S}$) 304, Stack $CO_2$ (the COP $\Lambda_{1S}$) 306, and Stack $H_2O$ (the COP $\Lambda_{2S}$) 308. The COP for the concentration of $O_2$ in the combustion air ($\Lambda_5$) 310, using the symbol $A_{Act}$ in FIG. 22 and as taught above, is obtained either from instrumentation, from the United States National Aeronautics and Space Administration, or otherwise obtained by assumption or estimation, the value of which may then be corrected as taught in '877. The COP for the Air Pre-Heater Leakage Factor ($A_4$) 312, using the symbol $R_{Act}$ in FIG. 22 and as taught above, is obtained either from instrumentation as the ratio of $CO_2$ across the Air Pre-Heater 36 requiring $CO_2$ instruments at 35 and 42, or otherwise obtained by assumption or estimation based on the system operator's judgement, the value of which may then be corrected as taught in '877. These COPs represent an example of a selection of COPs, considered the most important; for other COPs see Eqs.(111S) through (119). The energy flow to the working fluid heated by combustion products (BBTC) derives from turbine cycle instrumentation. Said turbine cycle instrumentation, in a general fashion, is suggested by the following: steam pressure 314, steam temperature 316, feedwater pressure 318, feedwater temperature 320 and feedwater flow 322. All of these signals are transmitted to the data acquisition device 400 for processing. The determination of the steam enthalpy from pressure 314 and temperature 316 data, and determination of feedwater enthalpy from pressure 318 and temperature 320 data may occur within 400 or may occur within the computer 420. Further discussion of BBTC is provide under the MEANING OF TERMS, including the presence of a Reheater (not shown in FIG. 22). Output 430 consists of any one or all of the following quantities: complete As-Fired fuel chemistry, fuel calorific value, the energy flow to the working fluid heated by combustion products (BBTC), boiler efficiency, fuel mass flow, effluent mass flow, effluent volumetric flow, emission rates of the pollutants and/or system thermal efficiency. Output 430 may be made available to the system operator as paper reports printed on a printer 440, or may be made available to the system operator in electronic or visual forms using the computer 420. In summary, this invention teaches to operate a computer 420 to obtain a complete As-Fired fuel chemistry, including fuel water and fuel ash, based on the genetics of the fossil fuel, the mathematical description, the set of measurable Operating Parameters, the obtained effluent $H_2O$, the obtained fuel ash concentration, the concentration of $O_2$ in the combustion air local to the system and the Air Pre-Heater Leakage Factor.

What is claimed is:

1. A method for quantifying the operation of a thermal system burning a fossil fuel having a heat exchanger/combustion region producing combustion products, the method comprising the steps of:

operating a computer programmed with a mathematical description of the thermal system based on a closed-form solution, resulting in a programmed computer;

obtaining a set of Choice Operating Parameters selected from the group consisting of: a Stack $CO_2$, a Boiler $CO_2$, a Stack $H_2O$, a Boiler $H_2O$, an Air Pre-Heater Leakage Factor, a concentration of $O_2$ in the combustion air local to the thermal system, an indicated plant limestone flow, a Stack $O_2$, a Boiler $O_2$, and a relative humidity of the ambient air local to the thermal system;

obtaining a fuel ash concentration selected from the group consisting of: a constant value of fuel ash, a predictable value of fuel ash, a measured value of fuel ash determined from a fuel ash instrument and a value of fuel ash determined from an explicit solution, as an obtained fuel ash concentration; and operating the programmed computer to obtain a complete As-Fired fuel chemistry, including fuel water and fuel ash, based on the mathematical description of the thermal system, the set of Choice Operating Parameters, and the obtained fuel ash concentration.

2. A method for quantifying the operation of a thermal system burning a fossil fuel having a heat exchanger/combustion region producing combustion products, the method comprising the steps of:

before on-line operation,
developing a mathematical description of the thermal system based on a closed-form solution;
while operating on-line, the step of operating on-line comprising the steps of
obtaining a set of Choice Operating Parameters selected from the group consisting of: a Stack $CO_2$, a Boiler $CO_2$, a Stack $H_2O$, a Boiler $H_2O$, an Air Pre-Heater Leakage Factor, a concentration of $O_2$ in the combustion air local to the thermal system, an indicated plant limestone flow, a Stack $O_2$, a Boiler $O_2$, and a relative humidity of the ambient air local to the thermal system,
obtaining a fuel ash concentration selected from the group consisting of: a constant value of fuel ash, a predictable value of fuel ash, a measured value of fuel ash determined from a fuel ash instrument and a value of fuel ash determined from an explicit solution, as an obtained fuel ash concentration, and
operating a programmed computer to obtain a complete As-Fired fuel chemistry, including fuel water and fuel ash, based on the mathematical description of the thermal system, the set of Choice Operating Parameters, and the obtained fuel ash concentration.

3. A method for quantifying the operation of a thermal system burning a fossil fuel having a heat exchanger/combustion region producing combustion products, the method comprising the steps of:

operating a computer programmed with a mathematical description of the thermal system based on stoichiometric relationships and a genetics of the fossil fuel based on multi-variant analysis, resulting in a programmed computer,
obtaining a set of Choice Operating Parameters selected from the group consisting of: a Stack $CO_2$, a Boiler $CO_2$, a Stack $H_2O$, a Boiler $H_2O$, an Air Pre-Heater Leakage Factor, a concentration of $O_2$ in the combustion air local to the thermal system, an indicated plant limestone flow, a Stack $O_2$, a Boiler $O_2$, and a relative humidity of the ambient air local to the thermal system;
obtaining a fuel ash concentration selected from the group consisting of: a constant value of fuel ash, a predictable value of fuel ash, a measured value of fuel ash determined from a fuel ash instrument and a value of fuel ash determined from an explicit solution, as an obtained fuel ash concentration; and
operating the programmed computer to obtain a complete As-Fired fuel chemistry, including fuel water and fuel ash, based on the mathematical description of the thermal system, the set of Choice Operating Parameters, and the obtained fuel ash concentration.

4. A method for quantifying the operation of a thermal system burning a fossil fuel having a heat exchanger/combustion region producing combustion products, the method comprising the steps of:

before on-line operation,
developing a mathematical description of the thermal system based on combustion stoichiometrics and a genetics of the fossil fuel based on the multi-variant analysis;
while operating on-line, the step of operating on-line comprising the steps of
obtaining a set of Choice Operating Parameters selected from the group consisting of: a Stack $CO_2$, a Boiler $CO_2$, a Stack $H_2O$, a Boiler $H_2O$, an Air Pre-Heater Leakage Factor, a concentration of $O_2$ in the combustion air local to the thermal system, an indicated plant limestone flow, a Stack $O_2$, a Boiler $O_2$, and a relative humidity of the ambient air local to the thermal system;
obtaining a fuel ash concentration selected from the group consisting of: a constant value of fuel ash, a predictable value of fuel ash, a measured value of fuel ash determined from a fuel ash instrument and a value of fuel ash determined from an explicit solution, as an obtained fuel ash concentration; and
operating a programmed computer to obtain a complete As-Fired fuel chemistry, including fuel water and fuel ash, based on the mathematical description of the thermal system, the set of Choice Operating Parameters, and the obtained fuel ash concentration.

5. A method for quantifying the operation of a thermal system burning a fossil fuel having a heat exchanger/combustion region producing combustion products, the method comprising the steps of:

operating a computer programmed with a mathematical description of the thermal system based on stoichiometric relationships and a genetics of the fossil fuel based on the multi-variant analysis, resulting in a programmed computer,
measuring a set of measurable Operating Parameters, including at least effluent concentrations of $O_2$ and $CO_2$, these measurements being made at a location downstream of the heat exchanger/combustion region of the thermal system,
obtaining an effluent concentration of $H_2O$, as an obtained effluent $H_2O$,
obtaining a fuel ash concentration selected from the group consisting of: a constant value of fuel ash, a predictable value of fuel ash, a measured value of fuel ash determined from a fuel ash instrument and a value of fuel ash determined from an explicit solution, as an obtained fuel ash concentration,
obtaining a concentration of $O_2$ in the combustion air local to the system,
obtaining an Air Pre-Heater Leakage Factor, and
operating the programmed computer to obtain a complete As-Fired fuel chemistry, including fuel water and fuel ash, based on the mathematical description of the thermal system, the set of measurable Operating Parameters, the obtained effluent $H_2O$, the obtained fuel ash concentration, the concentration of $O_2$ in the combustion air local to the system and the Air Pre-Heater Leakage Factor.

6. A method for quantifying the operation of a thermal system burning a fossil fuel having a heat exchanger/combustion region producing combustion products, the method comprising the steps of:

before on-line operation,
developing a mathematical description of the thermal system based on stoichiometric relationships and genetics of the fossil fuel based on the multi-variant analysis;
the step of operating on-line comprising the steps of
measuring a set of measurable Operating Parameters, including at least effluent concentrations of $O_2$ and $CO_2$, these measurements being made at a location downstream of the heat exchanger/combustion region of the thermal system, obtaining an effluent concentration of $H_2O$, as an obtained effluent $H_2O$, obtaining a fuel ash concentration selected from the group consisting of: a constant value of fuel ash, a predictable value of fuel ash, a measured value of fuel ash determined from a fuel ash instrument and a value of fuel ash determined from an explicit solution, as an obtained fuel ash concentration, obtaining a concentration of $O_2$ in the combustion air local to the system, obtaining an Air Pre-Heater Leakage Factor, and operating a programmed computer to obtain a complete As-Fired fuel chemistry, including fuel water and fuel ash, based on the mathematical description of the thermal system, the set of measurable Operating Parameters, the obtained effluent $H_2O$, the obtained fuel ash concentration, the concentration of $O_2$ in the combustion air local to the system and the Air Pre-Heater Leakage Factor.

7. The method of claims 1, 2, 3, 4, 5 or 6, wherein the thermal system comprises a thermal system selected from the group consisting of: a coal-burning power plant, a lignite-burning power plant, an oil-burning power plant, a gas-fired power plant, a biomass combustor, a fluidized bed combustor, a conventional electric power plant, a steam generator, a package boiler, a combustion turbine, a combustion turbine with a heat recovery boiler, a power plant burning Irish peat, and a Recovery Boiler used in the pulp and paper industry.

8. The method of claims 1, 2, 3, 4, 5 or 6, wherein the step of operating the programmed computer to obtain the complete As-Fired fuel chemistry includes the steps of operating the programmed computer to obtain a fuel chemistry including at least one fuel constituent selected from the group consisting of: weight percent carbon, weight percent hydrogen and weight percent oxygen of the fuel, and calculating a fuel calorific value based on the fuel chemistry in units of kJ/kg, the step of calculating including a step of forming products of numerical coefficients times the weight percent of the fuel constituent, wherein at least one of the numerical coefficients is selected from the group consisting of from 325 to 358 for weight percent carbon, from 896 to 1454 for weight percent hydrogen, and from –86 to –181 for weight percent oxygen and combinations thereof.

9. The method of claims 1, 2, 3, 4, 5 or 6, wherein the step of operating the programmed computer to obtain the complete As-Fired fuel chemistry includes the steps of operating the programmed computer to obtain a fuel chemistry including at least one fuel constituent selected from the group consisting of: weight percent carbon, weight percent hydrogen and weight percent oxygen of the fuel, and calculating a fuel calorific value based on the fuel chemistry in units of Btu per pound-mass, the step of calculating including a step of forming products of numerical coefficients times the weight percent of the fuel constituent, wherein at least one of the numerical coefficients is selected from the group consisting of from 140 to 154 for weight percent carbon, from 385 to 625 for weight percent hydrogen, and from –37 to –78 for weight percent oxygen and combinations thereof.

10. The method of claims 1, 2, 3, 4, 5 or 6, wherein the step of obtaining the concentration of $O_2$ in the combustion air local to the system includes the step of using a concentration of $O_2$ in the combustion air local to the system obtained from the United States National Aeronautics and Space Administration.

11. The method of claims 1, 3 or 5, wherein the step of operating the computer programmed with the mathematical description of the thermal system, includes the step of operating the computer programmed with the mathematical description of the thermal system based on one of the Input/Loss methods.

12. The method of claims 2, 4 or 6, wherein the step of developing the mathematical description of the thermal system, includes the step of developing the mathematical description of the thermal system based on one of the Input/Loss methods.

13. The method of claims 1, 3 or 5, wherein the step of operating the computer programmed with the mathematical description of the thermal system, includes the step of operating the computer programmed with the mathematical description of the thermal system based on matrix solution.

14. The method of claims 2, 4 or 6, wherein the step of developing the mathematical description of the thermal system, includes the step of developing the mathematical description of the thermal system based on matrix solution.

15. The method of claims 1, 2, 3 or 4, including, after the step of operating the programmed computer to obtain the complete As-Fired fuel chemistry, the additional steps of obtaining a corrected $L_{10}$ Factor based on the complete As-Fired fuel chemistry;

establishing a reference $L_{10}$ Factor;

operating the programmed computer to obtain a multidimensional minimization analysis based on minimizing error between the corrected $L_{10}$ Factor and the reference $L_{10}$ Factor, such that at least one Choice Operating Parameter of a set of Choice Operating Parameters is corrected, the set of Choice Operating Parameters selected from the group consisting of: effluent concentration of $CO_2$, effluent concentration of $O_2$, the obtained effluent $H_2O$, the concentration of $O_2$ in the ambient air entering the thermal system and the Air Pre-Heater Leakage Factor resulting in a set of correction factors; and operating the programmed computer by applying in subsequent on-line analysis the set of correction factors to the set of Choice Operating Parameters.

16. The method of claims 1, 2, 3 or 4, after the step of operating the programmed computer to obtain the complete As-Fired fuel chemistry, the additional step which comprises operating the programmed computer to obtain an As-Fired fuel calorific value as a function of the complete As-Fired fuel chemistry.

17. The method of claim 16, after the step of operating the programmed computer to obtain an As-Fired fuel calorific value, the additional steps which comprise measuring an effluent temperature of the combustion gas, operating the programmed computer to obtain a boiler efficiency as a function of the complete As-Fired fuel chemistry, the set of Choice Operating Parameters, the As-Fired fuel calorific value and the effluent temperature.

18. The method of claim 16, after the step of operating the programmed computer to obtain the As-Fired fuel calorific value, the additional steps which comprise obtaining a set of effluent concentrations including at least effluent $SO_2$, and operating the programmed computer to obtain individual emission rates based on the As-Fired fuel calorific value and the set of effluent concentrations.

19. The method of claim 17, after the step of operating the programmed computer to obtain the boiler efficiency, the additional steps which comprise measuring an electrical generation produced from the thermal system, measuring an energy flow to the working fluid heated by combustion products; and operating the programmed computer to obtain a system thermal efficiency as a function of the boiler efficiency, the electrical generation produced, and the energy flow to the working fluid.

20. The method of claim 17, after the step of operating the programmed computer to obtain the boiler efficiency, the additional steps which comprise measuring an energy flow to the working fluid heated by combustion products, and operating the programmed computer to obtain an As-Fired fuel flow based on the boiler efficiency, the As-Fired fuel calorific value, and the energy flow to the working fluid.

21. The method of claim 20, after the step of operating the programmed computer to obtain the As-Fired fuel flow, the additional step which comprises operating the programmed computer to obtain a total effluent flow based on the As-Fired fuel flow.

22. The method of claim 20, after the step of operating the programmed computer to obtain the As-Fired fuel flow, the additional steps which comprise obtaining a set of effluent concentrations including at least effluent $SO_2$, and operating the programmed computer to obtain individual effluent flows based on the set of effluent concentrations and the As-Fired fuel flow.

23. The method of claim 20, including, after the step of operating the programmed computer to obtain the As-Fired fuel flow, the additional steps which comprise obtaining an indicated plant fuel flow associated with the thermal system;

operating the programmed computer to perform a multi-dimensional minimization analysis based on minimizing error between the As-Fired fuel flow and the indicated plant fuel flow, such that at least one Choice Operating Parameter of a set of Choice Operating Parameters is corrected, the set of Choice Operating Parameters selected from the group consisting of: effluent concentration of $CO_2$, effluent concentration of $O_2$, the obtained effluent $H_2O$, the concentration of $O_2$ in the ambient air entering the thermal system and the Air Pre-Heater Leakage Factor resulting in a set of correction factors; and operating the programmed computer by applying in subsequent analysis the set of correction factors to the set of Choice Operating Parameters.

24. The method of claim 20, after the step of operating the programmed computer to obtain the As-Fired fuel flow, the additional steps which comprise obtaining a gas density and a molecular weight of the effluent gas, and operating the programmed computer to obtain an effluent volumetric flow based on the As-Fired fuel flow, the gas density and the molecular weight of the effluent gas.

25. The method of claims 5 or 6, after the step of operating the programmed computer to obtain the complete As-Fired fuel chemistry, the additional step comprising of operating the programmed computer to obtain an As-Fired fuel calorific value as a function of the complete As-Fired fuel chemistry.

26. The method of claim 25, wherein the step of measuring the set of measurable Operating Parameters includes the step of measuring an effluent temperature; and wherein the method further includes an additional step, after the step of operating the programmed computer to obtain a complete As-Fired fuel chemistry, of operating the programmed computer to obtain a boiler efficiency as a function of the complete As-Fired fuel chemistry, the effluent temperature, effluent concentrations and the As-Fired fuel calorific value.

27. The method of claim 25, after the step of operating the programmed computer to obtain the As-Fired fuel calorific value, the additional steps comprising obtaining a set of effluent concentrations including at least effluent $SO_2$, and operating the programmed computer to obtain individual emission rates based on the As-Fired fuel calorific value and the set of effluent concentrations.

28. The method of claim 26, wherein the step of measuring the set of measurable Operating Parameters includes the steps of measuring an electrical generation produced from the thermal system, and measuring an energy flow to the working fluid heated by combustion products; and wherein the method further includes an additional step, after the step of operating the programmed computer to obtain a boiler efficiency, of operating the programmed computer to obtain a system thermal efficiency as a function of the electrical generation produced, the energy flow to the working fluid and the boiler efficiency.

29. The method of claim 26, wherein the step of measuring the set of measurable Operating Parameters includes the step of measuring an energy flow to the working fluid heated by combustion products; and wherein the method further includes an additional step, after the step of operating the programmed computer to obtain a boiler efficiency, of operating the programmed computer to obtain an As-Fired fuel flow based on the boiler efficiency, the As-Fired fuel calorific value, and the energy flow to the working fluid.

30. The method of claim 29, after the step of operating the programmed computer to obtain the As-Fired fuel flow, an additional step comprising operating the programmed computer to obtain a total effluent flow based on the As-Fired fuel flow.

31. The method of claim 29, after the step of operating the programmed computer to obtain the As-Fired fuel flow, the additional steps comprising obtaining a set of effluent concentrations including at least effluent $SO_2$, and operating the programmed computer to obtain individual effluent flows based on the set of effluent concentrations and the As-Fired fuel flow.

32. The method of claim 29, including, after the step of operating the programmed computer to obtain the As-Fired fuel flow, the additional steps of obtaining an indicated plant fuel flow associated with the thermal system;

operating the programmed computer to obtain a multidimensional minimization analysis based on minimizing error between the As-Fired fuel flow and the indicated plant fuel flow, such that at least one Choice Operating Parameter of a set of Choice Operating Parameters is corrected, the set of Choice Operating Parameters selected from the group consisting of: effluent concentration of $CO_2$, effluent concentration of $O_2$, the obtained effluent $H_2O$, the concentration of $O_2$ in the ambient air entering the thermal system and the Air Pre-Heater Leakage Factor resulting in a set of correction factors; and operating the programmed computer by applying in subsequent analysis the set of correction factors to the set of Choice Operating Parameters.

33. The method of claim 29, after the step of operating the programmed computer to obtain the As-Fired fuel flow, the additional steps comprising obtaining a standard density of the effluent gas, obtaining an average molecular weight of the effluent gas, and operating the programmed computer to obtain a total effluent dry volumetric flow based on the As-Fired fuel flow, the standard density and the average molecular weight of the effluent gas.

34. The method of claims 5 or 6, wherein the step of measuring the set of measurable Operating Parameters includes an additional step of obtaining a set of effluent concentrations, the set of effluent concentrations containing at least one selected from the group consisting of: CO, $SO_2$ and $NO_X$, resulting in a set of pollutant concentrations; and wherein the step of operating the programmed computer to obtain a complete As-Fired fuel chemistry includes the step of operating the programmed computer to obtain the complete As-Fired fuel chemistry, including fuel water and fuel ash, based on the mathematical description of the thermal system, the set of measurable Operating Parameters, the obtained effluent $H_2O$, the obtained fuel ash concentration, the concentration of $O_2$ in the combustion air local to the system, the Air Pre-Heater Leakage Factor, and the set of effluent pollutant concentrations.

35. The method of claims 1, 3 or 5, wherein the step of operating the computer programmed with the mathematical description of the thermal system includes the additional step, of operating the computer programmed with the mathematical description of the thermal system based on stoichiometric relationships and genetics of the fossil fuel in the form $CH_{c2}O_{c3}$, the reduced value c3 selected from the group consisting of a value from 0.009 to 0.024 for anthracite coal, from 0.025 to 0.054 for semi-anthracite coal, from 0.055 to 0.121 for the coal Ranks of hvAb and hvBb, from 0.122 to 0.170 for sub-bituminous A coal, from 0.171 to 0.183 for Powder River Basin coal, from 0.184 to 0.200 for sub-bituminous B coal, from 0.201 to 0.215 for sub-bituminous C coal, from 0.216 to 0.230 for lignite A, from 0.390 to 0.458 for Greek lignite, and from 0.459 to 0.520 for Irish peat, and combinations thereof.

36. The method of claims 2, 4 or 6, wherein the step of developing the mathematical description of the thermal system includes the additional step, of developing the mathematical description of the thermal system based on stoichiometric relationships and genetics of the fossil fuel in the form $CH_{c2}O_{c3}$, the reduced value c3 selected from the group consisting of a value from 0.009 to 0.024 for anthracite coal, from 0.025 to 0.054 for semi-anthracite coal, from 0.055 to 0.121 for the coal Ranks of hvAb and hvBb, from 0.122 to 0.170 for sub-bituminous A coal, from 0.171 to 0.183 for Powder River Basin coal, from 0.184 to 0.200 for sub-bituminous B coal, from 0.201 to 0.215 for sub-bituminous C coal, from 0.216 to 0.230 for lignite A, from 0.390 to 0.458 for Greek lignite, and from 0.459 to 0.520 for Irish peat, and combinations thereof.

37. The method of claims 1, 2, 3 or 4, wherein the step of obtaining the set of Choice Operating Parameters includes obtaining a set of Choice Operating Parameters selected from the group consisting of: a Stack $CO_2$, a Boiler $CO_2$, a Stack $H_2O$, a Boiler $H_2O$, an Air Pre-Heater Leakage Factor, a concentration of $O_2$ in the combustion air local to the thermal system, an indicated plant limestone flow, a Stack $O_2$, a Boiler $O_2$, a relative humidity of the ambient air local to the thermal system, and a tube leakage flow rate.

38. The method of claims 1, 2, 3 or 4, after the step of operating the programmed computer to obtain the complete As-Fired fuel chemistry, the additional step comprising operating the programmed computer to obtain a set of correction factors to be applied to the set of Choice Operating Parameters, the set of Choice Operating Parameters selected from the group consisting of: effluent concentration of $O_2$, effluent concentrations of $CO_2$, the concentration of $O_2$ in the combustion air local to the system and the Air Pre-Heater Leakage Factor, the set of correction factors selected from the group consisting of: a set of obtained correction factors, and a set of correction factors based on a multidimensional minimization analysis.

39. The method of claims 1, 2, 3 or 4, wherein the step of operating the programmed computer to obtain the complete As-Fired fuel chemistry, comprises the step of operating the programmed computer to obtain an Ultimate Analysis of the fuel chemistry based on the mathematical description of the thermal system, the set of Choice Operating Parameters and the obtained fuel ash concentration.

40. The method of claims 5 or 6, wherein the step of operating the programmed computer to obtain the complete As-Fired fuel chemistry, comprises the step of operating the programmed computer to obtain an Ultimate Analysis of the fuel chemistry based on the mathematical description of the thermal system, said mathematical description based on stoichiometric relationships and genetics of the fossil fuel, the set of measurable Operating Parameters, the obtained effluent $H_2O$, the concentration of $O_2$ in the combustion air local to the system and the Air Pre-Heater Leakage Factor.

* * * * *

UNITED STATES PATENT AND TRADEMARK OFFICE
CERTIFICATE OF CORRECTION

Figure 20B:
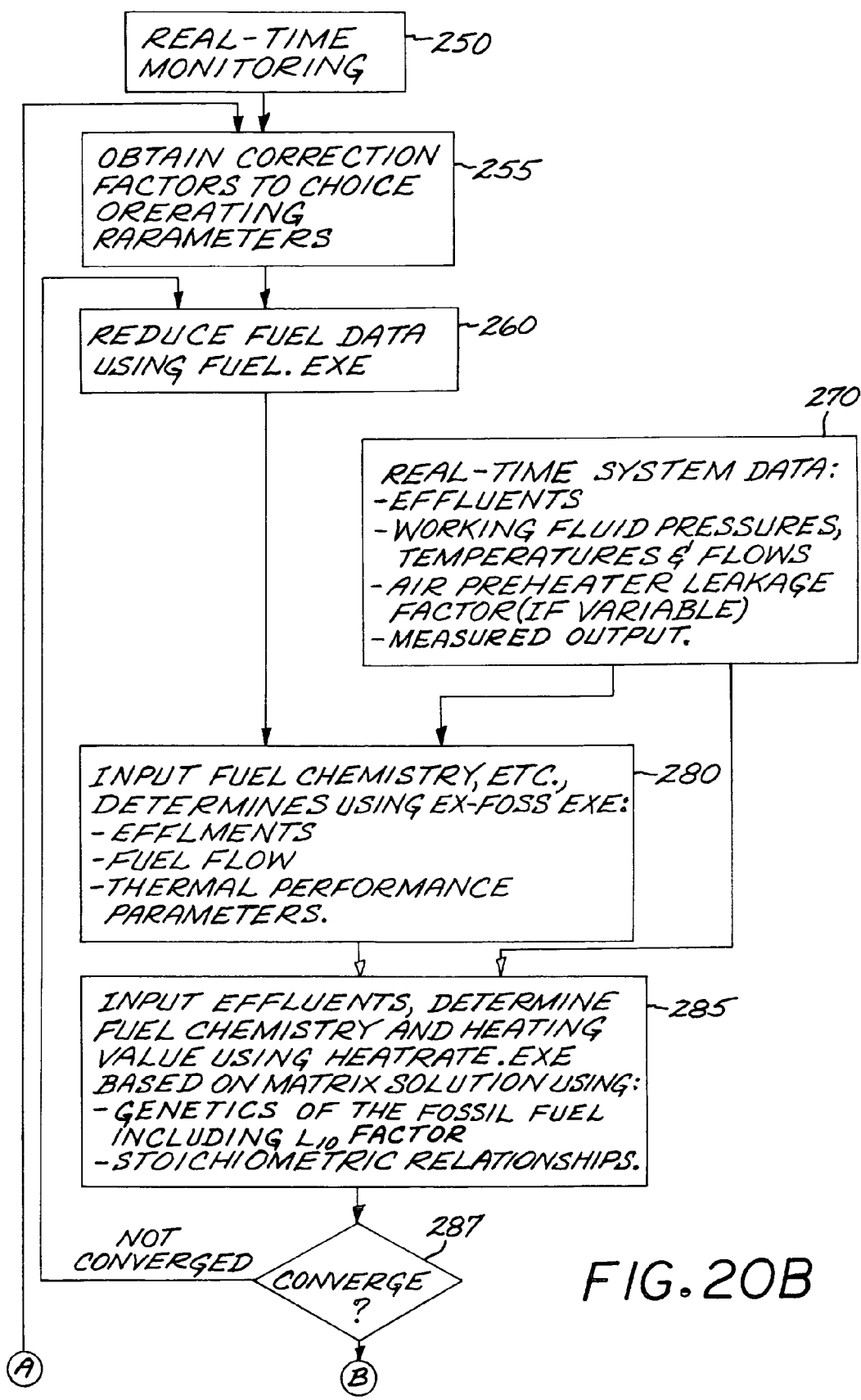
Figure 20C:
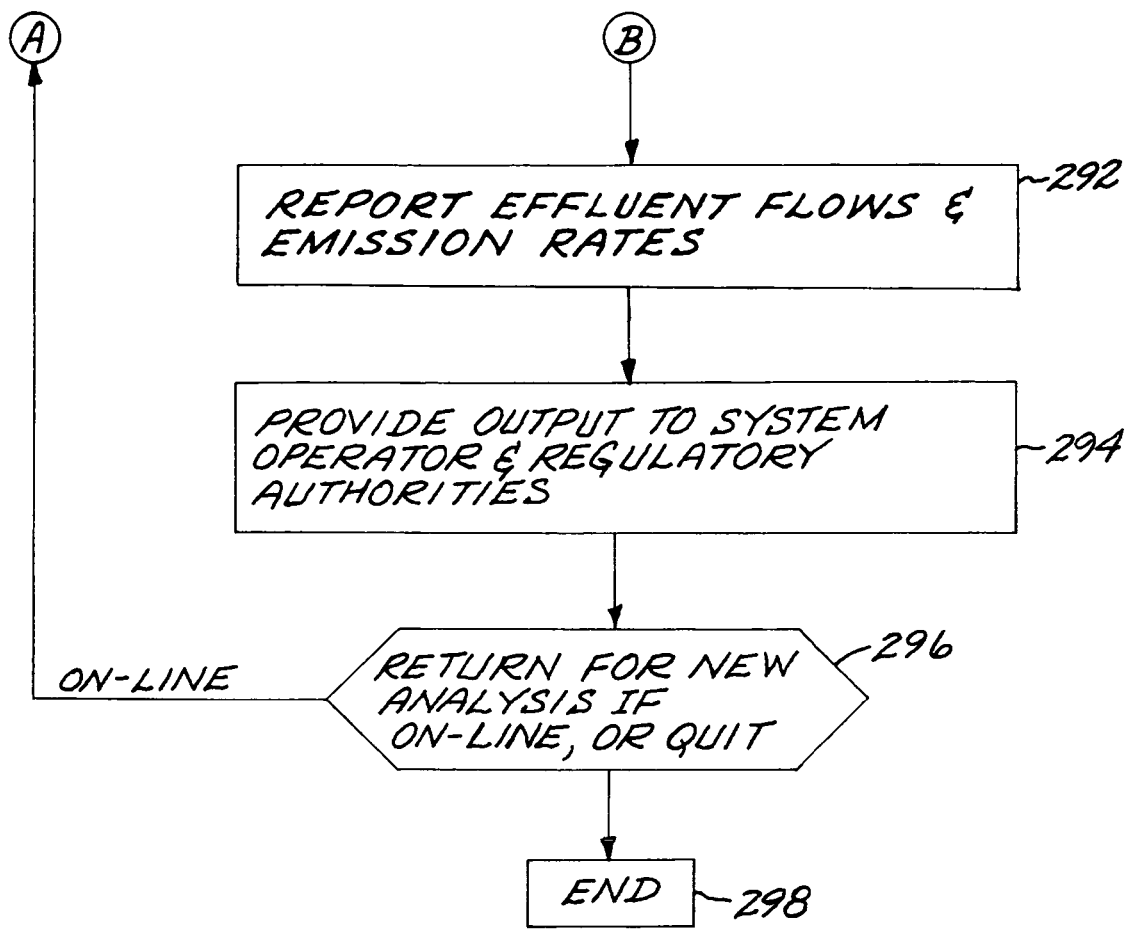

PATENT NO. : 7,328,132 B2
APPLICATION NO. : 11/378999
DATED : February 5, 2008
INVENTOR(S) : Fred D. Lang It is certified that error appears in the above-identified patent and that said Letters Patent is hereby corrected as shown below:

Figure 20B,
Box 255, delete "orerating rarameters" and insert -- operating parameters --

Figure 20B,
Box 270, delete "measured output" and insert -- measured useful system output --

Column 1,
Lines 35-36, delete "how effluent concentrations resultant from combustion may be" and insert:
-- how measurements of effluent concentrations, resultant from combustion, may be --

Column 2,
Line 34, delete "correction" and insert -- correlation --

Column 14,
Line 43, delete "Eq.(23); molar fraction" and insert -- Eq.(24); molar fraction --
Line 50, the embedded equation should read as follows:
-- $\gamma = [(m_{LS}/m_{AF})xN_{AF}/(\xi\, b_{PLS}\, N_{CaCO3})] - 1.0$ --

Column 18,
Line 67, delete "(if consistency" and insert -- (if consistently --

Column 19,
Line 4, delete "arc" and insert -- are --

Column 20,
Line 54, delete "water content Often" and insert -- water content. Often --

Column 23,
Line 10, delete "the system's local combustion air." and insert -- the system's local combustion air noting that $\phi_{Act}$ can be lower than the reference ratio (given local oxygen starving) or higher (given use of an oxygen enriched combustion air). --
Line 21, delete "defined above such" and insert -- defined such --

UNITED STATES PATENT AND TRADEMARK OFFICE
CERTIFICATE OF CORRECTION

PATENT NO.         : 7,328,132 B2
APPLICATION NO. : 11/378999
DATED              : February 5, 2008
INVENTOR(S)        : Fred D. Lang It is certified that error appears in the above-identified patent and that said Letters Patent is hereby corrected as shown below:

Throughout the Patent:
In Eqs.(20)-(25), (29F), (30), (36), (48B), (53), (55), (58) and elsewhere, the symbols $\varphi_{Act}$ and $\phi_{Act}$ are the same as defined by Col. 14, Lines 61-63.

Column 27,
Line 12, delete "= 1.00 is a convenience," and insert
-- = 1.00 stems from conservation, --

Column 30,
Equations on Lines 25-30 should read as follows:
$$-- \alpha_{MAF-4} + \alpha_{MAF-5} = J_{OHC1} + K_{OHC1}\alpha_{MAF-3} \quad (61)$$
$$\alpha_{MAF-4} + \alpha_{MAF-3} = J_{OHC2} + K_{OHC2}\alpha_{MAF-5} \quad (62)$$
$$\alpha_{MAF-5} + \alpha_{MAF-3} = J_{OHC3} + K_{OHC3}\alpha_{MAF-4} \quad (63) --$$

Column 34,
Line 8, the title of TABLE 6 should read as follows:
-- Reduction of Multi-Variant Analysis to $CH_{c2}O_{c3}$ --

Column 37,
Equations on Lines 42-49 should read as follows:
$$-- -\xi_{L1}\alpha_{MAF-3} + \alpha_{MAF-4} + \alpha_{MAF-5} = \xi_{L2} \quad (74)$$
$$\text{where:} \quad \xi_{L1} \equiv H_{OHC1} / H_{OHC2} \quad (75)$$
$$\xi_{L2} \equiv (G_{OHC1} - G_{OHC2}) / H_{OHC2} \quad (76) --$$

Column 38,
Equations on Lines 1-6 should read as follows:
$$-- -2\alpha_{MAF-3} - \xi_{C1}\alpha_{MAF-4} + \alpha_{MAF-5} + 0.0 = 0.0 \quad (77)$$
$$\text{where:} \quad \xi_{C1} \equiv (\Gamma_{H2O} - 2\Gamma_{O2}) / \Gamma_{CO2} \quad (78) --$$
Equations on Lines 17-25 should read as follows:
$$-- -2\alpha_{MAF-3} - \xi_{S1}\alpha_{MAF-4} + \alpha_{MAF-5} + 2\alpha_{MAF-6} + 0.0 = 0.0 \quad (80)$$
$$\text{where:} \quad \xi_{S1} \equiv (\Gamma_{H2O} - 2\Gamma_{OHS} - 2\xi_{S6}) / \Gamma_{CO2} \quad (81)$$
$$\xi_{S6} \equiv k_{Act} [\Gamma_{SO3}/(1.0 - \Gamma_{SO3})]/(2\,\Gamma_{ESP})$$
$$+ b_{PLS}[\sigma/2 - 1.0 - \gamma + \sigma z/2 + \sigma\,\Gamma_{SO3}/(2.0 - 2\Gamma_{SO3})] \quad (82) --$$

Column 45,
Line 29, delete "by the following:" and insert -- through use of the following terms: --
Line 55, delete the expression "($M_W$ = 1.40)" and insert -- ($MC_W$ = 1.40) --

UNITED STATES PATENT AND TRADEMARK OFFICE
CERTIFICATE OF CORRECTION

PATENT NO.       : 7,328,132 B2
APPLICATION NO.  : 11/378999
DATED            : February 5, 2008
INVENTOR(S)      : Fred D. Lang It is certified that error appears in the above-identified patent and that said Letters Patent is hereby corrected as shown below:

Column 46,
Lines 13-14, delete "using an independent parameter associated with combustion, ambient relative humidity, which is not directly influenced" and insert -- using a parameter which is independent of the combustion process, such as ambient relative humidity. Ambient relative humidity is not directly influenced --
Line 61, delete "fuel ash (as" and insert -- fuel ash as --

Column 49,
Line 61, delete "system 25 ($\Lambda_g$)." and insert -- system 25 ($\Lambda_9$). --
Line 67, delete "term $b_Z$ ." and insert -- term $b_Z$ associated with item 29. --

Column 50,
Line 1, delete "employ '877 methods" and insert
    -- employ methods taught in the section entitled CORRECTION OF CHOICE OPERATING PARAMETERS AND SYSTEM BENCHMARKING, and as further discussed in '877 --

Column 52,
Line 3, delete "Factor ($A_4$) 312" and insert -- Factor ($\Lambda_4$) 312 --
Line 6, delete "and 42 or" and insert
    -- and 42 if an on-line signal is required, or as --

Signed and Sealed this

Seventeenth Day of June, 2008

JON W. DUDAS
*Director of the United States Patent and Trademark Office*